(12) United States Patent
Hara et al.

(10) Patent No.: US 8,058,035 B2
(45) Date of Patent: Nov. 15, 2011

(54) METHOD FOR PRODUCING AN L-AMINO ACID

(75) Inventors: Yoshihiko Hara, Kawasaki (JP); Hiroshi Izui, Kawasaki (JP); Jun Nakamura, Kawasaki (JP); Ranko Nishi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/478,049

(22) Filed: Jun. 4, 2009

(65) Prior Publication Data

US 2009/0286290 A1 Nov. 19, 2009

Related U.S. Application Data

(63) Continuation of application No. PCT/JP2007/067387, filed on Sep. 6, 2007.

(30) Foreign Application Priority Data

Dec. 19, 2006 (JP) ................................ 2006-341019

(51) Int. Cl.
*C12P 13/24* (2006.01)
*C12P 13/04* (2006.01)

(52) U.S. Cl. ......... 435/107; 435/106; 435/110; 435/114

(58) Field of Classification Search .................. None
See application file for complete search history.

(56) References Cited

U.S. PATENT DOCUMENTS

| | | | |
|---|---|---|---|
| 3,220,929 A | 11/1965 | Kinoshita et al. | |
| 3,563,857 A | 2/1971 | Oki et al. | |
| 5,168,056 A | 12/1992 | Frost | |
| 5,378,616 A | 1/1995 | Tujimoto et al. | |
| 5,393,671 A | 2/1995 | Tujimoto et al. | |
| 5,492,818 A | 2/1996 | Nakazawa et al. | |
| 5,776,736 A | 7/1998 | Frost et al. | |
| 5,906,925 A | 5/1999 | Liao | |
| 5,977,331 A | 11/1999 | Asakura et al. | |
| 7,205,132 B2 | 4/2007 | Hirano et al. | |
| 7,247,459 B1 | 7/2007 | Izui et al. | |
| 7,344,874 B2 | 3/2008 | Hara et al. | |
| 7,482,140 B2 | 1/2009 | Takai et al. | |
| 7,501,282 B2 | 3/2009 | Hara et al. | |
| 2001/0019836 A1 | 9/2001 | Moriya et al. | |
| 2003/0100079 A1* | 5/2003 | Mockel et al. | ................ 435/106 |
| 2004/0152175 A1 | 8/2004 | Nakamura et al. | |
| 2006/0040365 A1 | 2/2006 | Kozlov et al. | |
| 2006/0063240 A1* | 3/2006 | Katashkina et al. | .......... 435/106 |
| 2006/0088919 A1 | 4/2006 | Rybak et al. | |
| 2006/0141588 A1 | 6/2006 | Nakamura et al. | |
| 2007/0172932 A1 | 7/2007 | Hirano et al. | |
| 2007/0254345 A1 | 11/2007 | Fukui et al. | |
| 2009/0104683 A1 | 4/2009 | Takai et al. | |

FOREIGN PATENT DOCUMENTS

| | | |
|---|---|---|
| EP | 0952221 | 10/1999 |
| EP | 0955368 | 11/1999 |
| EP | 1078989 | 2/2001 |
| JP | 32-9393 | 11/1932 |
| JP | 63-119688 | 5/1988 |

OTHER PUBLICATIONS

Sousa et al. Microbiology 148(Pt5):1291-1303, 2002.*
Kikuchi, M., et al., Biotechnology of Amino Acid Production, progress in industrial microbiology vol. 24, pp. 101-116, Kodansha Ltd. Tokyo (corresponding to Kunihiko Akashi et al., "Amino acid fermentation", pp. 195-215, 1986, Japan Scientific Societies Press).
International Preliminary Report on Patentability for PCT Patent App. No. PCT/JP2007/067387 (Jul. 2, 2009).
U.S. Appl. No. 11/844,559, Hara et al., filed Aug. 24, 2007.
U.S. Appl. No. 12/034,087, Hirano et al., filed Feb. 20, 2008.
U.S. Appl. No. 12/034,101, Hirano et al., filed Feb. 20, 2008.
U.S. Appl. No. 12/179,845, Chinen et al., filed Jul. 25, 2008.
U.S. Appl. No. 12/388,133, Hara et al., filed Feb. 18, 2009.
Creaghan, I. T., et al., "Succinate Dehydrogenase-dependent Nutritional Requirement for Succinate in Mutants of *Escherichia coli* K12," J. General Microbiol. 1978;107(Part 1):1-13.
International Search Report for PCT Patent App. No. PCT/JP2007/067387 (Dec. 4, 2007).

* cited by examiner

*Primary Examiner* — Tekchand Saidha
*Assistant Examiner* — Younus Meah
(74) *Attorney, Agent, or Firm* — Shelly Guest Cermak; Cermak Nakajima LLP

(57) ABSTRACT

A microorganism which has an L-amino acid producing ability and has been modified so that succinate dehydrogenase activity and α-ketoglutarate dehydrogenase activity are decreased is cultured in a medium to produce and accumulate an L-amino acid in the medium or cells of the microorganism, and the L-amino acid is collected from the medium or cells to produce the L-amino acid.

7 Claims, 2 Drawing Sheets

METHOD FOR PRODUCING AN L-AMINO ACID

This application is a continuation under 35 U.S.C. §120 of PCT Patent Application No. PCT/JP2007/067387, filed Sep. 6, 2007, which claims priority under 35 U.S.C. §119 to Japanese Patent Application No. 2006-341019, filed on Dec. 19, 2006, which are incorporated in their entireties by reference. The Sequence Listing in electronic format filed herewith is also hereby incorporated by reference in its entirety (File Name: US-398_Seq_List; File Size: 199 KB; Date Created: Jun. 4, 2009).

BACKGROUND OF THE INVENTION

1. Field of the Invention

The present invention relates to a method for producing an L-amino acid such as L-glutamic acid using a microorganism. L-Glutamic acid is useful as an ingredient of seasonings, and the other L-amino acids are useful in industry as animal feed additives, health food ingredients, amino acid infusions, and the like.

2. Brief Description of the Related Art

Methods for producing a target substance such as an L-amino acid by fermentation using a bacterium can include methods of using a wild-type bacterium (wild-type strain), an auxotrophic strain derived from a wild-type strain, a metabolic regulation mutant strain derived from a wild-type strain as a strain resistant to various drugs, a strain having properties of both auxotrophic strain and metabolic regulation mutant, and the like.

For example, L-glutamic acid can be produced by fermentation using an L-glutamic acid-producing bacterium of the so-called coryneform bacterium belonging to the genus *Brevibacterium, Corynebacterium* or *Microbacterium* or a mutant strain thereof (refer to Kunihiko Akashi, et. al. "Amino Acid Fermentation", Gakkai Shuppan Center, 1986, pp. 195-215). Moreover, as methods for producing L-glutamic acid using other strains, methods utilizing a microorganism belonging to the genus *Bacillus, Streptomyces, Penicillium*, or the like (refer to U.S. Pat. No. 3,220,929), *Pseudomonas, Arthrobacter, Serratia, Candida*, or the like (refer to U.S. Pat. No. 3,563,857), *Bacillus, Pseudomonas, Serratia, Aerobacter aerogenes* (currently *Enterobacter aerogenes*), or the like (refer to, Japanese Patent Publication (Kokoku) No. S32-9393), a mutant strain of *Escherichia coli* (refer to Japanese Patent Laid-open (Kokai) No. H5-244970), and the like are known. Furthermore, the inventors of the present invention proposed a method of producing L-glutamic acid using a microorganism belonging to the genus *Klebsiella, Erwinia, Pantoea*, or *Enterobacter* (refer to Japanese Patent Laid-open Nos. 2000-106869, 2000-189169 and 2000-189175).

In recent years, recombinant DNA techniques have been used in the production of target substances by fermentation. For example, L-amino acid productivity of a bacterium can be improved by enhancing expression of a gene encoding an L-amino acid biosynthetic enzyme (U.S. Pat. Nos. 5,168,056 and 5,776,736), or by enhancing uptake of a carbon source to the L-amino acid biosynthesis system (U.S. Pat. No. 5,906,925).

For example, as for L-glutamic acid production, it was reported that introduction of a gene encoding citrate synthase from *Escherichia coli* or *Corynebacterium glutamicum* was effective for enhancement of L-glutamic acid-producing ability in a coryneform bacterium belonging to the genus *Corynebacterium* or *Brevibacterium* (refer to Japanese Patent Laid-open No. H7-121228). Furthermore, it was reported that introduction of a citrate synthase gene from a coryneform bacterium into an enterobacterium belonging to the genus *Enterobacter, Klebsiella, Serratia, Erwinia* or *Escherichia* was effective for enhancement of L-glutamic acid-producing ability (refer to Japanese Patent Laid-open No. 2000-189175).

It is also known that microorganisms which are deficient in α-ketoglutarate dehydrogenase (α-KGDH) produce a marked amount of L-glutamic acid (EP771879 A, EP0952221 A, EP1078989 A).

Succinate dehydrogenase (SDH) is an enzyme which catalyzes the reaction of converting succinic acid to fumaric acid, and it was reported that a coryneform bacterium deficient in the gene of this enzyme produced a small amount of L-glutamic acid (EP1106684 A).

Furthermore, although a succinate dehydrogenase-deficient strain is also known for *Escherichia coli* belonging to the enterobacteria (J. Gen. Microbiol., 1978 July; 107 (1): 1-13), the relationship between succinate dehydrogenase deficiency and L-glutamic acid production has not been previously reported.

Furthermore, it is known that if α-ketoglutarate dehydrogenase is deleted in an *Escherichia coli* strain, the strain becomes succinic acid auxotrophic, but the double deficiency of SDH and α-ketoglutarate dehydrogenase causes the strain to recover from the succinic acid auxotrophy (J. Gen. Microbiol., 1978 July; 107 (1): 1-13). However, the effect of the double deficiency of α-ketoglutarate dehydrogenase and succinate dehydrogenase on production of an L-amino acid such as L-glutamic acid is not known.

SUMMARY OF THE INVENTION

An aspect of the present invention is to provide a bacterium that can be capable of efficiently producing an L-amino acid, and to provide a method of efficiently producing an L-amino acid using the bacterium.

It has been found that productivity of L-amino acid such as L-glutamic acid in a bacterium can be improved by modifying the bacterium so that succinate dehydrogenase activity and α-ketoglutarate dehydrogenase activity are decreased.

It is an aspect of the present invention to provide a method for producing an L-amino acid, the method comprising culturing in a medium a microorganism which has an L-amino acid producing ability and has been modified so that succinate dehydrogenase activity and α-ketoglutarate dehydrogenase activity are decreased to produce and accumulate an L-amino acid in the medium or cells of the microorganism, and collecting the L-amino acid from the medium or cells.

It is a further aspect of the present invention to provide the aforementioned method, wherein the succinate dehydrogenase activity or the α-ketoglutarate dehydrogenase activity can be decreased by reducing expression of a gene encoding succinate dehydrogenase or α-ketoglutarate dehydrogenase or disrupting the gene.

It is a further aspect of the present invention to provide the aforementioned method, wherein the gene encoding succinate dehydrogenase is selected from the group consisting of the sdhA gene, the sdhB gene, the sdhC gene, the sdhD gene, and combinations thereof.

It is a further aspect of the present invention to provide the aforementioned method, wherein the gene encoding α-ketoglutarate dehydrogenase is selected from the group consisting of the sucA gene, the odhA gene, the sucB gene, and combinations thereof.

It is a further aspect of the present invention to provide the aforementioned method, wherein the microorganism is a bacterium belonging to the family Enterobacteriaceae or a coryneform bacterium.

It is a further aspect of the present invention to provide the aforementioned method, wherein the L-amino acid is L-glutamic acid, or an L-amino acid which is biosynthesized via L-glutamic acid as a precursor.

It is a further aspect of the present invention to provide the aforementioned method, wherein the L-amino acid is selected from the group consisting of L-arginine, L-proline, L-ornithine, L-citrulline, and L-glutamine.

DETAILED DESCRIPTION OF EXEMPLARY EMBODIMENTS

Figure 1:
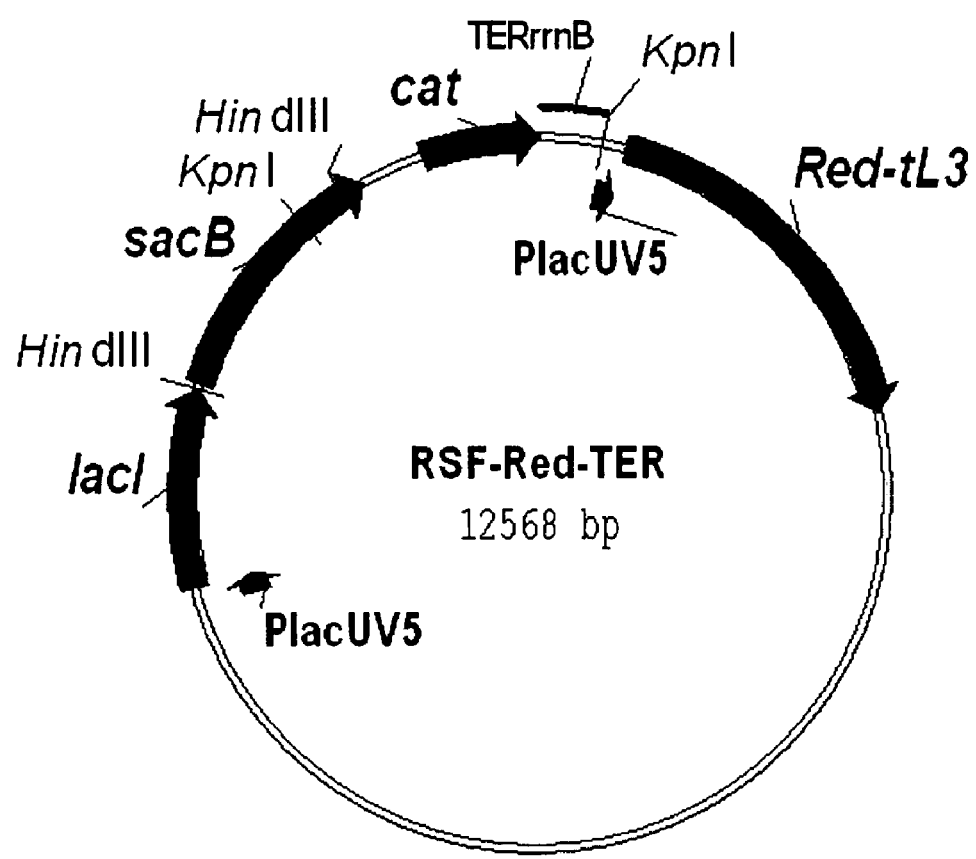
FIG. 1 shows the structure of the helper plasmid RSF-Red-TER.

Hereafter, the present invention will be explained in detail.
<1> Microorganism

Exemplary methods of the present invention include a method for producing an L-amino acid, which utilizes a microorganism which has an L-amino acid producing ability and which has been modified so that succinate dehydrogenase activity and α-ketoglutarate dehydrogenase activity are decreased.

Exemplary microorganisms used for the present invention can be obtained by modifying a microorganism which has an L-amino acid producing ability used as a parent strain so that succinate dehydrogenase and α-ketoglutarate dehydrogenase activity of the microorganism is decreased. The microorganism can also be obtained by imparting an L-amino acid producing ability to or enhancing an L-amino acid producing ability of a microorganism modified so that succinate dehydrogenase and α-ketoglutarate dehydrogenase activity of the microorganism is decreased.

The microorganism may inherently have an ability to produce an L-amino acid, or the ability may be imparted by breeding using a mutation method, a recombinant DNA technique or the like.

The words "ability to produce L-amino acid" refers to an ability to produce L-amino acid to such a degree that L-amino acid can be collected from the medium or cells when microorganism is cultured in the medium. For example, it means that the microorganism exhibits an ability to produce L-amino acid in an amount that is larger than is produced by a wild-type or unmodified strain of the microorganism cultured under the same conditions.

Examples of the L-amino acid can include L-lysine, L-glutamic acid, L-threonine, L-valine, L-leucine, L-isoleucine, L-serine, L-asparaginic acid, L-asparagine, L-glutamine, L-arginine, L-cysteine (cystine), L-methionine, L-phenylalanine, L-tryptophan, L-tyrosine, L-glycine, L-alanine, L-proline, L-ornithine, L-citrulline, L-homoserine and so forth. L-glutamic acid or L-amino acid of which precursor is L-glutamic acid or L-glutamine is preferred. Among these, L-glutamic acid, L-glutamine, L-proline, L-arginine, L-ornithine and L-citrulline are preferred.

Exemplary microorganisms used for the present invention can include, but are not limited to, bacteria belonging to Enterobacteriaceae such as those of genera *Escherichia*, *Pantoea*, and *Enterobacter*, coryneform bacteria such as *Corynebacterium glutamicum* and *Brevibacterium lactofermentum*, and *Bacillus* bacteria such as *Bacillus subtilis*.

Coryneform bacteria can include those bacteria having been hitherto classified into the genus *Brevibacterium*, but classified into the genus *Corynebacterium* at present (Int. J. Syst. Bacteriol., 41, 255 (1991)), and can include bacteria belonging to the genus *Brevibacterium* closely relative to the genus *Corynebacterium*. Examples of such coryneform bacteria are listed below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

Specific examples of the bacteria include the followings.
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067
*Brevibacterium immariophilum* ATCC 14068
*Brevibacterium lactofermentum* ATCC 13869 (*Corynebacterium glutamicum* ATCC 13869)
*Brevibacterium roseum* ATCC 13825
*Brevibacterium saccharolyticum* ATCC 14066
*Brevibacterium thiogenitalis* ATCC 19240
*Corynebacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

These strains are available from the American Type Culture Collection (ATCC) (Address: P.O. Box 1549, Manassas, Va. 20108, 1, United States of America). That is, registration numbers are given to each of the strains, and the strains can be ordered using these registration numbers. AJ12340 strain was deposited on Oct. 27, 1987 in National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan), as an accession number of FERM BP-1539 based on the Budapest Treaty.

Exemplary microorganisms belonging to Enterobacteriaceae used for the present invention can include, but are not limited to, bacteria belonging to the genera *Escherichia, Enterobacter, Pantoea, Klebsiella, Serratia, Erwinia, Salmonella, Morganella* or the like and having an L-amino acid producing ability. Specifically, bacteria belonging to the family Enterobacteriaceae according to the classification shown in NCBI (National Center for Biotechnology Information) database (http://www.ncbi.nlm.nih.gov/htbin-post/Taxonomy/wgetorg?mode=Tree&id=1236&lvl=3&kee p=1&srchmode=1&unlock) can be used. Among the bacteria of the family Enterobacteriaceae, bacteria belonging to the genus *Escherichia, Enterobacter*, or *Pantoea* can be used as the parent strain.

*Escherichia* bacteria which can be used as the parent strain can include, but are not limited to, *Escherichia* bacteria reported by Neidhardt et al. (Neidhardt, F. C. et al., *Escherichia coli* and *Salmonella Typhimurium*, American Society for Microbiology, Washington D.C., 1029 table 1), such as *Escherichia coli*. Specific examples of *Escherichia coli* include *Escherichia coli* W3110 strain (ATCC 27325), and MG1655 strain (ATCC 47076), which is derived from the wild-type (prototype) *Escherichia coli* K12 strain, and the like.

In particular, *Pantoea* bacteria, *Erwinia* bacteria and *Enterobacter* bacteria are classified as γ-proteobacteria, and they are taxonomically very close to one another (J. Gen. Appl. Microbiol., December 1997, 43(6), 355-361; International Journal of Systematic Bacteriology, October 1997, pp. 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39(3). p. 337-345). Furthermore, some bacteria belonging to the genus *Erwinia* were re-classified as *Pantoea ananas* or *Pantoea stewartii* (refer to International Journal of Systematic Bacteriology, January 1993, 43(1), pp. 162-173).

Examples of the *Enterobacter* bacteria can include *Enterobacter agglomerans, Enterobacter aerogenes*, and the like. Specifically, the strains exemplified in EP952221A can be used. A typical strain of the genus *Enterobacter* is *Enterobacter agglomerans* ATCC 12287.

Typical strains of the *Pantoea* bacteria can include *Pantoea ananatis, Pantoea stewartii, Pantoea agglomerans*, and *Pantoea citrea*. Specific examples can include the following strains:

*Pantoea ananatis* AJ13355 (FERM BP-6614, EP0952221A)

*Pantoea ananatis* AJ13356 (FERM BP-6615, EP0952221A)

Although these strains are described as *Enterobacter agglomerans* in EP0952221A, they are currently classified as *Pantoea ananatis* on the basis of nucleotide sequence analysis of 16S rRNA etc., as described above.

Examples of the *Erwinia* bacteria can include *Erwinia amylovora* and *Erwinia carotovora*, and examples of the *Klebsiella* bacteria can include *Klebsiella planticola*. Specific examples can include the following strains:

*Erwinia amylovora* ATCC 15580
*Erwinia carotovora* ATCC 15713
*Klebsiella planticola* AJ13399 (FERM BP-6600, EP955368A)
*Klebsiella planticola* AJ13410 (FERM BP-6617, EP955368A).

<1-1> Impartation or Enhancement of L-Amino Acid-Producing Ability

Hereinafter, methods for imparting an L-amino acid-producing ability to such microorganisms as described above, or methods for enhancing an L-amino acid-producing ability of such microorganisms as described above, are described.

To impart the ability to produce an L-amino acid, methods conventionally employed in the breeding of the coryneform bacteria or bacteria of the genus *Escherichia* (see "Amino Acid Fermentation", Gakkai Shuppan Center (Ltd.), 1st Edition, published May 30, 1986, pp. 77-100) can be applied. Such methods include acquisition of an auxotrophic mutant, an analogue-resistant strain, or a metabolic regulation mutant, or construction of a recombinant strain having enhanced expression of an L-amino acid biosynthesis enzyme. In the breeding of L-amino acid-producing bacteria, one or two or more properties, such as auxotrophic mutation, analogue resistance, or metabolic regulation mutation can be imparted. The expression of one or two or more L-amino acid biosynthesis enzymes can be enhanced. Furthermore, the impartation of properties such as auxotrophic mutation, analogue resistance, or metabolic regulation mutation may be combined with the enhancement of biosynthesis enzymes.

An auxotrophic mutant strain, L-amino acid analogue-resistant strain, or metabolic regulation mutant strain with an ability to produce an L-amino acid can be obtained by subjecting a parent strain or wild-type strain to a conventional mutatagenesis, such as exposure to X-rays or UV irradiation, or treatment with a mutagen such as N-methyl-N'-nitro-N-nitrosoguanidine, etc., and then selecting those which exhibit an autotrophy, analogue resistance, or metabolic regulation mutation and which also have the ability to produce an L-amino acid from the obtained mutant strains. An L-amino acid-producing bacterium can also be obtained by enhancing an enzymatic activity of L-amino acid biosynthesis enzyme by gene recombination.

Methods for imparting an L-amino acid-producing ability, and microorganisms to which an L-amino acid producing ability is imparted will be exemplified below.

Examples of methods for impartation or enhancement of L-glutamic acid-producing ability by breeding can include modifying one or more genes encoding an L-glutamic acid biosynthetic enzyme so that expression of these genes is enhanced. Examples of such genes can include, but are not limited to, genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase, pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pjkA, pjkB), glucose phosphate isomerase (pgi), methyl citrate synthase (prpC), and the like. The abbreviations in parentheses represent the gene names (the same shall apply to the same occasions hereafter).

Expression of these genes can be increased or enhanced by introduction of an amplification plasmid obtained by introducing a DNA fragment containing any of these genes into an appropriate plasmid such as a plasmid vector containing at least a gene responsible for replication of the plasmid in a microorganism. Other methods of increasing gene expression include increasing the copy number of these genes on the bacterial chromosome by conjugation, gene transfer, etc., or introducing a mutation into the promoter region of these genes (refer to International Patent Publication WO95/34672).

When a gene is introduced into the aforementioned plasmid for amplification or chromosome, the promoter for expressing the gene can be any promoter including the native promoter for the gene to be amplified and a modified promoter, so long as it functions in the chosen coryneform bacteria. The amount of gene expression can be controlled by choosing a suitable promoter or moving −35 or −10 region closer to consensus sequence. Examples of coryneform bacteria which have been modified to enhance expression of the citrate synthase gene, isocitrate dehydrogenase gene, pyruvate dehydrogenase gene, and/or glutamate dehydrogenase gene are described in International Patent Publication WO00/18935 and EP1010755A.

Moreover, the L-glutamic acid producing ability can also be imparted by reducing or deleting the activity of an enzyme that catalyzes a reaction which branches off from the L-glutamic acid biosynthetic pathway and produces a compound other than L-glutamic acid. Examples of enzymes that catalyze a reaction which branches off from the L-glutamic acid biosynthetic pathway and produces a compound other than L-glutamic acid can include isocitrate lyase, acetohydroxy acid synthase, acetolactate synthase, formate acetyltransferase, lactate dehydrogenase, glutamate decarboxylase, 1-pyrroline-5-carboxylate dehydrogenase, acetyl-CoA hydrase (International Patent Publication WO2006/057450), and the like.

Activities of the enzymes described above can be decreased or deleted by a method similar to the methods for decreasing or deleting the succinate dehydrogenase activity or α-ketoglutarate dehydrogenase activity described later.

Moreover, L-glutamic acid-producing ability can also be imparted to a coryneform bacterium by amplifying the yggB gene (NCgl 1221; NP_600492. Reports small-conductance . . . [gi: 19552490]) or by introducing a mutant yggB gene containing a mutation in the coding region thereof (WO2006/070944).

Examples of methods to enhance L-glutamic acid-producing ability can include introducing genes encoding D-xylulose-5-phosphate phosphoketolase and/or fructose-6-phosphate phosphoketolase (these are collectively called phosphoketolase). Examples of microorganisms which have enhanced activity of phosphoketolase include the following microorganisms (WO2006/016705):

*Brevibacterium lactofermentum* ATCC 13869ΔsucA (pVK9-xfp)

*Brevibacterium lactofermentum* ATCC 13869ΔsucA (pVK9-PS2_xpkA)

L-Glutamic acid-producing ability can also be imparted by enhancing the 6-phosphogluconate dehydratase activity, the 2-keto-3-deoxy-6-phosphogluconate aldolase activity, or both. Examples of a microorganism of which 6-phosphogluconate dehydratase activity and the 2-keto-3-deoxy-6-phosphogluconate aldolase are increased include the microorganism disclosed in Japanese Patent Laid-open No. 2003-274988. Furthermore, L-glutamic acid-producing ability can also be imparted by amplifying the yhfK gene, which is an L-glutamic acid secretion gene (WO2005/085419).

As an L-glutamic acid-producing microorganism which can be used for the present invention, a microorganism having an ability to accumulate L-glutamic acid in a liquid medium in an amount exceeding the saturation concentration of L-glutamic acid when it is cultured under acidic conditions (henceforth also referred to as an L-glutamic acid accumulation ability under acidic conditions) can be used. For example, by obtaining a strain of which resistance to L-glutamic acid in a low pH environment is improved according to the method described in EP1078989A, the ability to accumulate L-glutamic acid in an amount exceeding the saturation concentration can be imparted.

Specific examples of the microorganism originally having the L-glutamic acid accumulation ability under acidic conditions can include the *Pantoea ananatis* AJ13355 strain (FERM BP-6614), AJ13356 strain (FERM BP-6615), AJ13601 strain (FERM BP-7207) (for these, refer to EP0952221A), SC17sucA strain, SC17sucA/RSFCPG+pSTVCB strain, NP106 strain, NA1 strain, and the like.

The *Pantoea ananatis* AJ13355 strain was isolated from soil in Iwata-shi, Shizuoka, Japan as a strain that can proliferate in a medium containing L-glutamic acid and a carbon source at low pH. The AJ13356 strain was obtained by deleting the αKGDH-E1 subunit gene (sucA) of the AJ13355 strain.

*Pantoea ananatis* AJ13355 and AJ13356 stains were deposited on Feb. 19, 1998 in National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan), as accession numbers of FERM P-16644 and FERM P-16645 respectively, the original deposit was converted to an international deposit based on the Budapest Treaty on Jan. 11, 1999, and deposited as accession numbers of FERM BP-6614 and FERM BP-6615, respectively. These strains were identified when they were isolated, and deposited as *Enterobacter agglomerans* and deposited as *Enterobacter agglomerans* AJ13354 and AJ13355 strains, but these strains have been reclassified as *Pantoea ananatis* based on an analysis of the nucleotide sequence of 16S rRNA (see below examples). Moreover, although the AJ13601 strain described below is also deposited at the depository as *Enterobacter agglomerans*, it is described as *Pantoea ananatis* in this specification. The *Pantoea ananatis* AJ13601 stain was deposited on Aug. 18, 1999 in National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan), as an accession number of FERM P-17516, and the original deposit was converted to an international deposit based on Budapest Treaty on Jul. 6, 2000, with an accession number of FERM BP-7207.

Furthermore, examples of L-glutamic acid producing *Pantoea ananatis* strain include bacteria belonging to the genus *Pantoea* in which α-ketoglutarate dehydrogenase (α-KGDH) activity is eliminated or reduced. Examples of such strains include the AJ13356 strain, and the SC17sucA strain (U.S. Pat. No. 6,596,517) which is a sucA gene-deficient strain derived from the SC17 strain selected as a low phlegm production mutant strain from the AJ13355 strain. The SC17sucA strain was assigned a private number of AJ417, deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Feb. 26, 2004, and assigned an accession number of FERM BP-08646.

The SC17sucA/RSFCPG+pSTVCB strain described above was obtained by introducing into the SC17sucA strain the plasmid RSFCPG containing the citrate synthase gene (gltA), phosphoenolpyruvate carboxylase gene (ppsA) and the glutamate dehydrogenase gene (gdhA) derived from *Escherichia coli*, and the plasmid pSTVCB containing the citrate synthase gene (gltA) derived from *Brevibacterium lactofermentum*. The AJ13601 strain was selected from the SC17sucA/RSFCPG+pSTVCB strain as having resistance to L-glutamic acid of a high concentration at a low pH. Furthermore, the NP106 strain corresponds to the AJ13601 strain in which the plasmid RSFCPG+pSTVCB are eliminated as described in the examples.

As other methods for imparting or enhancing L-glutamic acid producing ability, there can be mentioned methods of imparting resistance to an organic acid analogue, respiratory inhibitor or the like and methods of imparting sensitivity to a cell wall synthesis inhibitor. Examples can include, for example, imparting monofluoroacetic acid resistance (Japanese Patent Laid-open No. 50-113209), imparting adenine resistance or thymine resistance (Japanese Patent Laid-open No. 57-065198), attenuating urease (Japanese Patent Laid-open No. 52-038088), imparting malonic acid resistance (Japanese Patent Laid-open No. 52-038088), imparting resistance to benzopyrons or naphthoquinones (Japanese Patent Laid-open No. 56-1889), imparting HOQNO resistance (Japanese Patent Laid-open No. 56-140895), imparting α-ketomalonic acid resistance (Japanese Patent Laid-open No. 57-2689), imparting guanidine resistance (Japanese Patent Laid-open No. 56-35981), imparting sensitivity to penicillin (Japanese Patent Laid-open No. 4-88994), and the like.

Specific examples of such resistant bacteria include the following strains.

*Brevibacterium flavum* AJ3949 (FERM BP-2632, Japanese Patent Laid-open No. 50-113209)

*Corynebacterium glutamicum* AJ11628 (FERM P-5736, Japanese Patent Laid-open No. 57-065198)

*Brevibacterium flavum* AJ11355 (FERM P-5007, Japanese Patent Laid-open No. 56-1889)

*Corynebacterium glutamicum* AJ11368 (FERM P-5020, Japanese Patent Laid-open No. 56-1889)

*Brevibacterium flavum* AJ11217 (FERM P-4318, Japanese Patent Laid-open No. 57-2689)

*Corynebacterium glutamicum* AJ11218 (FERM P-4319, Japanese Patent Laid-open No. 57-2689)

*Brevibacterium flavum* AJ11564 (FERM BP-5472, Japanese Patent Laid-open No. 56-140895)

*Brevibacterium flavum* AJ11439 (FERM BP-5136, Japanese Patent Laid-open No. 56-35981)

*Corynebacterium glutamicum* H7684 (FERM BP-3004, Japanese Patent Laid-open No. 04-88994)

*Brevibacterium lactofermentum* AJ11426 (FERM P-5123, Japanese Patent Laid-open No. 56-048890)

*Corynebacterium glutamicum* AJ11440 (FERM P-5137, Japanese Patent Laid-open No. 56-048890)

*Brevibacterium lactofermentum* AJ11796 (FERM P-6402, Japanese Patent Laid-open No. 58-158192)

Examples of microorganisms having L-glutamine-producing ability can include bacteria in which glutamate dehydrogenase activity is enhanced, bacteria in which glutamine synthetase (glnA) activity is enhanced, and bacteria in which glutaminase gene is disrupted (European Patent Application Laid-open Nos. 1229121 and 1424398). Enhancement of the glutamine synthetase activity can also be attained by disrupting the glutamine adenylyltransferase (glnE) or disrupting the PII control protein (glnB). Furthermore, a strain which belongs to the genus *Escherichia* and has a mutant glutamine synthetase in which the tyrosine residue at position 397 is replaced with another amino acid residue can also be exemplified as an L-glutamine producing bacterium (U.S. Patent Application Publication No. 2003/0148474).

Other methods for imparting or enhancing L-glutamine-producing ability can be the method of imparting 6-diazo-5-oxo-norleucine resistance (Japanese Patent Laid-open No. 3-232497), imparting purine analogue resistance and methionine sulfoxide resistance (Japanese Patent Laid-open No. 61-202694), imparting α-ketomaleic acid resistance (Japanese Patent Laid-open No. 56-151495), and the like. Specific examples of coryneform bacteria having L-glutamine-producing ability can include the following strains.

*Brevibacterium flavum* AJ11573 (FERM P-5492, Japanese Patent Laid-open No. 56-161495)

*Brevibacterium flavum* AJ11576 (FERM BP-10381, Japanese Patent Laid-open No. 56-161495)

*Brevibacterium flavum* AJ12212 (FERM P-8123, Japanese Patent Laid-open No. 61-202694)

Examples of microorganisms having L-proline-producing ability can include, for example, bacteria having γ-glutamyl kinase which is desensitized to feedback inhibition by L-proline and bacteria in which L-proline decomposition system is attenuated. The method of modifying bacteria using a DNA encoding γ-glutamyl kinase desensitized to feedback inhibition by L-proline is disclosed in Dandekar, A. M., Uratsu S. L., J. Bacteriol., 170, 12:5943-5 (1988). Furthermore, examples of the method for obtaining a bacterium of in L-proline decomposition system is attenuated can include, for example, a method of introducing a mutation into a proline dehydrogenase gene for reducing its enzymatic activity. Example of bacteria having L-proline-producing ability can include the *Escherichia coli* NRRL B-12403 and NRRL B-12404 strains (British Patent No. 2075056), *Escherichia coli* VKPM B-8012 strain (U.S. Patent Application Publication No. 2002/0058315), and strains having the mutant plasmid disclosed in German Patent No. 3127361 or the mutant plasmid disclosed in the reference of Bloom F. R. et al. (The 15th Miami Winter Symposium, 1983, p. 34).

Furthermore, examples of microorganisms having L-proline-producing ability also can include the *Escherichia coli* 702 strain (VKPMB-8011), which is a 3,4-dehydroxyproline and azetidine-2-carboxylate resistant strain, 702ilvA strain (VKPMB-8012 strain), which is an ilvA-deficient strain of the 702 strain, *E. coli* strains in which activity of protein encoded by the b2682, b2683, b1242 or b3434 gene is enhanced (Japanese Patent Laid-open No. 2002-300874), and the like.

Examples of L-proline-producing strains of coryneform bacteria can include the DL-3,4-dehydroproline resistant strain (FERM BP-1219, U.S. Pat. No. 4,224,409), the strains in which citrate synthetase activity increases 1.4 times or more as compared to parent strains thereof (FERM P-5332, FERM P-5333, FERM P-5342, FERMP-5343, Japanese Patent No. 1426823), and the strain to which acetic acid auxotrophy is imparted (FERM P-5931).

Examples of microorganism having L-leucine-producing ability can include *Escherichia coli* strains resistant to 4-aza-leucine or 5,5,5-trifluoroleucine such as H-9068 (ATCC 21530), H-9070 (FERM BP-4704) and H-9072 (FERM BP-4706) (U.S. Pat. No. 5,744,331), *Escherichia coli* strains having isopropyl malate synthase desensitized to feedback inhibition by L-leucine (European Patent No. 1067191), *Escherichia coli* strains resistant to β-2-thienylalanine and β-hydroxyleucine such as AJ11478 (U.S. Pat. No. 5,763, 231), *Escherichia coli* 57 (VKPM B-7386, Russian Patent No. 2140450), and the like.

Examples of L-leucine-producing strains of coryneform bacteria can include 2-thiazolealanine and β-hydroxyleucine resistant strain (Japanese Patent Laid-open No. 8-266295), valine analogue resistant strain (Japanese Patent Laid-open No. 63-248392), valine auxotrophic strain (Japanese Patent Publication No. 38-4395), S-(2-aminoethyl)-L-cysteine (AEC) resistant strain (Japanese Patent Publication No. 51-37347), and phenylalanine, valine and isoleucine auxotrophic strain (Japanese Patent Publication No. 54-36233).

Examples of microorganism having L-cysteine-producing ability can include *Escherichia coli* JM15 strain which is transformed with a cysE allele encoding serine acetyltransferases desensitized to feedback inhibition (U.S. Pat. No. 6,218,168), *Escherichia coli* W3110 strain having over-expressed genes which encode proteins suitable for excreting substances toxic for cells (U.S. Pat. No. 5,972,663), *Escherichia coli* strain having lowered cysteine desulfhydrase activity (Japanese Patent Laid-open No. 11-155571), *Escherichia coli* W3110 strain in which a transcriptional activator for cysteine regulon encoded by the cysB gene is amplified (WO01/27307), and the like.

Examples of microorganisms having L-isoleucine-producing ability include, for example, mutants strains of the genus *Escherichia* having resistance to 6-dimethylaminopurine (Japanese Patent Laid-open No. 5-304969), mutants having resistance to L-isoleucine hydroxamate, thiaisoleucine, DL-ethionine or arginine hydroxamate (Japanese Patent Laid-open No. 5-130882), recombinant strains in which threonine deaminase gene and acetohydroxate synthase gene are amplified (Japanese Patent Laid-open Nos. 2-458, 2-42988 and 8-47397), and so forth.

Examples of L-isoleucine-producing strains of coryneform bacteria can include the coryneform bacterium in which the brnE gene encoding a branched chain amino acid excretion protein is amplified (Japanese Patent Laid-open No. 2001-169788), coryneform bacteria to which L-isoleucine-producing ability is imparted by protoplast fusion with a L-lysine-producing bacterium (Japanese Patent Laid-open No. 62-74293), homoserine dehydrogenase-enhanced coryneform bacteria (Japanese Patent Laid-open No. 62-91193), threonine hydroxamate resistant strains (Japanese Patent Laid-open No. 62-195293), α-ketomalonic acid resistant strains (Japanese Patent Laid-open No. 61-15695), and the methyllysine resistant strains (Japanese Patent Laid-open No. 61-15696).

L-Valine-producing ability may be imparted by increasing the activities of L-valine synthetic enzymes encoded by the ilvGMEDA operon, in particular, activity of acetohydroxylate synthase encoded by the ilvG gene (Japanese Patent Publication No. 02-748418). Such L-valine synthetic enzymes can be desensitized to the feedback inhibition by L-valine. L-Valine-producing ability can also be imparted by decreasing expression of acetolactate synthase III gene (ilvIH gene).

Moreover, L-valine-producing ability can also be imparted by imparting amino acid analogue-resistance to a bacterium. Examples of such bacteria can include mutant strains which are auxotrophic to L-isoleucine and L-methionine and resistant to D-ribose, purine nucleoside, or pyrimidine ribonucleoside (FERM P-1841 and P-5556; Japanese Patent Laid-open No. 53-025034), and a mutant strain that is resistant to polyketide (FERM P-9325, Japanese Patent No. 1934507).

Examples of L-valine-producing bacteria also can include strains with aminoacyl t-RNA synthetase mutants (U.S. Pat. No. 5,658,766). For example, *E. coli* VL1970, which has a mutation in the ileS gene encoding isoleucine tRNA synthetase, can be used. *E. coli* VL1970 was deposited at the Russian National Collection of Industrial Microorganisms (VKPM) (1 Dorozhny proezd., 1 Moscow 117545, Russia) on Jun. 24, 1988 under an accession number VKPM B-4411.

Furthermore, mutants requiring lipoic acid for growth and/or lacking H$^+$-ATPase (WO96/06926) can also be used as parent strains.

Examples of L-valine-producing strain of coryneform bacteria can include, for example, a strain modified so that expression of a gene encoding an enzyme which participates in the L-valine biosynthesis is enhanced. Examples of the enzyme which participates in the L-valine biosynthesis can include, for example, those encoded by the ilvBNC operon, i.e., such as acetohydroxy acid synthase encoded by ilvBN and isomeroreductase (ilvC) (WO00/50624). In addition, since the ilvBNC operon is under the control of the operon by L-valine and/or L-isoleucine and/or L-leucine, the attenuation can be eliminated in order to eliminate the expression suppression by L-valine to be produced.

Examples of microorganisms having an L-alanine-producing ability can include coryneform bacteria deficient in the H$^+$-ATPase activity (Appl. Microbiol. Biotechnol., 2001 November; 57(4): 534-40), coryneform bacteria in which aspartate β-decarboxylase gene is amplified (Japanese Patent Laid-open No. 07-163383), and the like.

Examples of microorganisms having an L-arginine-producing ability can include, *Escherichia coli* mutant strains which have resistance to α-methylmethionine, p-fluorophenylalanine, D-arginine, arginine hydroxamate, AEC (S-(2-aminoethyl)-cysteine), α-methylserine, β-2-thienylalanine, or sulfaguanidine (refer to Japanese Patent Laid-open No. 56-106598). The *Escherichia coli* 237 strain which is an L-arginine producing strain which harbors highly active N-acetylglutamate synthase having a mutation for resistance to feedback inhibition by L-arginine (Russian Patent Application No. 2000117677) can also be used as an L-arginine-producing bacterium. The 237 strain was deposited in the Russian National Collection of Industrial Microorganisms (VKPM) (GNII Genetika) on Apr. 10, 2000 under an accession number of VKPM B-7925, and the original deposit was converted to an international deposit based on the Budapest Treaty on May 18, 2001. The *Escherichia coli* 382 strain, which is a derivative of the 237 strain and is an L-arginine-producing strain having improved ability to assimilate acetic acid (Japanese Patent Laid-open No. 2002-017342), can also be used. The *Escherichia coli* 382 strain was deposited in the Russian National Collection of Industrial Microorganisms (VKPM) on Apr. 10, 2000 under an accession number of VKPM B-7926.

As microorganisms having an L-arginine-producing ability, strains in which the expression of one or more genes encoding an L-arginine biosynthetic enzyme is increased can also be used. Examples of the L-arginine biosynthetic enzyme can include one or more enzymes selected from N-acetylglutaminate synthetase (argA), N-acetylglutamyl phosphate reductase (argC), ornithine acetyl transferase (argJ), N-acetylglutamate kinase (argB), acetylornithine transaminase (argD), acetylornithine deacetylase (argE), ornithine carbamoyl transferase (argF), argininosuccinic acid synthetase (argG), argininosuccinic acid lyase (argH), and carbamoyl phosphate synthetase (carAB). A mutant N-acetylglutamate synthase gene (argA) encoding the enzyme in which the amino acid sequence corresponding to positions 15 to 19 of a wild-type enzyme is replaced and the feedback inhibition by L-arginine is thereby canceled (EP1170361A) also can be used.

Although L-arginine-producing coryneform bacteria are not particularly limited so long as they have an L-arginine-producing ability, examples can include wild-type strains of coryneform bacteria; coryneform bacteria resistant to certain agents including sulfa drugs, 2-thiazolealanine, α-amino-β-hydroxyvaleric acid and so forth; coryneform bacteria exhibiting auxotrophy for L-histidine, L-proline, L-threonine, L-isoleucine, L-methionine or L-tryptophan in addition to the resistance to 2-thiazolealanine (Japanese Patent Laid-open No. 54-4409); coryneform bacteria resistant to ketomalonic acid, fluoromalonic acid or monofluoroacetic acid (Japanese Patent Laid-open No. 57-18989); coryneform bacteria resistant to argininol (Japanese Patent Laid-open No. 62-24075); coryneform bacteria resistant to X-guanidine (X represents a derivative of fatty acid or aliphatic chain, Japanese Patent Laid-open No. 2-186995), and the like.

A coryneform bacterium having L-arginine-producing ability can be bred as a strain resistant to 5-azauracil, 6-azauracil, 2-thiouracil, 5-fluorouracil, 5-bromouracil, 5-azacytosine, 6-azacytosine and the like; a strain resistant to arginine hydroxamate and 2-thiouracil; strain resistant to arginine hydroxamate and 6-azauracil (Japanese Patent Laid-open No. 49-126819); a strain resistant to a histidine analogue or tryptophan analogue (Japanese Patent Laid-open No. 52-114092); a strain auxotrophic for at least one of methionine, histidine, threonine, proline, isoleucine, lysine, adenine, guanine and uracil (or uracil precursor) (Japanese Patent Laid-open No. 52-99289); a strain resistant to arginine hydroxamate (Japanese Patent Publication No. 51-6754); a strain auxotrophic for succinic acid or resistant to a nucleic acid base analogue (Japanese Patent Laid-open No. 58-9692); a strain deficient in arginine decomposition ability, resistant to an arginine antagonist and canavanine and auxotrophic for lysine (Japanese Patent Laid-open No. 52-8729); a strain resistant to arginine, arginine hydroxamate, homoarginine, D-arginine and canavanine, or resistant to arginine hydroxamate and 6-azauracil (Japanese Patent Laid-open No. 53-143288); a strain resistant to canavanine (Japanese Patent Laid-open No. 53-3586); or the like.

Specific examples of coryneform bacteria having L-arginine-producing ability can include the following strains.

*Brevibacterium flavum* AJ11169 (FERM P-4161)
*Brevibacterium lactofermentum* AJ12092 (FERM P-7273)
*Brevibacterium flavum* AJ11336 (FERM P-4939)
*Brevibacterium flavum* AJ11345 (FERM P-4948)
*Brevibacterium lactofermentum* AJ12430 (FERM BP-2228)

Furthermore, a strain deficient in ArgR, which is an arginine repressor (U.S. Published Patent Application No. 2002/0045223) and a strain in which glutamine synthetase activity is increased (U.S. Published Patent Application No. 2005/0014236) can also be used.

L-Citrulline and L-ornithine share common biosynthetic pathways with L-arginine, and the ability to produce L-citrulline and L-ornithine can be imparted by increasing the enzymatic activities of N-acetylglutamate synthase (argA), N-acetylglutamylphosphate reductase (argC), ornithine acetyltransferase (argJ), N-acetylglutamate kinase (argB), acetylornithine transaminase (argD), and acetylornithine deacetylase (argE) (WO2006/35831).

Examples of microorganisms having an L-lysine-producing ability can include L-lysine analogue resistant strains and metabolic regulation mutants having L-lysine-producing ability. Specific examples include the *Escherichia coli* AJ11442 strain (FERM BP-1543, NRRL B-12185, see Japanese Patent Laid-open No. 56-18596 and U.S. Pat. No. 4,346,170) and the *Escherichia coli* VL611 strain (Japanese Patent Laid-open No. 2000-189180). The WC196 strain (WO96/17930) can also be used as an L-lysine-producing *Escherichia coli* bacterium. This bacterial strain was bred from conferring AEC (S-(2-aminoethyl)-cysteine) resistance to the W3110 strain, which is derived from *Escherichia coli* K-12. This strain was named *Escherichia coli* AJ13069 and was deposited on Dec. 6, 1994 in National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan), with an accession number of FERM P-14690, and the original deposit was converted to an international deposit based on Budapest Treaty on Sep. 29, 1995, with an accession number of FERM BP-5252.

Examples of L-lysine producing coryneform bacteria can include S-(2-aminoethyl)cysteine (abbreviated as "AEC" hereinafter) resistant mutant strains (*Brevibacterium lactofermentum* AJ11082 (NRRL B-11470) strain etc., refer to Japanese Patent Publication Nos. 56-1914, 56-1915, 57-14157, 57-14158, 57-30474, 58-10075, 59-4993, 61-35840, 62-24074, 62-36673, 5-11958, 7-112437 and 7-112438); mutant strains requiring an amino acid such as L-homoserine for their growth (refer to Japanese Patent Publication Nos. 48-28078 and 56-6499); mutant strains having resistance to AEC and further requiring an amino acid such as L-leucine, L-homoserine, L-proline, L-serine, L-arginine, L-alanine and L-valine (refer to U.S. Pat. Nos. 3,708,395 and 3,825,472); L-lysine producing mutant strains having resistance to DL-α-amino-ε-caprolactam, α-amino-lauryllactam, aspartic acid analogue, sulfa drug, quinoid and N-lauroylleucine; L-lysine producing mutant strains having resistance to oxaloacetate decarboxylase or a respiratory tract enzyme inhibitor (Japanese Patent Laid-open Nos. 50-53588, 50-31093, 52-102498, 53-9394, 53-86089, 55-9783, 55-9759, 56-32995, 56-39778, Japanese Patent Publication Nos. 53-43591 and 53-1833); L-lysine producing mutant strains requiring inositol or acetic acid (Japanese Patent Laid-open Nos. 55-9784 and 56-8692); L-lysine producing mutant strains that are sensitive to fluoropyruvic acid or a temperature of 34° C. or higher (Japanese Patent Laid-open Nos. 55-9783 and 53-86090); L-lysine producing mutant strains of *Brevibacterium* or *Corynebacterium* bacteria having resistance to ethylene glycol (U.S. Pat. No. 4,411,997) and so forth.

Microorganisms to which L-lysine producing ability is imparted can also be obtained by enhancing the activity of an L-lysine biosynthetic enzyme. Activity of an L-lysine biosynthetic enzyme can be enhanced by increasing the copy number of the gene encoding the L-lysine biosynthetic enzyme or by modifying an expression regulatory sequence of the gene encoding the enzyme.

Examples of genes encoding L-lysine biosynthetic enzymes include genes encoding enzymes of the diaminopimelate synthesis pathway such as the dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO96/40934 for all the foregoing genes), phosphoenolpyruvate carboxylase gene (ppc) (Japanese Patent Laid-open No. 60-87788), aspartate aminotransferase gene (aspC) (Japanese Patent Publication No. 6-102028), diaminopimelate epimerase gene (dapF) (Japanese Patent Laid-open No. 2003-135066), and aspartate semialdehyde dehydrogenease gene (asd) (WO00/61723), and genes encoding enzymes of aminoadipic acid synthesis pathway such as homoaconitate hydratase gene (Japanese Patent Laid-open No. 2000-157276).

The gene encoding aspartokinase III (lysC) can be modified so that the enzyme is desensitized to feedback inhibition by L-lysine. Such a modified lysC gene can be obtained by the method described in U.S. Pat. No. 5,932,453.

The microorganisms having L-lysine-producing ability can have reduced activity of an enzyme that catalyzes a reaction which produces a compound other than L-lysine or can be deficient in such an activity, or can have reduced activity of an enzyme that negatively acts on L-lysine production or can be deficient in such an activity. Examples of such enzymes can include homoserine dehydrogenase, lysine decarboxylase (cadA, ldcC), and malic enzyme. The strains in which activities of the enzymes are decreased or deleted are disclosed in WO95/23864, WO96/17930, WO2005/010175, and the like.

Examples of microorganisms having an L-tryptophan-producing ability can include strains in which one or more of activities of the enzymes selected from anthranilate synthase (trpE), phosphoglycerate dehydrogenase (serA), and tryptophan synthase are enhanced. The anthranilate synthase and phosphoglycerate dehydrogenase are both subject to feedback inhibition by L-tryptophan and L-serine, respectively, and therefore the enzymatic activities can be enhanced by making the microorganisms contain a desensitized type mutant enzyme. Specifically, a bacterium harboring a desensitized type enzyme can be obtained by, for example, mutating the anthranilate synthase gene and/or phosphoglycerate dehydrogenase gene so that the encoded enzymes are desensitized to the feedback inhibition and introducing the mutant genes into the bacterium. Specific examples of such a bacterium can include a transformant obtained by introducing the plasmid pGH5 (WO94/08031) which contains a mutant serA gene which has been mutated so that it encodes feedback inhibition-desensitized phosphoglycerate dehydrogenase into the *Escherichia coli* SV164 strain which has a desensitized anthranilate synthase.

L-Tryptophan-producing ability can also be imparted by introducing a recombinant DNA containing the tryptophan operon. Specific examples can include *Escherichia coli* transformed with the tryptophan operon which contains a gene encoding desensitized anthranilate synthase (Japanese Patent Laid-open Nos. 57-71397 and 62-244382, U.S. Pat. No. 4,371,614). Moreover, L-tryptophan-producing ability can also be increased or imparted by enhancing expression of a gene which encodes tryptophan synthase (trpBA) in the tryptophan operon. The tryptophan synthase includes α and β subunits, which are encoded by trpA and trpB, respectively.

L-Tryptophan-producing ability can also be imparted by deleting trpR encoding the repressor of the tryptophan operon, or introducing a mutation into trpR so that the activity of the repressor is decreased (U.S. Pat. No. 4,371,614 and WO2005/056776).

Strains in which malate synthase-isocitrate lyase-isocitrate dehydrogenasekinase/phosphatase operon (ace operon) is constitutively expressed or expression of the operon is enhanced also can be examples of L-tryptophan-producing strains. Specifically, in an exemplary embodiment according to the presently disclosed subject matter, the promoter of the ace operon is not suppressed by the repressor iclR, or the suppression by iclR is eliminated. Such strains can be obtained by disrupting the iclR gene.

A strain in which the expression of the ace operon is enhanced can be obtained by ligating a DNA comprising the ace operon to a strong promoter, and introducing it into cells using a plasmid or by homologous recombination, or by transferring it with a transposon, so that multiple copies of the DNAs are integrated into the chromosomal DNA.

Examples of microorganisms having an L-tryptophan-producing ability can further include the *Escherichia coli* AGX17 (pGX44) strain (NRRL B-12263), which is auxotrophic for L-phenylalanine and L-tyrosine, and AGX6 (pGX50) aroP strain (NRRL B-12264) which harbors plasmid pGX50 which includes the tryptophan operon (refer to U.S. Pat. No. 4,371,614 for both).

As coryneform bacteria having L-tryptophan-producing ability, *Corynebacterium glutamicum* AJ12118 which is resistant to sulfaguanidine (FERM BP-478, Japanese Patent No. 1681002), a coryneform bacterium into which the tryptophan operon is introduced (Japanese Patent Laid-open No. 63-240794), and a coryneform bacterium into which a gene encoding shikimate kinase of a coryneform bacterium is introduced (Japanese Patent Laid-open No. 01-994749) can be used.

L-Tryptophan, L-phenylalanine, and L-tyrosine are all aromatic amino acids and have a common biosynthesis pathway. Examples of the genes encoding biosynthesis enzymes for these aromatic amino acids can include deoxyarabino-heptulosonate phosphate synthase (aroG), 3-dehydroquinate synthase (aroB), shikimic acid dehydrogenase (aroE), shikimate kinase (aroL), 5-enolpyruvylshikimate-3-phosphate synthase (aroA), and chorismate synthase (aroC) (EP763127A). Therefore, by introducing multiple copies of genes encoding these enzyme into cell with a plasmid or into genome, the ability for producing an aromatic amino acid can be improved. It is known that these genes can be controlled by a tyrosine repressor (tyrR), and therefore an aromatic amino acid biosynthesis enzyme activity can also be increased by deleting the tyrR gene (see European Patent No. 763127).

Examples of microorganism having L-phenylalanine-producing ability include, but are not limited to, strains belonging to the genus *Escherichia* such as *E. coli* AJ12739 (tyrA: Tn10, tyrR) (VKPM B-8197) deficient in tyrA and tyrR, *E. coli* HW1089 (ATCC 55371) harboring a mutant pheA34 gene (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407, 952). *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB], also called AJ12604 (FERM BP-3579) also can be used (European Patent Publication No. 488-424 B1). Examples further include the strains in which yedA and yddG genes are amplified, which are L-phenylalanine-secreting genes (WO03/044192, U.S. Published Patent Applications No. 2003/0148473 and 2003/0157667).

As phenylalanine-producing strains of coryneform bacteria, the *Corynebacterium glutamicum* strains BPS-13 (FERM BP-1777), K77 (FERM BP-2062) and K78 (FERM BP-2063) in which phosphoenolpyruvate carboxylase or pyruvate kinase activity is decreased (EP331145A, Japanese Patent Laid-open No. 02-303495), tyrosine auxotrophic strain (Japanese Patent Laid-open No. 05-049489), and the like can be used.

Other examples of microorganisms having L-threonine-producing ability can include microorganisms belonging to the family Enterobacteriaceae in which one or more activities of L-threonine biosynthesis system enzymes are enhanced. Examples of genes encoding L-threonine biosynthetic enzymes can include aspartokinase III gene (lysC), aspartate semialdehyde dehydrogenase gene (asd), aspartokinase I gene (thrA), homoserine kinase gene (thrB), and threonine synthase gene (thrC) encoded by the threonine operon. The abbreviations of the gene names are indicated in the parentheses. Two or more kinds of these genes can be introduced. The genes encoding the L-threonine biosynthetic enzymes can be introduced into an *Escherichia* bacterium in which threonine decomposition is decreased. Examples of the *Escherichia* bacterium in which threonine decomposition is decreased can include, for example, the TDH6 strain which is deficient in threonine dehydrogenase activity (Japanese Patent Laid-open No. 2001-346578), and the like.

The activities of the L-threonine biosynthetic enzymes are inhibited by the endoproduct, L-threonine, and therefore L-threonine biosynthetic enzymes can be modified so as to be desensitized to feedback inhibition by L-threonine for constructing L-threonine-producing strains. The above-described thrA, thrB and thrC genes constitute a threonine operon, and the threonine operon forms an attenuator structure. Since the expression of threonine operon is inhibited by isoleucine and threonine in the culture medium and also inhibited by attenuation, the threonine operon can be modified by removing leader sequence or attenuator in the attenuation region (Lynn, S. P., Burton, W. S., Donohue, T. J., Gould, R. M., Gumport, R. I., and Gardner, J. F. J., Mol. Biol. 194:59-69 (1987); WO02/26993; WO2005/049808).

The native promoter of the threonine operon locating upstream of the threonine operon can be replaced with a non-native promoter (WO98/04715), or the threonine operon can be constructed so that expression of genes involved in the threonine synthesis is controlled by the repressor and promoter of λ-phage (European Patent No. 0593792). Furthermore, mutant *Escherichia* bacteria that are desensitized to feedback inhibition by L-threonine can be obtained by screening for strains resistant to α-amino-β-hydroxyisovaleric acid (AHV).

The thereonine operon can be modified so as to be desensitized to feedback inhibition by L-threonine in a host bacterium. Alternatively, this modified operon can be connected to a potent promoter to increase the expression of this modified operon. The copy number can be increased by amplification with a plasmid. Alternatively, the copy number can be increased by using a transposon or Mu-phage so that the operon is transferred onto a chromosome of a host bacterium.

L-Threonine-producing bacterium can also be obtained by enhancing expression of genes involved in the glycolytic pathway, TCA cycle, or respiratory chain, genes that regulate the expression of these genes, or genes involved in sugar uptake, besides the genes of L-threonine biosynthetic enzymes. Examples of these genes that can be effective for L-threonine production can include the transhydrogenase gene (pntAB) (European Patent Publication No. 733712B), phosphoenolpyruvate carboxylase gene (pepC) (WO95/06114), phosphoenolpyruvate synthase gene (pps) (European Patent Publication No. 877090B), pyruvate carboxylase gene derived from coryneform bacterium or *Bacillus* bacterium (WO99/18228, EP1092776A).

L-Threonine-producing bacterium can also be obtained by enhancing expression of a gene that imparts L-threonine resistance and/or a gene that imparts L-homoserine resistance, or by imparting L-threonine resistance and/or L-homoserine resistance to a host bacterium. Examples of the genes that impart the resistance can include the rhtA gene (Res. Microbiol. 154:123-135 (2003)), rhtB gene (EP0994190A), rhtC gene (EP1013765A), yfiK gene, and yeaS gene (EP1016710A). Methods for imparting L-threonine resistance to a host bacterium are described in EP0994190A or WO90/04636.

*Escherichia coli* VKPM B-3996 (U.S. Pat. No. 5,175,107) can also be exemplified as a microorganism having L-threonine-producing ability. The VKPM B-3996 strain was deposited on Nov. 19, 1987 in the Russian National Collection of Industrial Microorganisms (VKPM), GNII Genetika under an accession number VKPM B-3996. The VKPM B-3996 strain contains the plasmid pVIC40 (WO90/04636) which was obtained by inserting threonine biosynthetic genes (threonine operon: thrABC) into a wide host range plasmid vector pAYC32 containing the streptomycin resistance marker (Chistorerdov, A. Y., and Tsygankov, Y. D., Plasmid, 16, 161-167 (1986)). The threonine operon in pVIC40 contains a mutant thrA gene which encodes aspartokinase I-homoserine dehydrogenase I which is substantially desensitized to feedback inhibition by threonine.

The *Escherichia coli* B-5318 strain (European Patent Publication No. 0593792B) also can be exemplified as a L-threonine-producing ability-imparted bacterium. The B-5318 strain was deposited in the Russian National Collection of Industrial Microorganisms (VKPM), GNII Genetika on Nov. 19, 1987 under an accession number of VKPM B-5318. The VKPM B-5318 strain is prototrophic with regard to L-isoleucine, and harbors a recombinant plasmid DNA which contains the threonine operon, i.e., genes involved in threonine biosynthesis, deficient in the attenuator region, which is a transcription control region originally located downstream from the C1 temperature-sensitive repressor, PR-promoter, and Cro protein N-terminal sequence derived from λ phage, and is constructed so that the expression of the genes involved in the threonine biosynthesis is regulated by the repressor and promoter derived from λ phage.

In the L-amino acid producing bacterium in accordance with the presently disclosed subject matter, genes involved in sugar uptake, sugar metabolism (glycolysis system) and energy metabolism can be amplified, in addition to genes encoding inherent biosynthetic enzymes.

Examples of the genes involved in sugar metabolism can include genes encoding an enzyme in the glycolytic pathway or enzyme involved in sugar uptake, such as the glucose-6-phosphate isomerase gene (pgi, WO01/02542), phosphoenolpyruvate synthase gene (pps, EP877090A), phosphoglucomutase gene (pgm, WO03/04598), fructose bisphosphate aldolase gene (fbp, WO03/04664), pyruvate kinase gene (pykF, WO03/008609), transaldolase gene (talB, WO03/008611), fumarase gene (fum, WO01/02545), phosphoenolpyruvate synthase gene (pps, EP877090A), non-PTS sucrose uptake gene (csc, EP149911A), and sucrose-assimilating gene (scrAB operon, WO90/04636).

Examples of genes encoding enzymes involved in energy metabolism can include transhydrogenase gene (pntAB, U.S. Pat. No. 5,830,716) and cytochromoe bo type oxidase gene (cyoB, EP1070376A).

A microorganism in accordance with the presently disclosed subject matter can be a microorganism having an L-amino acid-producing ability as described above and modified so that succinate dehydrogenase activity and α-ketoglutarate dehydrogenase activity are decreased.

<1-2> Decrease of Succinate Dehydrogenase Activity and α-Ketoglutarate Dehydrogenase Activity The expression "activities of the enzymes are decreased" means that the succinate dehydrogenase activity and the α-ketoglutarate dehydrogenase activity are lower than in a non-modified strain such as wild-type strain or parent strain, which includes that the enzyme activities have completely disappeared.

The succinate dehydrogenase (henceforth also referred to as "SDH") is the enzyme of EC:1.3.99.1, which reversibly catalyzes the following reaction. In accordance with the presently disclosed subject matter, SDH activity means the activity for catalyzing the following reaction.

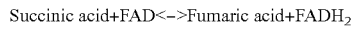

Succinic acid+FAD<->Fumaric acid+FADH$_2$

SDH can include three or four subunit structures depending on the type of microorganism, and the activity thereof can be decreased by modifying at least one of these proteins so that it does not normally function. Specifically, SDH can include the following subunits (names of genes encoding the subunits are indicated in parentheses), and the membrane anchor protein is encoded solely by sdhC or by sdhC and sdhD depending on species.

SDHA: flavoprotein subunit (sdhA)
SDHB: Fe—S protein subunit (sdhB)
SDHC: membrane anchor protein (sdhC)
SDHD: membrane anchor protein (sdhD)

Furthermore, the SDH subunit complex can have the activities of both SDH and fumarate reductase. For example, the SDH subunit complex of coryneform bacteria has the activities of both SDH and fumarate reductase (WO2005/021770).

The SDH activity can be confirmed by measuring the reduction of 2,6-dichloroindophenol (DCIP) as an indicative index. A specific method is described in Tatsuki Kurokawa and Junshi Sakamoto, Arch. Microbiol., (2005) 183:317-324.

In accordance with the presently disclosed subject matter, the genes encoding the SDH subunits, and the operon containing them are generically referred to as the "genes encoding SDH."

As genes encoding SDH of enterobacteria, the nucleotide sequences of such genes of *Pantoea ananatis* and the amino acid sequences of the subunits are shown in SEQ ID NOS: 1 to 6.

As the genes encoding SDH of coryneform bacteria, for example, there are disclosed the sequences of the sdh operon of *Corynebacterium glutamicum* (GenBank accession No. NCgl0359 (sdhC) NCgl0360 (sdhA) NCgl0361 (sdhB)), and the sdh operon of *Brevibacterium flavum* (Japanese Patent Laid-open No. 2005-095169, EP672077A1).

As the genes encoding SDH of coryneform bacteria, the nucleotide sequences of the genes of *Corynebacterium glutamicum* ATCC 13032, and the amino acid sequences of the subunits are shown in SEQ ID NOS: 73 to 76, and the nucleotide sequences of the genes of *Brevibacterium lactofermentum* (*Corynebacterium glutamicum*) ATCC 13869 and the amino acid sequences of the subunits are shown in SEQ ID NOS: 77 to 80.

In accordance with the presently disclosed subject matter, the α-ketoglutarate dehydrogenase (henceforth also referred to as "α-KGDH") activity means an activity of catalyzing the reaction oxidatively decarboxylating α-ketoglutaric acid (2-oxoglutaric acid) to generate succinyl-CoA. The aforementioned reaction can be catalyzed by three kinds of enzymes, α-KGDH (E1o, α-ketoglutarate dehydrogenase, EC: 1.2.4.2), dihydrolipoamide S-succinyltransferase (E2o, EC: 2.3.1.61), and dihydrolipoamide dehydrogenase (E3, EC: 1.8.1.4). That is, these three kinds of subunits can catalyze the following reactions, respectively, and the activity for catalyzing a reaction consisting of a combination of these three kinds of reactions is called the α-KGDH activity. The α-KGDH activity can be confirmed by measurement according to the method of Shiio et al. (Isamu Shiio and Kyoko Ujigawa-Takeda, Agric. Biol. Chem., 44 (8), 1897-1904, 1980).

E1o: 2-oxoglutarate+[dihydrolipoyllysine-residue succinyltransferase]lipoyllysine=[dihydrolipoyllysine-residue succinyltransferase]S-succinyldihydrolipoyllysine+CO$_2$ E2o: CoA+enzyme N6-(S-succinyldihydrolipoyl)lysine=succinyl-CoA+enzyme N6-(dihydrolipoyl)lysine E3: protein N6-(dihydrolipoyl)lysine+NAD$^+$=protein N6-(lipoyl)lysine+NADH+H$^+$ α-KGDH is also referred to as oxoglutarate dehydrogenase or 2-oxoglutarate dehydrogenase.

In Enterobacteriaceae bacteria such as *Pantoea ananatis*, the protein subunits which each have three kinds of enzymatic activities form a complex. The subunits are encoded by sucA, sucB and lpd, respectively, and the sucA and sucB genes are located downstream from the succinate dehydrogenase iron-sulfur protein gene (sdhB) (U.S. Pat. No. 6,331,419). Although these genes are described as genes of *Enterobacter agglomerans* AJ13355 in the aforementioned patent, this strain was later reclassified into *Pantoea ananatis*.

As genes encoding α-KGDH of enterobacteria, the nucleotide sequences of the sucA and sucB genes and the sucC gene locating downstream thereof and the amino acid sequences of the subunits of *Pantoea ananatis* are shown in SEQ ID NOS: 7 to 11. Furthermore, sucA, sucB and sucC encoding α-KGDH of *Escherichia coli* have been disclosed as Genbank NP_415254 and NP_415255, respectively.

In coryneform bacteria, the E1o subunit can be encoded by the odhA gene (registered as NCgl1084 of GenBank Accession No. NC_003450, which is also referred to as the sucA gene), and the E3 subunit can be encoded by the lpd gene (GenBank Accession No. Y16642). On the other hand, it is estimated that the E2o subunit can be encoded by the odhA gene and can constitute a bifunctional protein along with the E1o subunit (Usuda et al., Microbiology, 142, 3347-3354, 1996), or can be encoded by the gene registered as NCgl2126 of GenBank Accession No. NC_003450, which is different from the odhA gene. Therefore, in accordance with the presently disclosed subject matter, although the odhA gene encodes the E1o subunit, it can also encode the E2o subunit.

The nucleotide sequence of the odhA gene of *Brevibacterium lactofermentum* and the amino acid sequence of the E1o subunit encoded thereby (NCgl1084 of GenBank Accession No. NC_003450, WO2006/028298) are shown in SEQ ID NOS: 12 and 13. Furthermore, the nucleotide sequence of the aforementioned NCgl2126 of GenBank Accession No. NC_003450 and the amino acid sequence of the E2o subunit encoded thereby are shown in SEQ ID NOS: 14 and 15.

In accordance with the presently disclosed subject matter, genes encoding each of the α-KGDH subunits, and the gene cluster containing them are generically referred to as the "genes encoding α-KGDH".

The enzymatic activities can be decreased by, for example, the following methods.

(1) Method of Disrupting Genes which Encode Enzymes by Gene Recombination

By modifying a gene encoding SDH or α-KGDH (henceforth also referred to simply as "enzyme") by gene recombination, the number of the molecules of the enzyme protein encoded by any of these genes per cell can be decreased as compared to a parent strain or wild-type strain, or the enzyme protein molecule can be made not to be produced at all. Furthermore, the enzyme activity per molecule of the enzyme protein can be reduced, or the activity can be eliminated. The number of enzyme protein molecules can be decreased by decreasing expression of the gene encoding the enzyme. Decreasing expression includes decreasing transcription of mRNA transcribed from the gene and decreasing translation of the mRNA. Moreover, an enzyme protein molecule can be made not to be produced at all, or enzymatic activity per molecule of the enzyme protein can be decreased, or the activity can be eliminated by disruption of the gene encoding the enzyme. Examples of the wild-type strain used as an object of the comparison include the *Pantoea ananatis* AJ13355 strain, *Klebsiella planticola* AJ13399 strain, *Corynebacterium glutamicum* ATCC 13032 strain, *Brevibacterium lactofermentum* ATCC 13869 strain, *Brevibacterium flavum* ATCC 14067 strain, and the like.

The gene encoding SDH can correspond to one or more of the genes encoding the subunits of SDH, or the whole operon, and a mutation can be introduced into any of the genes encoding the subunits (SDHA, SDHB, SDHC, SDHD)

Although the gene encoding α-KGDH can correspond to one or more of the genes encoding the subunits of α-KGDH or the whole gene cluster, it can be a gene encoding the E1o subunit (sucA or odhA), or a gene encoding the E2o subunit (sucB).

Since the nucleotide sequences of the genes encoding the subunits of SDH or α-KGDH can differ depending on species to which the microorganism belongs or strain, the genes encoding them can be variants of the nucleotide sequences of SEQ ID NOS: 1, 7, 12, 14, 73, 77 and 81. Variants of the genes can be listed by searching an appropriate database, such as BLAST (http://blast.genome.jp/), or the like, with reference to the nucleotide sequences of SEQ ID NOS: 1, 7, 12, 14, 73, 77 and 81. The variants of the genes can include homologues of the genes, such as genes which can be amplified by PCR using a chromosome of a microorganism such as Enterobacteriaceae and coryneform bacteria as a template and synthetic oligonucleotides prepared on the basis of, for example, the nucleotide sequences of SEQ ID NOS: 1, 7, 12, 14, 73 and 81.

Examples of the subunits of SDH can include proteins having one of the amino acid sequences of SEQ ID NOS: 2 to 4, 6, 74 to 76 and 78 to 80, and examples of the subunits of α-KGDH include proteins having one of the amino acid sequences of SEQ ID NOS: 8 to 11, 13, 15 and 81. However, since the codons may differ and hence the nucleotide sequences of the genes may differ depending on species or strains of bacteria, the genes can encode a protein having any of the amino acid sequences which can include one or more substitutions, deletions, insertions or additions of one or several amino acid residues, so long as the function of the encoded protein is maintained. The number of the "one or several" amino acid residues is, for example, 1 to 20, and in another example 1 to 10, and in another example 1 to 5. These substitutions, deletions, insertions, or additions of one or several amino acids can be conservative mutations preserving normal functions of the proteins. Such a conservative mutation can be a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Typical examples of conservative mutations can be conservative substitutions. Examples of substitutions considered conservative substitutions can include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val.

The variants of the genes are not limited to genes having a nucleotide sequence of the coding regions in the nucleotide sequences of SEQ ID NOS: 1, 7, 12, 14, 73, 77 and 81, and can be a DNA which hybridizes with a nucleotide sequence complementary to any of those nucleotide sequences and nucleotide sequences of the coding regions or a probe prepared from any of those nucleotide sequences under stringent conditions. The term "stringent conditions" refers to conditions where a so-called specific hybrid is formed and a non-specific hybrid is not formed. Examples thereof can include conditions where DNAs having high homology, for example, homology of 80% or more, and in another example 90% or more, and in another example 95% or more, and in another example 97% or more, and in another example 99% or more, hybridize with each other and DNAs having homology less than the value described above do not hybridize with each other; and specifically can include washing conditions of typical Southern hybridization, e.g., washing at 60° C., 1×SSC, 0.1% SDS, and in another example 60° C., 0.1×SSC, 0.1% SDS, and in another example 68° C., 0.1×SSC, 0.1% SDS, once or twice or three times. Although the length of the probe can be chosen suitably depending on the hybridization conditions, it is usually 100 bp to 1 kbp.

Gene modification can be achieved by, for example, deleting a part of or the entire coding region of a gene on a chromosome, modifying an expression control sequence such as a promoter and the Shine-Dalgarno (SD) sequence, and the like. Furthermore, expression of a gene can also be decreased by modification of a non-translation region other than expression control sequence. Moreover, the entire gene including a flanking region on both sides of the gene on the chromosome can be deleted. Furthermore, it also can be achieved by introducing a mutation for one or more amino acid substitutions (missense mutation), introducing a stop codon (nonsense mutation), or introducing a frameshift mutation which adds or deletes one or two nucleotides by gene recombination (Journal of Biological Chemistry, 272: 8611-8617 (1997); Proceedings of the National Academy of Sciences, USA, 95 5511-5515 (1998); Journal of Biological Chemistry, 266, 20833-20839 (1991)).

Moreover, in enterobacteria, the sucA and sucB genes are located upstream of the sdh operon, and therefore a mutation for decreasing expression of the sdh operon and thereby decrease expression of the sucA and sucB genes can be introduced. Such a mutation can be utilized in accordance with the presently disclosed subject matter.

The expression that "to modify a gene by gene recombination" means to delete a part or all of an expression control sequence such as promoter region, a coding region, or a non-coding region of the gene on a chromosome, or insert another sequence into any of these regions using homologous recombination, and thereby decrease intracellular enzyme activity. A gene modification can be performed to such an extent that inactivation of the gene should no longer be restored by spontaneous mutation.

However, the modification can be performed with a conventional mutagenesis such as X-ray or ultraviolet irradiation or a treatment with a mutagen such as N-methyl-N'-nitro-N-nitrosoguanidine, so long as the SDH and α-KGDH activities are decreased.

The expression control sequence can be modified for one or more nucleotides. In another exemplary embodiment in accordance with the disclosed subject matter the expression control sequence can be modified for two or more nucleotides. And, in another exemplary embodiment in accordance with the disclosed subject matter the expression control sequence can be modified for three or more nucleotides. When a deletion is performed for a coding region, the region to be deleted can be in the N-terminus region, an internal region, or in the C-terminus region, or the entire coding region, so long as the function of the enzyme protein is decreased or eliminated. Deletion of a longer region will usually ensure inactivation of the gene. Furthermore, the reading frames upstream and downstream of the deleted region can be different from each other.

Also, when another sequence is inserted into the coding region, the sequence can be inserted into any region, and inserting a longer region will usually ensure inactivation of the gene. The reading frames upstream and downstream of the insertion site can be different from each other. The other sequence is not particularly limited so long as the sequence has the effect of decreasing or eliminating the function of the enzyme protein, and examples can include a transposon carrying an antibiotic resistance gene or a gene useful for L-glutamic acid production.

A gene on the chromosome can be modified as described above by, for example, preparing a deletion-type version of the gene in which a partial sequence of the gene is deleted so as it is unable to produce an enzyme protein that can normally function, and transforming a bacterium with a DNA containing the deletion-type gene to cause homologous recombination between the deletion-type gene and the native gene on the chromosome, and thereby substitute the deletion-type gene for the gene on the genome. The enzyme protein encoded by the deletion-type gene has a conformation different from that of the wild-type enzyme protein, if it is even produced, and thus the function is decreased or eliminated. Such gene disruption based on gene substitution utilizing homologous recombination has been already established, and can be performed by methods using a linear DNA such as Red-driven integration (Datsenko, K. A, and Wanner, B. L., Proc. Natl. Acad. Sci. USA, 97:6640-6645 (2000)), and Red-driven integration in combination with an excisive system derived from λ phage described in Cho, E. H., Gumport, R. I., Gardner, J. F. J. Bacteriol. 184: 5200-5203 (2002) (WO2005/010175), using a plasmid containing a temperature-sensitive replication origin, or a plasmid capable of conjugative transfer, methods utilizing a suicide vector which does not have a replication origin usable in the chosen host (U.S. Pat. No. 6,303,383, Japanese Patent Laid-open No. 05-007491) etc.

As shown in Reference Example 1, a strain resistant to a λ Red gene product, for example, the *Pantoea ananatis* SC17 (0) strain, can be suitably used for the Red driven integration. The SC17(0) strain was deposited in the Russian National Collection of Industrial Microorganisms (VKPM), GNII Genetika on Sep. 21, 2005 under an accession number of VKPM B-9246.

Decreased transcription of the genes can be confirmed by comparison of the mRNA levels of the genes with those in the wild-type or unmodified strain. Examples of methods for measuring expression can include Northern hybridization and Reverse-Transcriptase PCR (RT-PCR) (Molecular Cloning, Cold Spring Harbor Laboratory Press, Cold spring Harbor (USA), (2001)). The decrease of transcription can be at any level so long as it is decreased compared with that of a wild-type or unmodified strain. For example, the level can be decreased to within a range of 75% or less, to within a range of 50% or less, to within a range of 25% or less, to within a range of 10% or less, or to a value of 0%, of the level of a wild-type or unmodified strain.

The decrease in the amount of protein encoded by a gene can be confirmed by Western blotting using an antibody (Molecular Cloning, Cold Spring Harbor Laboratory Press, Cold spring Harbor (USA), (2001)). The decrease of the protein amount can be at any level so long as it is decreased as compared to that of a wild-type or unmodified strain, and for example, the level can include a range of 75% or less, a range of 50% or less, a range of 25% or less, a range of 10% or less, or a value of 0%, of the level of a wild-type or unmodified strain.

(2) Acquisition of α-KGDH Activity-Decreased Strain Utilizing Auxotrophy

An α-KGDH activity-decreased strain can be obtained by the method of (1) described above, and can also be obtained by the following method utilizing auxotrophy.

For example, microbial cells can subjected to a usual mutagenesis using N-methyl-N'-nitro-N-nitrosoguanidine (for example, 250 µg/ml, 30° C., 20 minutes), and then cultured on a solid medium to allow colony formation. By separating a mutated strain which cannot grow in a medium containing L-glutamic acid as a single carbon source and single nitrogen source from the colonies by the replica plating, an α-KGDH activity-decreased strain can be isolated.

Examples of α-KGDH activity-decreased strain include, for example, the following strains.

*Brevibacterium lactofermentum* AJ12821 (FERM BP-4172, U.S. Pat. No. 5,492,818)
*Brevibacterium flavum* AJ12822 (FERM BP-4173, U.S. Pat. No. 5,492,818)
*Corynebacterium glutamicum* AJ12823 (FERM BP-4174, U.S. Pat. No. 5,492,818)
*Brevibacterium lactofermentum* ΔS stain (WO95/34672)
*Corynebacterium glutamicum* OAGN, OA2-2, OAGN2-2 (WO2006/028298)
*Pantoea ananatis* AJ13601 (FERM BP-7207)
*Klebsiella planticola* AJ13410 (FERM BP-6617)
*Pantoea ananatis* AJ13355 (FERM BP-6614)

(3) Acquisition of SDH Activity-Decreased Strain Using Succinic Acid Auxotrophy as Indicative Index An α-KGDH activity-decreased strain can require succinic acid for growth due to decrease of succinyl-CoA supply. On the other hand, it is known that an α-KGDH and SDH double deficient strain can be recovered from the succinic acid auxotrophy (J. Gen. Microbiol., 1978 July; 107(1):1-13). Therefore, by selecting a strain which can recover from succinic acid auxotrophy from α-KGDH activity-decreased strains, an α-KGDH and SDH activity-decreased strain can be obtained. Specifically, α-KGDH activity-decreased strains can be plated on a minimal medium not containing succinic acid, and allowed to form colonies. In an α-KGDH activity-decreased strain which can grow in the minimal medium not containing succinic acid, the gene encoding SDH highly frequently can contain a mutation.

<3> Method for Producing L-Amino Acid

By culturing such a microorganism as described above in a medium to produce and accumulate an L-amino acid in the medium or cells and collecting the L-amino acid from the medium or the cells, L-amino acid can be produced.

A medium used for the culture can be a medium containing a carbon source, a nitrogen source and mineral salts as well as organic trace nutrients such as amino acids and vitamins, as required. Either a synthetic medium or a natural medium can be used. Any carbon source and any nitrogen source can be used so long as they can be utilized by the strain to be cultured.

Sugars such as glucose, glycerol, fructose, sucrose, maltose, mannose, galactose, starch hydrolysates and molasses can be used as the carbon source. In addition, organic acids such as acetic acid and citric acid, and alcohols such as ethanol can also be used each alone or in a combination with other carbon sources. Ammonia, ammonium salts such as ammonium sulfate, ammonium carbonate, ammonium chloride, ammonium phosphate and ammonium acetate, nitric acid salts and so forth can be used as the nitrogen source. Amino acids, vitamins, fatty acids, nucleic acids, those containing those substances such as peptone, casamino acid, yeast extract and soybean protein decomposition product, and the like, can be used as the organic trace nutrients. When an auxotrophic mutant strain that requires an amino acid or the like for its growth is used, the required nutrient can be supplemented. Phosphoric acid salts, magnesium salts, calcium salts, iron salts, manganese salts, and the like, can be used as the mineral salts.

The culture can be performed in aerobic conditions, while the fermentation temperature can be controlled to be 20 to 45° C., and pH to be 3 to 9. For adjustment of pH, an inorganic or organic acidic or alkaline substance, ammonia gas or the like can be used. A substantial amount of L-amino acid can be accumulated in the culture medium or cells after 10 to 120 hours of culture in such a manner as described above.

Moreover, when the objective L-amino acid is L-glutamic acid, the culture can be performed to produce and accumulate L-glutamic acid with precipitating L-glutamic acid in a medium using, as the medium, a liquid medium adjusted to satisfy a condition under which L-glutamic acid is precipitated. Examples of the condition under which L-glutamic acid is precipitated can include, for example, pH within a range of 5.0 to 4.0, pH within a range of 4.5 to 4.0, pH within a range of 4.3 to 4.0, or a pH of 4.0. In order to obtain both improvement of growth under an acidic condition and efficient precipitation of L-glutamic acid, the pH can be within a range of 5.0 to 4.0, a range of 4.5 to 4.0, or a range of 4.3 to 4.0. The culture can be performed at the aforementioned pH for the whole culture period or a part of it.

Collection of L-amino acid from the culture broth after the culture can be performed in a conventional manner. For example, after the cells are removed from the culture broth, L-amino acid can be collected by concentrating the broth to crystallize the L-amino acid, ion exchange chromatography, or the like. When the culture is performed under conditions under which L-glutamic acid is precipitated, L-glutamic acid precipitated in the medium can be collected by centrifugation or filtration. In this case, L-glutamic acid dissolving in the medium can be precipitated and then separated together.

In addition, the culture can be performed in a medium containing trehalose. As for the concentration of trehalose contained in the medium, exemplary ranges of the concentration can include the range of 0.1 g/L or more, is the range of 0.2 g/L or more, and the range of 0.5 g/L or more. When a coryneform bacterium is used, in particular, exemplary ranges of the concentration can include the range of 0.5 g/L or more, th range of 0.75 g/L or more, and the range of 2 g/L or more. As trehalose added to the medium, crystalline trehalose can be dissolved, or trehalose can be contained in a mother liquor obtained after a target substance is collected from a fermentation liquor produced in a fermentation process may also be used. Moreover, trehalose contained in the medium can be trehalose produced in a fermentation broth as a by-product.

Furthermore, if betaine (N-methylglycine, N,N-dimethylglycine, N,N,N-trimethylglycine, [2-hydroxyethyl]trimethyl ammonium) is added in addition to trehalose, productivity of the target substance can be further improved. Exemplary ranges of the concentration of betaine can be a range of 0.1 g/L or more, a range of 0.25 g/L or more, and a range of 0.5 g/L or more.

EXAMPLES

Hereinafter, the present invention will be described in more detail by referring to examples.

Reference Example 1

Construction of *Pantoea ananatis* Strain which is Resistant to the λ Red Gene Product To disrupt the sdhA gene in *Pantoea ananatis*, a recipient strain was constructed which can efficiently carry out the method called "Red-driven integration" or "Red-mediated integration" (Proc. Natl. Acad. Sci. USA, 97, 6640-6645 (2000)).

First, the novel helper plasmid RSF-Red-TER which expresses the gam, bet and exo genes of λ (henceforth referred to as "λ Red genes") was constructed (FIG. 1). The details thereof will be described in Reference Example 2.

This plasmid can be used in a wide range of hosts having different genetic backgrounds. This is because 1) this plasmid has the replicon of the RSF1010 wide host spectrum plasmid (Scholz, et al., 1989; Buchanan-Wollaston et al., 1987), which can be stably maintained by many types of gram negative and gram positive bacteria, and even plant cells, 2) the λ Red genes, gam, bet and exo genes, are under the control of the PlacUV5 promoter, which is recognized by the RNA polymerases of many types of bacteria (for example, Brunschwig, E. and Darzins, A., Gene, 111, 1, 35-41 (1992); Dehio, M. et al, Gene, 215, 2, 223-229 (1998)), and 3) the autoregulation factor $P_{lacUV5}$-lacI and the ρ-non-dependent transcription terminator (TrrnB) of the rrnB operon of *Escherichia coli* lower the basal expression level of the λ Red genes (Skorokhodova, A. Yu et al, Biotekhnologiya (Rus), 5, 3-21 (2004)). Furthermore, the RSF-Red-TER plasmid contains the levansucrase gene (sacB), and by using this gene, the plasmid can be collected from cells in a medium containing sucrose.

In *Escherichia coli*, the frequency of integration of a PCR-generated DNA fragment along with the short flanking region provided by the RSF-Red-TER plasmid is as high as the frequency obtainable using the pKD46 helper plasmid (Datsenko, K. A., Wanner, B. L., Proc. Natl. Acad. Sci. USA, 97, 6640-6645 (2000)). However, expression of the λ Red genes is toxic to *Pantoea ananatis*. Cells transformed with the RSF-Red-TER helper plasmid grow extremely slowly in the LB medium containing IPTG (isopropyl-β-D-thiogalactopyranoside, 1 mM) and an appropriate antibiotic (25 μg/ml of chloramphenicol or 40 μg/ml of kanamycin), and the efficiency of λ Red-mediated recombination is extremely low ($10^{-8}$), if observed at all.

A variant strain of *Pantoea ananatis* which is resistant to expression of all three of the λ Red genes was selected. For this purpose, the RSF-Red-TER plasmid was introduced into the *Pantoea ananatis* SC17 strain (U.S. Pat. No. 6,596,517) by electroporation. After an 18 hour culture, about $10^6$ of transformants were obtained, and among these, 10 clones formed large colonies, and the remainder all formed extremely small colonies. After an 18 hour culture, the large colonies had a size of about 2 mm, and the small colonies had a size of about 0.2 mm. Whereas the small colonies did not grow any more even if the culture was extended to 24 hours, the large colonies continued to grow. One of the large colony *Pantoea ananatis* mutant strains and resistant to expression of all of the three λ Red genes (gam, bet, and exo) was used for the further analysis.

The RSF-Red-TER plasmid DNA was isolated from one clone of the large colony clones, and from several clones of small colonies, and transformed again into *Escherichia coli* MG1655 to examine the ability of the plasmid to synthesize an active Red gene product. By a control experiment for Red-dependent integration in the obtained transformants, it was demonstrated that only the plasmid isolated from the large colony clone induced expression of the λ Red genes required for the Red-dependent integration. In order to investigate whether the Red-mediated integration occurs in the selected large colony clone, electroporation was performed using a linear DNA fragment produced by PCR. This fragment was designed so that it should contain a $Km^R$ marker and a flanking region of 40 bp homologous to the hisD gene. This fragment was integrated into the hisD gene of *Pantoea ananatis* at the SmaI recognition site. Two small colony clones were used as control. The nucleotide sequence of the hisD gene of *Pantoea ananatis* is shown in SEQ ID NO: 16. For PCR, the oligonucleotides of SEQ ID NOS: 17 and 18 were used as primers, and the pMW118-(λatt-$Km^r$-λatt) plasmid was used as the template. The two small colony clones which were not resistant to the λ Red genes, were used as a control. Construction of the pMW118-(λattL-$Km^r$-λattR) plasmid will be explained in detail in Reference Example 3.

The RSF-Red-TER plasmid can induce expression of the Red genes by the lacI gene carried on the plasmid. Two kinds of induction conditions were investigated. In the first group, IPTG (1 mM) was added 1 hour before the electroporation, and in the second group, IPTG was added at the start of the culture for preparation of cells of which electroporation is possible. The growth rate of the cells harboring RSF-Red-TER derived from the large colony clone was not significantly lower than that of a strain not having the SC17 plasmid. The addition of IPTG only slightly decreased the growth rate of these cultures. On the other hand, the progeny of the small colony clones grew extremely slowly even without the addition of IPTG, and after induction, growth was substantially arrested. After electroporation of the cells of the progeny of the large colony clone, many $Km^R$ clones grew (18 clones after a short induction time, and about 100 clones after an extended induction time). All the 100 clones that were investigated had a His⁻ phenotype, and about 20 clones were confirmed by PCR to have the expected structure of chromosome in the cells. On the other hand, even when electroporation was performed with the progeny of the small colony clones, an integrated strain was not obtained.

The obtained large colony clone was grown on a plate containing 7% sucrose to eliminate the plasmid, and transformed again with RSF-Red-TER. The strain without the plasmid was designated SC17(0). This strain was deposited at the Russian National Collection of Industrial Microorganisms (VKPM, GNII Genetica (address: Russia, 117545 Moscow, 1 Dorozhny proezd. 1) on Sep. 21, 2005, and assigned an accession number of VKPM B-9246.

All the clones which grew after the aforementioned re-transformation formed large colonies like the parent strain clone SC17(0). The Red-mediated integration experiment was performed in the SC17(0) strain re-transformed with the RSF-Red-TER plasmid. Three of the independent transformants were investigated using the same DNA fragment as that used for the previous experiment. The short induction time (1 hour before electroporation) was employed. $Km^R$ clones exceeding ten clones grew in each experiment. All the examined clones had the His⁻ phenotype. In this way, a mutant strain designated SC17(0) resistant to the expression of the λ Red genes was selected. This strain can be used as a recipient strain suitable for the Red-dependent integration into the *Pantoea ananatis* chromosome.

Reference Example 2

Construction of Helper Plasmid RSF-Red-TER

Figure 2:
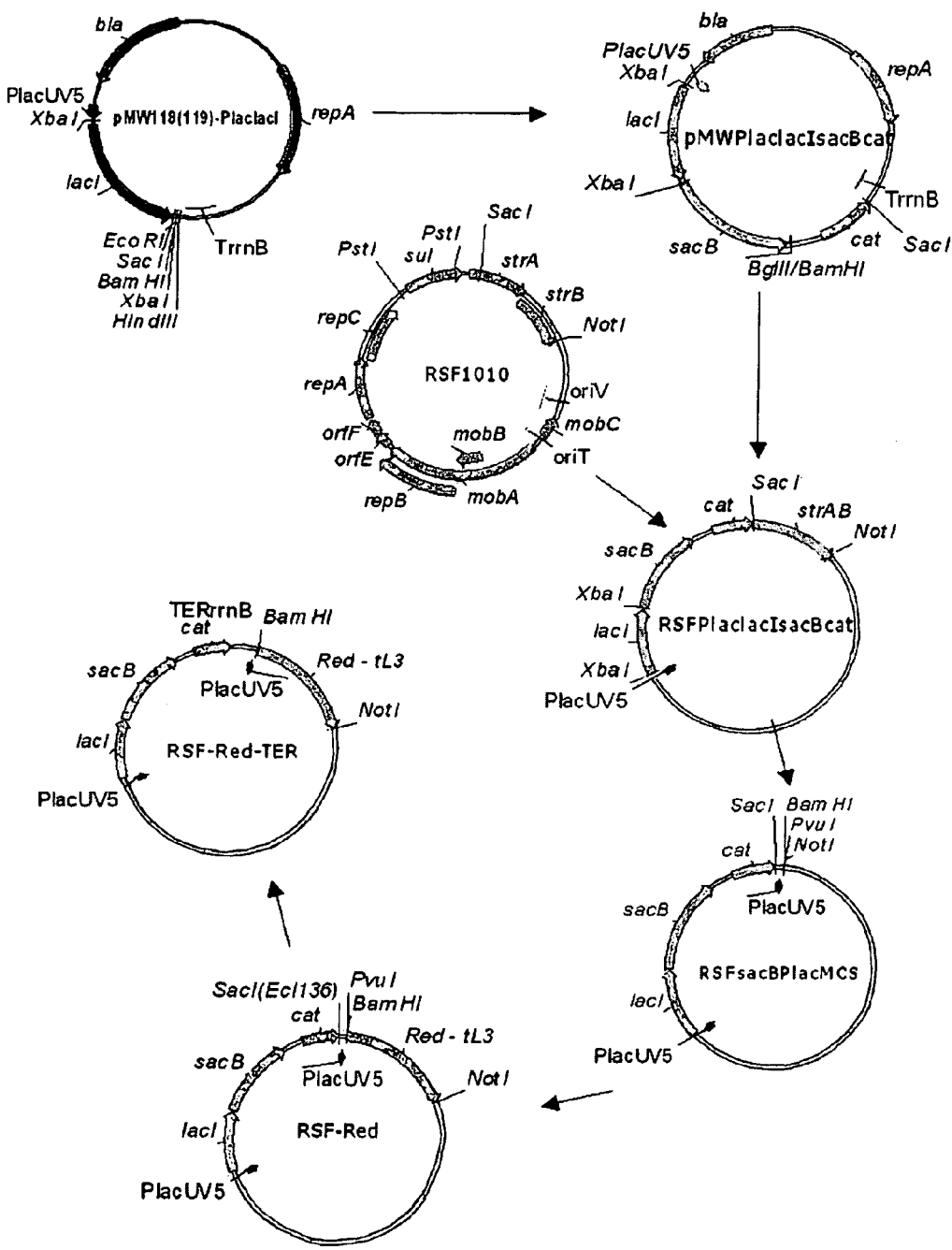
FIG. 2 shows the construction of the helper plasmid RSF-Red-TER.

The construction scheme of the helper plasmid RSF-Red-TER is shown in FIG. 2.

As a first step of the construction, a RSFsacBPlacMCS vector was designed. For this purpose, DNA fragments containing the cat gene of the pACYC184 plasmid and the structural gene region of the sacB gene of *Bacillus subtilis* were amplified by PCR using the oligonucleotides of SEQ ID NOS: 19 and 20, and 21 and 22, respectively. These oligonucleotides contained BglII, SacI, XbaI and BamHI restriction enzyme sites, required and convenient for further cloning, in the 5' end regions, respectively. The obtained sacB fragment of 1.5 kb was cloned into the previously obtained pMW119-$P_{lac}$lacI vector at the XbaI-BamHI site. This vector was constructed in the same manner as that described for the pMW118-$P_{lac}$lacI vector (Skorokhodova, A. Yu et al, Biotekhnologiya (Rus), 5, 3-21 (2004)). However, this vector contained a polylinker moiety derived from pMW219 instead of the pMW218 plasmid.

Then, the aforementioned cat fragment of 1.0 kb was treated with BglII and SacI, and cloned into the RSF-$P_{lac}$lacIsacB plasmid obtained in the previous step at the BamHI-SacI site. The obtained plasmid PMW-$P_{lac}$lacIsacBcat contained the PlacUV5-lacI-sacB-cat fragment. In order to subclone this fragment into the RSF1010 vector, PMW-$P_{lac}$lacIsacBcat was digested with BglII, blunt-ended with DNA polymerase I Klenow fragment, and successively digested with SacI. A 3.8 kb BglII-SacI fragment of the pMWP$_{lac}$lacIsacBcat plasmid was eluted from 1% agarose gel, and ligated with the RSF1010 vector which had been treated with PstI and SacI. *Escherichia coli* TG1 was transformed with the ligation mixture, and plated on the LB medium containing chloramphenicol (50 mg/L). The plasmids isolated from the grown clones were analyzed with restriction enzymes to obtain a RSFsacB plasmid. In order to construct a RSFsacB-$P_{lac}$MCS vector, a DNA fragment containing the $P_{lacUV5}$ promoter was amplified by PCR using oligonucleotides of SEQ ID NOS: 23 and 24 as primers and the pMW119-$P_{lac}$lacI plasmid as the template. The obtained fragment of 146 bp was digested with SacI and NotI, and ligated with the SacI-NotI large fragment of the RSFsacB plasmid. Then, by PCR using the oligonucleotides of SEQ ID NOS: 25 and 26 as primers, and the pKD46 plasmid (Datsenko, K. A., Wanner, B. L., Proc. Natl. Acad. Sci. USA, 97, 6640-6645 (2000)) as the template, a DNA fragment of 2.3 kb containing the λRedαβγ genes and the transcription terminator tL3 was amplified. The obtained fragment was cloned into the RSFsacBP$_{lac}$MCS vector at the PvuI-NotI site. In this way, the RSFRed plasmid was designed.

In order to eliminate the read through transcription of the Red genes, a ρ-dependent transcription terminator of the rrnB operon of *Escherichia coli* was inserted at a position between the cat gene and the $P_{lacUV5}$ promoter. For this purpose, a DNA fragment containing the $P_{lacUV5}$ promoter and the TrrnB terminator was amplified by PCR using the oligonucleotides of SEQ ID NOS: 27 and 24 as primers and the chromosome of *Escherichia coli* BW3350 as a template. These obtained fragments were treated with KpnI and ligated. Then, the 0.5 kb fragment containing both $P_{lacUV5}$ and TrrnB was amplified by PCR using the oligonucleotides of SEQ ID NOS: 24 and 28 as primers. The obtained DNA fragment was digested with EcoRI, blunt-ended by a treatment with DNA polymerase I Klenow fragment, digested with BamHI, and ligated with the Ecl136II-BamHI large fragment of the RSF-sacBPlacMCS vector. The obtained plasmid was designated RSF-Red-TER.

Reference Example 3

Construction of the pMW118-(λattL-Km$^r$-λattR) Plasmid

The pMW118-(λattL-Km$^r$-λattR) plasmid was constructed from the pMW118-attL-Tc-attR (WO2005/010175) plasmid by replacing the tetracycline resistance marker gene with the kanamycin resistance gene of the pUC4K plasmid. For that purpose, the EcoRI-HindIII large fragment from pMW118-attL-Tc-attR plasmid was ligated to two fragments from the pUC4K plasmid: HindIII-PstI fragment (676 bp) and EcoRI-HindIII fragment (585 bp). Basic pMW118-attL-Tc-attR was obtained by ligation of the following four fragments:

1) the BglII-EcoRI fragment (114 bp) including attL (SEQ ID NO: 31) which was obtained by PCR amplification of the region corresponding to attL of the *Escherichia coli* W3350 (containing λ prophage) chromosome using the primers P1 and P2 (SEQ ID NOS: 29 and 30) (these primers contained the subsidiary recognition sites for BglII and EcoRI);

2) the PstI-HindIII fragment (182 bp) including attR (SEQ ID NO: 34) which was obtained by PCR amplification of the region corresponding to attR of the *Escherichia coli* W3350 (containing λ prophage) chromosome using the primers P3 and P2 (SEQ ID NOS: 32 and 33) (these primers contained the subsidiary recognition sites for PstI and HindIII):

3) the BglII-HindIII large fragment (3916 bp) of pMW118-ter_rrnB. The plasmid pMW118-ter_rrnB was obtained by ligation of the following three DNA fragments:

the large DNA fragment (2359 bp) including the AatII-EcoRI fragment of pMW118 that was obtained by digesting pMW118 with EcoRI, treating with Klenow fragment of DNA polymerase I, and then digesting with AatII;

the small AatII-BglII fragment (1194 bp) of pUC19 including the bla gene for ampicillin resistance (Ap$^R$), which was obtained by PCR amplification of the corresponding region of the pUC19 plasmid using the primers P5 and P6 (SEQ ID NOS: 35 and 36) (these primers contained the subsidiary recognition sites for PstI, AatII and BglII);

the small BglII-PstI fragment (363 bp) of the transcription terminator ter_rrnB, which was obtained by PCR amplification of the corresponding region of the *Escherichia coli* MG1655 chromosome using the primers P7 and P8 (SEQ ID NOS: 37 and 38) (these primers contained the subsidiary recognition sites for PstI and BglII); and 4) the small EcoRI-PstI fragment (1388 bp) (SEQ ID NO: 39) of pML-Tc-ter_thrL including the tetracycline resistance gene and the ter_thrL transcription terminator; the pML-Tc-ter_thrL plasmid was obtained by the following two steps:

the pML-ter_thrL plasmid was obtained by digesting the pML-MCS plasmid (Mashko, S. V. et al., Biotekhnologiya (in Russian), 2001, no. 5, 3-20) with the XbaI and BamHI, followed by ligation of the large fragment (3342 bp) with the XbaI-BamHI fragment (68 bp) carrying ter_thrL terminator obtained by PCR amplification of the corresponding region of the *Escherichia coli* MG1655 chromosome using the primers P9 and P10 (SEQ ID NOS: 40 and 41) (these primers contained the subsidiary recognition sites for PstI, XbaI and BamHI); and the pML-Tc-ter_thrL plasmid was obtained by digesting the pML-ter_thrL plasmid with KpnI and XbaI followed by treatment with Klenow fragment of DNA polymerase I and ligated with the small EcoRI-Van91I fragment (1317 bp) of pBR322 including the tetracycline resistance gene (pBR322 was digested with EcoRI and Van91I and then treated with Klenow fragment of DNA polymerase I).

Example 1

Effect of sdhA Gene and sucA Gene Disruption in *Pantoea ananatis*

(1) Construction of Glutamic Acid-Producing Plasmid RSFPPG

A plasmid RSFPPG was constructed in which L-glutamic acid biosynthesis system genes, prpC gene (International Patent Publication WO2006/051660), ppc gene and gdh gene (EP0999282A) were amplified.

The primer 1 (SEQ ID NO: 42) and the primer 2 (SEQ ID NO: 43) for amplifying a part of RSFCPG (EP1233068A) other than ORF of the gltA gene were designed. By using these primers and RSFCPG as the template, PCR was performed to obtain a fragment of about 14.9 kb. As for prpC, PCR was performed using the primer 3 (SEQ ID NO: 44) and the primer 4 (SEQ ID NO: 45) and the chromosomal DNA of the *E. coli* W3110 strain as the template to obtain a fragment of about 1.2 kb. Both the PCR products were treated with BglII and KpnI, ligated, and then used to transform the *E. coli* JM109 strain. All the colonies which emerged were collected, and plasmids were extracted from the colonies as a mixture. The *E. coli* ME8330 strain which is a citrate synthase (CS) deficient strain was transformed with the plasmid mixture, and the cell suspension was applied on the M9 minimal medium (containing 5 g of glucose, 2 mM magnesium sulfate, 3 g of monopotassium phosphate, 0.5 g of sodium chloride, 1 g of ammonium chloride and 6 g of disodium phosphate in 1 L of pure water) containing 50 mg/L of uracil and 5 mg/L of thiamine HCl. From the emerged strains, a plasmid was extracted and designated RSFPPG. This plasmid RSFPPG was introduced into the *Pantoea ananatis* NP106 strain, which is an L-glutamic acid producing strain, to construct an L-glutamic acid producing strain, NP106/RSFPPG (this strain is referred to as "NA1 strain").

The NP106 strain was obtained as follows. The *Pantoea ananatis* AJ13601 strain described above was cultured overnight at 34° C. in the LBGM9 liquid medium with shaking, and then the medium was diluted so that 100 to 200 colonies appear per one plate and applied to an LBGM9 plate containing 12.5 mg/L of tetracycline. The colonies which appeared were replicated on an LBGM9 plate containing 12.5 mg/L of tetracycline and 25 mg/L of chloramphenicol. A strain which is sensitive to chloramphenicol was selected to obtain a strain from which pSTVCB was eliminated. This strain was designated G106S. The G106S strain was further cultured overnight at 34° C. in the LBGM9 liquid medium with shaking, and the medium was diluted so that 100 to 200 colonies should appear per one plate, and applied to an LBGM9 plate without drugs. The colonies which appeared were replicated to an LBGM9 plate containing 12.5 mg/L of tetracycline and an LBGM9 plate without drugs. A strain which was sensitive to tetracycline was selected to obtain a strain from which RSFCPG was eliminated. This strain was designated NP106.

The NP106 obtained as described above is a strain not containing both two of the plasmids RSFCPG and pSTVCB, which are harbored by the AJ13601 strain.

(2) Construction of sdhA Gene-Disrupted Strain

PCR was performed using pMW-attL-Km$^r$-attR as the template and the primers of SEQ ID NOS: 46 and 47 to amplify a gene fragment containing a kanamycin resistance gene, attL and attR sequences of λ phage at the both ends of the resistance gene, and 50 bp upstream sequence and 50 bp downstream sequence of the sdhA gene added to the outer ends of the λ phage sequences. This fragment was purified using Wizard PCR Prep DNA Purification System (produced by Promega).

Then, the SC17(0) strain was transformed with RSF-Red-TER to obtain an SC17(0)/RSF-Red-TER strain. This strain was cultured overnight in the L medium (medium containing 10 g of Bacto tryptone, 5 g of yeast extract and 5 g of NaCl in 1 L of pure water, pH 7.0) containing 25 mg/L of chloramphenicol. The culture medium after the overnight culture was inoculated to 100 mL of the L medium containing 25 mg/L of chloramphenicol and 1 mM isopropyl-β-D-thiogalactopyranoside in 1/100 volume, and culture was performed at 34° C. for 3 hours. The cells prepared as described above were collected, washed three times with ice-cooled 10% glycerol, and finally suspended in 0.5 mL of 10% glycerol. The suspended cells were used as competent cells, and 100 ng of the PCR fragment prepared as described above was introduced into the cells using GENE PULSER II (produced by BioRad) under the conditions of a field strength of 18 kV/cm, capacitor capacity of 25 μF and resistance of 200Ω. Ice-cooled SOC medium (20 g/L of Bacto tryptone, 5 g/L of yeast extract, 0.5 g/L of NaCl, and 10 g/L of glucose) was added to the cell suspension, and culture was performed at 34° C. for 2 hours with shaking. The culture was applied to a medium prepared by adding ingredients of minimal medium (medium containing 5 g of glucose, 2 mM magnesium sulfate, 3 g of monopotassium phosphate, 0.5 g of sodium chloride, 1 g of ammonium chloride and 6 g of disodium phosphate in 1 L) and 40 mg/L of kanamycin to the L medium (medium containing 10 g of Bacto tryptone, 5 g of yeast extract, 5 g of NaCl and 15 g of agar in 1 L of pure water, pH 7.0). The colonies which emerged were purified with the same medium, and then it was confirmed that the sdhA gene was replaced with the kanamycin resistance gene by PCR.

From this sdhA gene-deficient strain, the chromosome was extracted using Bacterial Genomic DNA Purification Kit produced by Edge Biosystems. Separately, the NA1 strain was cultured overnight on an agar medium obtained by adding the ingredients of the minimal medium described above and 12.5 mg/L of tetracycline to the L medium. The cells were scraped with a loop, washed three times with ice-cooled 10% glycerol, and finally suspended in 10% glycerol so as to have a final volume of 500 μL. The suspended cells were used as competent cells, and 600 ng of the aforementioned chromosome DNA was introduced into the cells using GENE PULSER II (produced by BioRad) under the conditions of a field strength of 17.5 kV/cm, capacitor capacity of 25 μF and resistance of 200Ω. Ice-cooled SOC medium was added to the cell suspension, and culture was performed at 34° C. for 2 hours with shaking. Then, the culture was applied to an agar medium prepared by adding ingredients of the minimal medium described above, 12.5 mg/L of tetracycline and 40 mg/L of kanamycin to the L medium. The colonies which emerged were purified with the same medium, and then it was confirmed that the sdhA gene had been replaced with the kanamycin resistance gene by PCR.

The NA1 strain is deficient in the sucA gene encoding the E1 subunit of α-KGDH. On the other hand, no mutation is contained in the sucA gene of the SC17(0)/RSF-Red-TER strain. The sdhA gene and the sucA gene are located at positions extremely close to each other, and the wild-type sucA gene is also transferred at a certain ratio together with the mutated sdhA at the time of the transformation with the chromosomal DNA of the sdhA gene-deficient strain. Therefore, the obtained sdhA-deficient NA1 strains include two types of strains, one deficient in the sucA gene and one returned to the wild-type. Therefore, regions corresponding to the mutation site of the sucA gene of NA1 were amplified by PCR, and it was confirmed whether they were deficient in sucA or whether the sucA gene returned to the wild-type on the basis of whether they could be digested with the restriction enzyme BglII to obtain an sdhA single deficient strain and an sucAsdhA double deficient strain.

(3) Evaluation of L-Glutamic Acid Producing Ability of sdhA-Deficient Strain and sucAsdhA Double Deficient Strain Then, in order to evaluate the L-glutamic acid producing ability of the sdhA-deficient strain and the sucAsdhA double deficient strain obtained as described above, these strains were each inoculated into 5 mL of a medium having the composition shown below contained in a test tube, and culture was performed for 18 hours. Whereas the NA1 strain which is the sucA single deficient strain hardly grew in the medium, and showed L-glutamic acid accumulation of only about 3.3 g/L, the sdhA single deficient strain showed 13.2 g/L of L-glutamic acid accumulation, which markedly exceeded the result of the sucA single deficient strain. On the other hand, the sucAsdhA double deficient strain showed 14.7 g/L of L-glutamic acid accumulation, and was confirmed to have L-glutamic acid producing ability higher than those of the strains deficient in one of sucA and sdhA, and show markedly improved growth.

Composition of Medium for Evaluation of L-Glutamic Acid Production:

| part A: | |
|---|---|
| Sucrose | 30 g/L |
| MgSO$_4$•7H$_2$O | 0.5 g/L |
| part B: | |
| (NH$_4$)$_2$SO$_4$ | 20 g/L |
| KH$_2$PO$_4$ | 2 g/L |
| FeSO$_4$•7H$_2$O | 20 mg/L |
| MnSO$_4$•5H$_2$O | 20 mg/L |
| Yeast Extract (Difco) | 2 g/L |
| Calcium pantothenate | 18 mg/L |
| part C: | |
| Calcium carbonate | 20 g/L |

The ingredients of the parts A and B were sterilized at 115° C. for 10 minutes by autoclaving, and the ingredient of the part C was sterilized at 180° C. for 3 hours with dry heat. After the ingredients of the three parts were cooled to room temperature, they were mixed and used.

TABLE 1

| | OD620 nm (x1/51) | Glu (g/L) | RS (g/L) | Yield (%) |
|---|---|---|---|---|
| NA1 | 0.034 | 3.3 | 17.1 | 27.1 |
| NA1 sdhA | 0.439 | 13.2 | 0.0 | 45.3 |
| NA1 sucAsdhA | 0.482 | 14.7 | 0.1 | 50.7 |

RS: Residual sugar

Example 2

Effect of odhA Gene and sdhA Gene Disruption in Coryneform Bacterium (1) Construction of odhA Gene-Disrupted Strain From the *Brevibacterium flavum* ATCC 14067 strain (currently classified into *Corynebacterium glutamicum*), a strain deficient in the odhA gene, in which G at position 837 of the yggB gene (SEQ ID NO: 56) was replaced with A, and the promoter of the gdh gene was modified, was constructed. Although the *B. flavum* ATCC 14067 strain was used as the parent strain in this example, strains having similar properties can be constructed using the *C. glutamicum* ATCC 13032 strain or the *B. lactofermentum* ATCC 13869 strain as parent strain.

First, a plasmid pBS3ΔsucA47 for deleting odhA was constructed. PCR was performed using the synthetic DNA shown in SEQ ID NO: 48 and the synthetic DNA shown in SEQ ID NO: 49 as primers and the chromosomal DNA of *B. flavum* ATCC 14067 as the template to prepare an N-terminal side fragment. In a similar manner, a C-terminal side fragment was prepared using the synthetic DNAs of SEQ ID NOS: 50 and 51 as primers. Then, PCR was performed using a mixture of equal amounts of the N-terminal and C-terminal side fragments as the template and the synthetic DNAs of SEQ ID NOS: 52 and 53 (BamHI sequence was added) as the primers to obtain a fragment of the odhA from which coding region was deleted. The obtained mutant odhA fragment was treated with BamHI, and inserted into pBS3 (International Patent Publication WO2006/070944) at the BamHI site, and the obtained plasmid was designated as pBS3ΔsucA47.

pBS3ΔsucA47 was introduced into the *B. flavum* ATCC 14067 strain by the electric pulse method, and the cells were applied to the CM-Dex agar medium (5 g/l of glucose, 10 g/l of polypeptone, 10 g/l of yeast extract, 1 g/l of $KH_2PO_4$, 0.4 g/l of $MgSO_4 \cdot 7H_2O$, 0.01 g/l of $FeSO_4 \cdot 7H_2O$, 0.01 g/l of $MnSO_4 \cdot 4\text{-}5H_2O$, 3 g/l of urea, 1.2 g/l of soy protein hydrolysis solution, and 20 g/l of agar, adjusted to pH 7.5 with NaOH, autoclaved at 120° C. for 20 minutes) containing 25 μg/ml of kanamycin. The strain which grew after the culture performed at 31.5° C. for two days was designated as ATCC14067-pBS3ΔsucA strain in which pBS3ΔsucA47 was inserted into the chromosome. Then, the ATCC14067-pBS3ΔsucA strain was cultured overnight in the CM-Dex liquid medium, the obtained suspension was applied on the S10 agar medium (100 g/l of sucrose, 10 g/l of polypeptone, 10 g/l of yeast extract, 1 g/l of $KH_2PO_4$, 0.4 g/l of $MgSO_4 \cdot 7H_2O$, 0.01 g/l of $FeSO_4 \cdot 7H_2O$, 0.01 g/l of $MnSO_4 \cdot 4\text{-}5H_2O$, 3 g/l of urea, 1.2 g/l of soy protein hydrolysis solution, and 20 g/l of agar, adjusted to pH 7.5 with NaOH, autoclaved at 120° C. for 20 minutes), and culture was performed at 31.5° C. Among the emerged colonies, strains that were kanamycin sensitive were selected, and further purified on the CM-Dex agar medium. Chromosomal DNAs were prepared from these strains, PCR was performed with the synthetic DNAs of SEQ ID NOS: 52 and 53 as primers, and a strain for which an amplification fragment of about 1.9 kb was confirmed was designated as 8L3 strain.

PCR was performed using chromosomal DNA of the 8L3 strain as the template and the synthetic DNAs of SEQ ID NOS: 54 and 55 (SacI sequence was added) as primers, and the sequence of the obtained amplification fragment was determined. As a result, it was revealed that the alanine at position 111 of SEQ ID NO: 57 was replaced with threonine. That is, 8L3 was a double-mutant strain in which the above mutation was inadvertently introduced at the time of the introduction of the odhA deficiency. As a strain having the same yggB mutation as that of 8L3, the ATCC14067yggB8 strain is known (International Patent Publication WO2006/070944). By introducing pBS3ΔsucA47 into the ATCC14067yggB strain and performing the aforementioned steps, an odhA-deficient strain having the same yggB mutation as that of 8L3 can be constructed.

Then, a plasmid pBS4gdh3 for introducing a mutation into the promoter region of gdh was constructed. PCR was performed using the synthetic DNA shown in SEQ ID NO: 60 and the synthetic DNA shown in SEQ ID NO: 61 as primers and chromosomal DNA of the *B. lactofermentum* ATCC 13869 strain as the template to obtain an N-terminal side fragment. In a similar manner, a C-terminal side fragment was prepared using the synthetic DNAs of SEQ ID NOS: 62 and 63 as primers. Then, PCR was performed using a mixture of equal amounts of the N-terminal and C-terminal side fragments as the template and the synthetic DNAs of SEQ ID NOS: 64 and 65 (SmaI sequence was added) as primers to obtain a fragment of the gdh gene in which a mutation was introduced into the promoter region. The obtained mutant gdh fragment was treated with SmaI, and inserted into pBS4S (International Patent Publication WO2006/070944) at the SmaI site, and the obtained plasmid was designated as pBS4gdh3.

pBS4gdh3 was introduced into the 8L3 strain by the electric pulse method, and the cells were applied to the CM-Dex agar medium containing 25 μg/ml of kanamycin. The strain which grew after the culture performed at 31.5° C. for three days was isolated as 8L3-pBS4gdh3 strain in which pBS4gdh3 was inserted into the chromosome. Then, the 8L3-pBS4gdh3 strain was cultured overnight in the CM-Dex liquid medium, the obtained suspension was applied on the S10 agar medium, and culture was performed at 31.5° C. Among the colonies which emerged, strains having kanamycin sensitivity were selected, and further purified on the CM-Dex agar medium. Chromosomal DNAs were prepared from these strains, and an upstream coding region sequence of gdh was determined. A strain having the sequence shown in SEQ ID NO: 66 was designated as 8L3G strain.

(2) Construction of SDH-Deficient Strain

A plasmid pBS3Δsdh47 for deleting sdhA was constructed. PCR was performed using the synthetic DNA shown in SEQ ID NO: 67 and the synthetic DNA shown in SEQ ID NO: 68 as primers and the chromosomal DNA of *B. flavum* ATCC 14067 as the template to prepare an N-terminal side fragment. In a similar manner, a C-terminal side fragment was prepared using the synthetic DNAs of SEQ ID NOS: 69 and 70 as primers. Then, PCR was performed using a mixture of equal amounts of the N-terminal and C-terminal side fragments as the template and the synthetic DNAs of SEQ ID NOS: 71 and 72 as primers to obtain a fragment of the sdhA from which coding region was deleted. The obtained mutant sdhA fragment was treated with BamHI, and inserted into pBS3 (International Patent Publication WO2006/070944) at the BamHI site, and the obtained plasmid was designated as pBS3ΔsdhA47.

pBS3ΔsdhA47 was introduced into the 8L3G strain by the electric pulse method, and the cells were applied to the CM-Dex agar medium containing 25 μg/ml of kanamycin. The strain which grew after the culture performed at 31.5° C. for two days was designated as 8L3G-pBS3ΔsdhA strain in which pBS3ΔsdhA47 was inserted into the chromosome. Then, the 8L3G-pBS3ΔsdhA strain was cultured overnight in the CM-Dex liquid medium, the obtained suspension was applied on the S10 agar medium, and culture was performed at 31.5° C. Among the colonies which emerged, strains that were kanamycin sensitive were selected, and further purified on the CM-Dex agar medium. Chromosomal DNAs were prepared from these strains, PCR was performed with the synthetic DNAs of SEQ ID NOS: 71 and 72 (BamHI sequence was added) as primers, and a strain for which an amplification fragment of about 1 kb was confirmed was designated as 8L3GΔSDH strain.

(6) Evaluation of L-Glutamic Acid-Producing Ability of sdhA Deficient Strain and sucAsdhA Double Deficient Strain Then, in order to evaluate L-glutamic acid-producing ability of the 8L3G strain and the SDH-deficient strain thereof obtained as described above, the 8L3GΔSDH strain, each of these strains was cultured overnight on one CM-Dex plate medium, and then the total amount of the cells were scraped, inoculated into 300 mL of a medium having the composition shown below contained in a jar, and cultured at 31.5° C. pH was controlled to be 7.2 using ammonia gas during the culture, and stirring for aeration was controlled so that dissolved oxygen concentration is maintained to be 5% or higher. As shown in Table 2, the results were that the sucAsdhA double deficient strain, 8L3GΔSDH, showed a higher production rate of glutamic acid as compared to the sucA single deficient strain, 8L3G, and the L-glutamic acid accumulation obtained with the 8L3GΔSDH strain after the culture for 12.5 hours was 19 g/L, which markedly exceeded 16.5 g/L obtained with the sucA single deficient strain, the 8L3G strain. These results demonstrated that deficiency of both sucA and sdhA is effective for L-glutamic acid production also in coryneform bacteria.

Composition of Medium for Evaluation of L-Glutamic Acid Production:

| | |
|---|---|
| Glucose | 60 g/L |
| MgSO$_4$•7H$_2$O | 0.9 g/L |
| H$_3$PO$_4$ | 1.54 g/L |
| KOH | 1.45 g/L |
| FeSO$_4$•7H$_2$O | 10 mg/L |
| Soybean hydrolysate | 1.54 g (as nitrogen)/L |
| Biotin | 3.2 mg/L |
| VB1 | 0.67 mg/L |
| DL-Methionine | 0.28 g/L |

The medium was adjusted to pH 4.0 with aqueous ammonia, then sterilized at 120° C. for 15 minutes, further adjusted to pH 7.2 with ammonia gas immediately before the culture, and used for the culture.

TABLE 2

| | OD620 nm | Glu (g/L) |
|---|---|---|
| 8L3G | 36.4 | 16.5 |
| 8L3GΔSDH | 43.4 | 19.0 |

Explanation of Sequence Listing:

SEQ ID NO: 1: Nucleotide sequence of sdh operon of *Pantoea ananatis* (amino acid sequences of SDHD, SDHA and SDHB are also shown)
  sdhC: 527-913
  sdhD: 910-1254
  sdhA: 1258-3021
  sdhB: 3039-3752
SEQ ID NO: 2: Amino acid sequence of SDHD
SEQ ID NO: 3: Amino acid sequence of SDHA
SEQ ID NO: 4: Amino acid sequence of SDHB
SEQ ID NO: 5: Nucleotide sequence of sdh operon of *Pantoea ananatis* (amino acid sequence of SDHC is also shown)
SEQ ID NO: 6: Amino acid sequence of SDHC
SEQ ID NO: 7: Nucleotide sequences of α-KGDH subunit genes and neighboring genes of *Pantoea ananatis*
  sdhB: 2-121
  sucA: 322-3129
  sucB: 3145-4368
  sucC: 4437-4556
SEQ ID NO: 8: Amino acid sequence of succinate dehydrogenase iron-sulfur protein (part)
SEQ ID NO: 9: Amino acid sequence of α-KGDH E1o subunit
SEQ ID NO: 10: Amino acid sequence of α-KGDH E2o subunit
SEQ ID NO: 11: Part of succinyl-CoA synthetase β subunit
SEQ ID NO: 12: Nucleotide sequence of odhA gene of *Brevibacterium lactofermentum*
SEQ ID NO: 13: Amino acid sequence of E1o subunit encoded by odhA
SEQ ID NO: 14: Nucleotide sequence of gene encoding E2o subunit of *Brevibacterium lactofermentum* (NCgl2126 of GenBank Accession No. NC_003450)
SEQ ID NO: 15: Amino acid sequence of E2o subunit encoded by NCgl2126
SEQ ID NO: 16: Nucleotide sequence of hisD gene of *Pantoea ananatis*
SEQ ID NO: 17: Primer for amplification of fragment for integration of Km$^r$ gene into hisD gene
SEQ ID NO: 18: Primer for amplification of fragment for integration of Km$^r$ gene into hisD gene
SEQ ID NO: 19: Primer for cat gene amplification
SEQ ID NO: 20: Primer for cat gene amplification
SEQ ID NO: 21: Primer for sacB gene amplification
SEQ ID NO: 22: Primer for sacB gene amplification
SEQ ID NO: 23: Primer for amplification of DNA fragment containing P$_{lacUV5}$ promoter
SEQ ID NO: 24: Primer for amplification of DNA fragment containing P$_{lacUV5}$ promoter
SEQ ID NO: 25: Primer for amplification of DNA fragment containing λRedαβγ genes and tL3
SEQ ID NO: 26: Primer for amplification of DNA fragment containing λRedαβγ genes and tL3
SEQ ID NO: 27: Primer for amplification of DNA fragment containing P$_{lacUV5}$ promoter and TrrnB
SEQ ID NO: 28: Primer for amplification of DNA fragment containing P$_{lacUV5}$ promoter and TrrnB
SEQ ID NO: 29: Primer for attL amplification
SEQ ID NO: 30: Primer for attL amplification
SEQ ID NO: 31: Nucleotide sequence of attL
SEQ ID NO: 32: Primer for attR amplification
SEQ ID NO: 33: Primer for attR amplification
SEQ ID NO: 34: Nucleotide sequence of attR
SEQ ID NO: 35: Primer for amplification of DNA fragment containing bla gene
SEQ ID NO: 36: Primer for amplification of DNA fragment containing bla gene
SEQ ID NO: 37: Primer for amplification of DNA fragment containing ter_rrnB
SEQ ID NO: 38: Primer for amplification of DNA fragment containing ter_rrnB
SEQ ID NO: 39: Nucleotide sequence of DNA fragment containing ter_thrL terminator
SEQ ID NO: 40: Primer for amplification of DNA fragment containing ter_thrL terminator SEQ ID NO: 41: Primer for amplification of DNA fragment containing ter_thrL terminator
SEQ ID NO: 42: Primer for amplification of moieties of gltA gene other than ORF
SEQ ID NO: 43: Primer for amplification of moieties of gltA gene other than ORF
SEQ ID NO: 44: Primer for prpC gene amplification
SEQ ID NO: 45: Primer for prpC gene amplification
SEQ ID NO: 46: Primer for amplification of DNA fragment for sdhA disruption
SEQ ID NO: 47: Primer for amplification of DNA fragment for sdhA disruption
SEQ ID NO: 48: Primer for amplification of sucA gene upstream fragment
SEQ ID NO: 49: Primer for amplification of sucA gene upstream fragment
SEQ ID NO: 50: Primer for amplification of sucA gene downstream fragment
SEQ ID NO: 51: Primer for amplification of sucA gene downstream fragment
SEQ ID NO: 52: Primer for sucA gene amplification
SEQ ID NO: 53: Primer for sucA gene amplification
SEQ ID NO: 54: Primer for yggB gene amplification
SEQ ID NO: 55: Primer for yggB gene amplification
SEQ ID NO: 56: Nucleotide sequence of yggB gene
SEQ ID NO: 57: Amino acid sequence of YggB
SEQ ID NO: 58: Nucleotide sequence of mutant yggB gene
SEQ ID NO: 59: Amino acid sequence of mutant YggB
SEQ ID NO: 60: Primer for amplification of gdh gene upstream region (mutation is introduced)
SEQ ID NO: 61: Primer for amplification of gdh gene upstream region
SEQ ID NO: 62: Primer for amplification of gdh gene downstream region
SEQ ID NO: 63: Primer for amplification of gdh gene downstream region (mutation is introduced)
SEQ ID NO: 64: Primer for gdh gene amplification
SEQ ID NO: 65: Primer for gdh gene amplification
SEQ ID NO: 66: Nucleotide sequence of upstream coding region of mutant gdh gene
SEQ ID NO: 67: Primer for amplification of sdhA gene upstream region
SEQ ID NO: 68: Primer for amplification of sdhA gene upstream region (mutation is introduced)
SEQ ID NO: 69: Primer for amplification of sdhA gene downstream region
SEQ ID NO: 70: Primer for amplification of sdhA gene downstream region (mutation is introduced)
SEQ ID NO: 71: Primer for sdhA gene amplification
SEQ ID NO: 72: Primer for sdhA gene amplification
SEQ ID NO: 73: Nucleotide sequence of sdh operon of *C. glutamicum* ATCC 13032 (amino acid sequences of SDHC, SDHA and SDHB are also shown)
  sdhC: 449-1219
  sdhA: 1239-3257
  sdhB: 3260-4006
SEQ ID NO: 74: Amino acid sequence of SDHC
SEQ ID NO: 75: Amino acid sequence of SDHA
SEQ ID NO: 76: Amino acid sequence of SDAB
SEQ ID NO: 77: Nucleotide sequence of sdh operon of *B. lactofermentum* ATCC 13869 (amino acid sequences of SDHC, SDHA and SDHB are also shown)
  sdhC: 449-1219
  sdhA: 1239-3257
  sdhB: 3260-4006
SEQ ID NO: 78: Amino acid sequence of SDHC
SEQ ID NO: 79: Amino acid sequence of SDHA
SEQ ID NO: 80: Amino acid sequence of SDHB

INDUSTRIAL APPLICABILITY

According to the method of the present invention, L-amino acids such as L-glutamic acid can be efficiently produced by fermentation.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid, the method comprising:
culturing in a medium a bacterium belonging to the genus *Escherichia* or *Pantoea*, or a coryneform bacterium, and collecting the L-amino acid from the medium or bacterial cells;
wherein said bacterium is able to produce an L-amino acid, and the activities of succinate dehydrogenase and α-ketoglutarate dehydrogenase are decreased in said bacterium by disrupting the genes encoding for succinate dehydrogenase and α-ketoglutarate dehydrogenase on the chromosome of the bacterium;
wherein the gene encoding succinate dehydrogenase is selected from the group consisting of the sdhA gene, the sdhB gene, the sdhC gene and the sdhD gene, and combinations thereof;
wherein the sdhA gene is selected from the group consisting of:
(a) a DNA comprising the nucleotide sequence of nucleotides 1258 to 3021 in SEQ ID NO: 1, and
(b) a DNA which is able to hybridize to a DNA comprising a sequence fully complementary to the entire nucleotide sequence of nucleotides 1258 to 3021 in SEQ ID NO: 1 under stringent conditions comprising washing at 0.1× SSC, 0.1% SDS at 60°;
wherein the sdhB gene is selected from the group consisting of:
(c) a DNA comprising the nucleotide sequence of nucleotides 3039 to 3752 in SEQ ID NO: 1, and
(d) a DNA which is able to hybridize to a DNA comprising a sequence fully complementary to the entire nucleotide sequence of nucleotides 3039 to 3752 in SEQ ID NO: 1 under stringent conditions comprising washing at 0.1× SSC, 0.1% SDS at 60° C.;
wherein the sdhC gene is selected from the group consisting of:
(e) a DNA comprising the nucleotide sequence of nucleotides 527 to 913 in SEQ ID NO: 1, and
(f) a DNA which is able to hybridize to a DNA comprising a sequence fully complementary to the entire nucleotide sequence of nucleotides 527 to 913 in SEQ ID NO: 1 under stringent conditions comprising washing at 0.1× SSC, 0.1% SDS at 60° C.; and
wherein the sdhD gene is selected from the group consisting of:
(g) a DNA comprising the nucleotide sequence of nucleotides 910 to 1254 in SEQ ID NO: 1, and
(h) a DNA which is able to hybridize to a DNA comprising a sequence fully complementary to the entire nucleotide sequence of nucleotides 910 to 1254 in SEQ ID NO: 1 under stringent conditions comprising washing at 0.1× SSC, 0.1% SDS at 60° C.

2. The method according to claim 1, wherein the gene encoding α-ketoglutarate dehydrogenase is selected from the group consisting of the sucA gene, the odhA gene and the sucB gene, and combinations thereof; and wherein the sucA gene is selected from the group consisting of:
(a) a DNA comprising the nucleotide sequence of nucleotides 322 to 3129 in SEQ ID NO: 7, and
(b) a DNA which is able to hybridize to a DNA comprising a sequence fully complementary to the entire nucleotide sequence of nucleotides 322 to 3129 in SEQ ID NO: 7 under stringent conditions comprising washing at 0.1× SSC, 0.1% SDS at 60° C.

3. The method according to claim 1, wherein the L-amino acid is L-glutamic acid or an L-amino acid which is biosynthesized via L-glutamic acid as a precursor.

4. The method according to claim 3, wherein the L-amino acid is selected from the group consisting of L-arginine, L-proline, L-ornithine, L-citrulline, and L-glutamine.

5. The method according to claim 1, wherein the bacterium is *Escherichia coli, Pantoea ananatis*, or *corynebacterium glutamicum*.

6. The method according to claim 1,
wherein the sdhA gene encodes a protein selected from the group consisting of:
(A) a protein comprising the amino acid sequence of SEQ ID NO: 3; and
(B) a protein comprising the amino acid sequence of SEQ ID NO: 3, but which includes substitutions, deletions, insertions, or additions of one to 5 amino acid residues;
wherein the sdhB gene encodes a protein selected from the group consisting of:
(C) a protein comprising the amino acid sequence of SEQ ID NO: 4; and
(D) a protein comprising the amino acid sequence of SEQ ID NO: 4, but which includes substitutions, deletions, insertions, or additions of one to 5 amino acid residues;
wherein the sdhC gene encodes a protein selected from the group consisting of:
(E) a protein comprising the amino acid sequence of SEQ ID NO: 6; and
(F) a protein comprising the amino acid sequence of SEQ ID NO: 6, but which includes substitutions, deletions, insertions, or additions of one to 5 amino acid residues; and
wherein the sdhD gene encodes a protein selected from the group consisting of:
(G) a protein comprising the amino acid sequence of SEQ ID NO: 2; and
(H) a protein comprising the amino acid sequence of SEQ ID NO: 2 but which includes substitutions, deletions, insertions, or additions of one to 5 amino acid residues.

7. The method according to claim 2, wherein the sucA gene encodes a protein selected from the group consisting of:
(A) a protein comprising the amino acid sequence of SEQ ID NO: 9; and
(B) a protein comprising the amino acid sequence of SEQ ID NO: 9, but which includes substitutions, deletions, insertions, or additions of one to 5 amino acid residues.

* * * * *

UNITED STATES PATENT AND TRADEMARK OFFICE
CERTIFICATE OF CORRECTION

| | |
|---|---|
| PATENT NO. | : 8,058,035 B2 |
| APPLICATION NO. | : 12/478049 |
| DATED | : November 15, 2011 |
| INVENTOR(S) | : Hara et al. |

It is certified that error appears in the above-identified patent and that said Letters Patent is hereby corrected as shown below:

Col. 159 Line 1-53 claim 1 should read

1. A method for producing an L-amino acid, the method comprising:
culturing in a medium a bacterium belonging to the genus *Escherichia* or *Pantoea*, or a coryneform bacterium, and
  collecting the L-amino acid from the medium or bacterial cells;
  wherein said bacterium is able to produce an L-amino acid, and the activities of succinate dehydrogenase and α-ketoglutarate dehydrogenase are decreased in said bacterium by disrupting the genes encoding for succinate dehydrogenase and α-ketoglutarate dehydrogenase on the chromosome of the bacterium;
  wherein the gene encoding succinate dehydrogenase is selected from the group consisting of the *sdhA* gene, the *sdhB* gene, the *sdhC* gene and the *sdhD* gene, and combinations thereof;
wherein the *sdhA* gene is selected from the group consisting of:
  (a) a DNA comprising the nucleotide sequence of nucleotides 1258 to 3021 in SEQ ID NO: 1, and
  (b) a DNA which is able to hybridize to a DNA comprising a sequence fully complementary to the entire nucleotide sequence of nucleotides 1258 to 3021 in SEQ ID NO: 1 under stringent conditions comprising washing at 0.1 × SSC, 0.1% SDS at 60°;
wherein the *sdhB* gene is selected from the group consisting of:
  (c) a DNA comprising the nucleotide sequence of nucleotides 3039 to 3752 in SEQ ID NO: 1, and
  (d) a DNA which is able to hybridize to a DNA comprising a sequence fully complementary to the entire nucleotide sequence of nucleotides 3039 to 3752 in SEQ ID NO: 1 under stringent conditions comprising washing at 0.1 × SSC, 0.1% SDS at 60°C;
wherein the *sdhC* gene is selected from the group consisting of:
  (e) a DNA comprising the nucleotide sequence of nucleotides 527 to 913 in SEQ ID NO: 1, and
  (f) a DNA which is able to hybridize to a DNA comprising a sequence fully complementary to the entire nucleotide sequence of nucleotides 527 to 913 in SEQ ID NO: 1 under stringent conditions comprising washing at 0.1 × SSC, 0.1% SDS at 60°C; and Signed and Sealed this
First Day of May, 2012

David J. Kappos
*Director of the United States Patent and Trademark Office*

CERTIFICATE OF CORRECTION (continued)
U.S. Pat. No. 8,058,035 B2

Cont. Col. 159 Line 1-53 claim 1 should read
    wherein the *sdhD* gene is selected from the group consisting of:
    (g)    a DNA comprising the nucleotide sequence of nucleotides 910 to 1254 in SEQ ID NO: 1, and
    (h)    a DNA which is able to hybridize to a DNA comprising a sequence fully complementary to the entire nucleotide sequence of nucleotides 910 to 1254 in SEQ ID NO: 1 under stringent conditions comprising washing at 0.1 × SSC, 0.1% SDS at 60°C.

Col. 159 claim 2 Line 54 - Col. 160 Line 9 should read
    2.    The method according to claim 1, wherein the gene encoding α-ketoglutarate dehydrogenase is selected from the group consisting of the *sucA* gene, the *odhA* gene and the *sucB* gene, and combinations thereof; and
    wherein the *sucA* gene is selected from the group consisting of:
    (a)    a DNA comprising the nucleotide sequence of nucleotides 322 to 3129 in SEQ ID NO: 7, and
    (b)    a DNA which is able to hybridize to a DNA comprising a sequence fully complementary to the entire nucleotide sequence of nucleotides 322 to 3129 in SEQ ID NO: 7 under stringent conditions comprising washing at 0.1 × SSC, 0.1% SDS at 60°C.

Col. 160 claim 6 Line 19 - 48 should read
    6.    The method according to claim 1,
    wherein the *sdhA* gene encodes a protein selected from the group consisting of:
    (A)    a protein comprising the amino acid sequence of SEQ ID NO: 3; and
    (B)    a protein comprising the amino acid sequence of SEQ ID NO: 3, but which includes substitutions, deletions, insertions, or additions of one to 5 amino acid residues;
    wherein the *sdhB* gene encodes a protein selected from the group consisting of:
    (C)    a protein comprising the amino acid sequence of SEQ ID NO: 4; and
    (D)    a protein comprising the amino acid sequence of SEQ ID NO: 4, but which includes substitutions, deletions, insertions, or additions of one to 5 amino acid residues;
    wherein the *sdhC* gene encodes a protein selected from the group consisting of:
    (E)    a protein comprising the amino acid sequence of SEQ ID NO: 6; and
    (F)    a protein comprising the amino acid sequence of SEQ ID NO: 6, but which includes substitutions, deletions, insertions, or additions of one to 5 amino acid residues; and
    wherein the *sdhD* gene encodes a protein selected from the group consisting of:
    (G)    a protein comprising the amino acid sequence of SEQ ID NO: 2; and
    (H)    a protein comprising the amino acid sequence of SEQ ID NO: 2 but which includes substitutions, deletions, insertions, or additions of one to 5 amino acid residues.

Col. 160 claim 7 Line 49 - 56 should read
    7.    The method according to claim 4, wherein the *sucA* gene encodes a protein selected from the group consisting of:
    (A)    a protein comprising the amino acid sequence of SEQ ID NO: 9; and
    (B)    a protein comprising the amino acid sequence of SEQ ID NO: 9, but which includes substitutions, deletions, insertions, or additions of one to 5 amino acid residues.

SEQUENCE LISTING

```
<160> NUMBER OF SEQ ID NOS: 80

<210> SEQ ID NO 1
<211> LENGTH: 3944
<212> TYPE: DNA
<213> ORGANISM: Pantoea ananatis
<220> FEATURE:
<221> NAME/KEY: CDS
<222> LOCATION: (910)..(1254)
<220> FEATURE:
<221> NAME/KEY: CDS
<222> LOCATION: (1258)..(3021)
<220> FEATURE:
<221> NAME/KEY: CDS
<222> LOCATION: (3039)..(3752)

<400> SEQUENCE: 1
tataagcagt gaagggtaca gagtgagagg cgcgttccac aggaaatgta aagccgtgac      60
atgtgcatat cgcggttgtt aaagatccgg tcaggacata acttctttgt aaccaataac     120
ctgatggttt taaaagctgt tagtggcaat gttacataac ttgagcttag gagaaagtgt     180
atccccataa cttttgtgca tcataggatt ttatcgggat agtttgtaac tgaattgttg     240
```

```
aactattgtc aaatcagata attaaatttg tatgaattgt gaaaaacgtg agaatgatca      300
ctgttccacc caaaattctc caaagagttt gtagggggaat tgtaatcaga atgtgatcgt     360
cctatacttc cggccaggtc tccggaatac cctgacacca ggagccaccc agcgtttgta      420
acacgtcatt taacactgga tgttgctatt ttggtgacgg ataaagtctg aacacgttta      480
gggttcaggt cttatgtccg gaggaagcaa aataaaaaag agctgtgtgg gcaaaaccgt      540
gaaaaaacaa agacctgtca acttggatct ctcgacgatc cggtttcccg ttactgcaat      600
atcgtccatt cttcaccgcg tctccggcgt catcaccctg gttgctctcg catcctgtt       660 atggcttctc ggtctttccc tctcttctcc tgaaggtttc cagcacgctg catctgtcat      720
gaatggcttc tttgcgaagt tcatcatgtg gggcattttg actgcgctgg cctatcatgc      780
agtgggcggg atacgtcata tgttaatgga ttttggttat ctggccgaaa cgctcgaagc      840
aggtaagcgt tctgcgcagg tgacgtttgg tattactgtc gtgctttcaa ttttagcagg      900
```

| | | | |
|---|---|---|---|
| agtcctcgt atg gta agc aat gca tcc gcg ttg ggt cgc aat ggc att cag | | | 951 |
| Met Val Ser Asn Ala Ser Ala Leu Gly Arg Asn Gly Ile Gln | | | |
| 1 5 10 | | | |

```
gac tgg ctg ctg ctg cgc gcg acg gca atc ctc atc acg ctt tac atc      999
Asp Trp Leu Leu Leu Arg Ala Thr Ala Ile Leu Ile Thr Leu Tyr Ile
15              20                  25                  30 atc tat ctc ctc ggt ttc gtg gtg atg aca gac acg ctg acg tat gac     1047
Ile Tyr Leu Leu Gly Phe Val Val Met Thr Asp Thr Leu Thr Tyr Asp
                35                  40                  45 atc tgg cgt ggc ttc ttc gct tct gca ttt aca aaa gtg ttc acg ctc     1095
Ile Trp Arg Gly Phe Phe Ala Ser Ala Phe Thr Lys Val Phe Thr Leu
            50                  55                  60 ctg acg ctg ttt tcc att ctg atc cac ggc tgg atc ggt atg tgg cag     1143
Leu Thr Leu Phe Ser Ile Leu Ile His Gly Trp Ile Gly Met Trp Gln
        65                  70                  75 gtc tta acg gac tac gtt aaa ccg ctg gca acg cgt ctg ctg ttg cag     1191
Val Leu Thr Asp Tyr Val Lys Pro Leu Ala Thr Arg Leu Leu Leu Gln
    80                  85                  90 ttg gtc atc gta gtg gcg ctg ttg tca tat gca att tat gga ttt gtt     1239
Leu Val Ile Val Val Ala Leu Leu Ser Tyr Ala Ile Tyr Gly Phe Val
95                  100                 105                 110 gtg gtg tgg ggt gtg taa atg agt tta cca gta aga gaa ttt gat gcc     1287
Val Val Trp Gly Val     Met Ser Leu Pro Val Arg Glu Phe Asp Ala
                115                 120                 125 gtg gtg atc ggc gca ggc ggc gcg ggt atg cgc gcg gcg ttg caa atc     1335
Val Val Ile Gly Ala Gly Gly Ala Gly Met Arg Ala Ala Leu Gln Ile
            130                 135                 140 tcc cag tcg ggc cag acc tgt gcc ctg ttg tcc aaa gtc ttc ccg acc     1383
Ser Gln Ser Gly Gln Thr Cys Ala Leu Leu Ser Lys Val Phe Pro Thr
        145                 150                 155 cgt tcc cat acg gtc tcc gcg cag ggc gga atc acc gtt gcg ctg ggt     1431
Arg Ser His Thr Val Ser Ala Gln Gly Gly Ile Thr Val Ala Leu Gly
    160                 165                 170 aac acc cat gac gat aac tgg gaa tgg cat atg tat gac acc gtc aaa     1479
Asn Thr His Asp Asp Asn Trp Glu Trp His Met Tyr Asp Thr Val Lys
175                 180                 185 ggt tcc gac tac atc ggt gac cag gac gcg atc gaa tac atg tgt cac     1527
Gly Ser Asp Tyr Ile Gly Asp Gln Asp Ala Ile Glu Tyr Met Cys His
190                 195                 200                 205 gtc ggt ccg gaa gcg att ctg gaa ctg gag cac atg ggc ttg ccc ttc     1575
Val Gly Pro Glu Ala Ile Leu Glu Leu Glu His Met Gly Leu Pro Phe
            210                 215                 220
```

```
tcc cgt ctt gat gac ggc cgc gtt tat cag cgt ccg ttt ggt ggt cag   1623
Ser Arg Leu Asp Asp Gly Arg Val Tyr Gln Arg Pro Phe Gly Gly Gln
            225                 230                 235 tcg aaa aac ttc ggc ggt gag cag gcg gcg cgt act gcc gca gcg gcc   1671
Ser Lys Asn Phe Gly Gly Glu Gln Ala Ala Arg Thr Ala Ala Ala Ala
        240                 245                 250 gac cgt acc ggc cac gca ctg ctg cat acg ctg tat cag cag aac ctg   1719
Asp Arg Thr Gly His Ala Leu Leu His Thr Leu Tyr Gln Gln Asn Leu
    255                 260                 265 aaa aat aaa acc act atc ttc tcc gaa tgg tat gca ctg gat ctg gtc   1767
Lys Asn Lys Thr Thr Ile Phe Ser Glu Trp Tyr Ala Leu Asp Leu Val
270                 275                 280                 285 aaa aat gac gac ggt gcc atc gta ggc tgt acg gca atc tgc atg gaa   1815
Lys Asn Asp Asp Gly Ala Ile Val Gly Cys Thr Ala Ile Cys Met Glu
                290                 295                 300 acc ggc gaa acg gtt tac ttc aaa gcc aag gcc acc att ctg gcg acg   1863
Thr Gly Glu Thr Val Tyr Phe Lys Ala Lys Ala Thr Ile Leu Ala Thr
            305                 310                 315 ggc ggt gca gga cgt att tat cag tcc acg acg aac gcc cac atc aat   1911
Gly Gly Ala Gly Arg Ile Tyr Gln Ser Thr Thr Asn Ala His Ile Asn
        320                 325                 330 acc ggc gac ggt gtt ggc atg gcg ctg cgc gcg ggc gtg cct gtg cag   1959
Thr Gly Asp Gly Val Gly Met Ala Leu Arg Ala Gly Val Pro Val Gln
    335                 340                 345 gat atg gaa atg tgg cag ttc cac cca acc ggt atc gcc ggt gct ggt   2007
Asp Met Glu Met Trp Gln Phe His Pro Thr Gly Ile Ala Gly Ala Gly
350                 355                 360                 365 gta ctg gtc acc gaa ggc tgt cgt ggt gaa ggc ggt tat ctg ctg aac   2055
Val Leu Val Thr Glu Gly Cys Arg Gly Glu Gly Gly Tyr Leu Leu Asn
                370                 375                 380 aaa cac ggt gag cgt ttc atg gag cgc tat gcg cct aac gcc aaa gac   2103
Lys His Gly Glu Arg Phe Met Glu Arg Tyr Ala Pro Asn Ala Lys Asp
            385                 390                 395 ctt gcc ggt cgt gac gtt gtg gcc cgt tcg atg atg gtg gag atc cgt   2151
Leu Ala Gly Arg Asp Val Val Ala Arg Ser Met Met Val Glu Ile Arg
        400                 405                 410 gaa ggt cgt ggt tgc gac ggt cca tgg ggc ccg cac atc aag ctg aaa   2199
Glu Gly Arg Gly Cys Asp Gly Pro Trp Gly Pro His Ile Lys Leu Lys
    415                 420                 425 ctc gat cac ctg ggt gcg gaa gtg ctg gaa tcg cgc ctg ccg ggc atc   2247
Leu Asp His Leu Gly Ala Glu Val Leu Glu Ser Arg Leu Pro Gly Ile
430                 435                 440                 445 ctt gag ctg tcc cgt acc ttt gct cac gtt gac ccg att aaa gag ccg   2295
Leu Glu Leu Ser Arg Thr Phe Ala His Val Asp Pro Ile Lys Glu Pro
                450                 455                 460 att ccg gtt atc cca acc tgt cac tac atg atg ggc ggc gtg cca acc   2343
Ile Pro Val Ile Pro Thr Cys His Tyr Met Met Gly Gly Val Pro Thr
            465                 470                 475 aaa gtc acc ggt cag gcg ctg cgt gta aat gag cag ggc gaa gat gaa   2391
Lys Val Thr Gly Gln Ala Leu Arg Val Asn Glu Gln Gly Glu Asp Glu
        480                 485                 490 gtg att cct ggc ctg ttc gcg gtg ggt gaa atc gcc tgc gta tcg gta   2439
Val Ile Pro Gly Leu Phe Ala Val Gly Glu Ile Ala Cys Val Ser Val
    495                 500                 505 cac ggg gcg aac cgt ctg ggt ggc aac tcg ctg ctg gac ctg gtg gtc   2487
His Gly Ala Asn Arg Leu Gly Gly Asn Ser Leu Leu Asp Leu Val Val
510                 515                 520                 525 ttc ggt cgc gcg gct ggc gtg cat ctg ctt gaa tgt ctg gaa gag cag   2535
Phe Gly Arg Ala Ala Gly Val His Leu Leu Glu Cys Leu Glu Glu Gln
                530                 535                 540
```

```
ggt gaa ctg cgt gaa gcc agc cag gaa aac att gat gcc gcg atg gcg    2583
Gly Glu Leu Arg Glu Ala Ser Gln Glu Asn Ile Asp Ala Ala Met Ala
            545                 550                 555 cgt ttc aac cgc tgg gaa aat aac acc acg ggt gaa gat ccg gtt gaa    2631
Arg Phe Asn Arg Trp Glu Asn Asn Thr Thr Gly Glu Asp Pro Val Glu
            560                 565                 570 atc cgc aag gcg ttg caa cgc tgc atg cag aac aac ttc tcg gta ttc    2679
Ile Arg Lys Ala Leu Gln Arg Cys Met Gln Asn Asn Phe Ser Val Phe
575                 580                 585 cgt gaa ggc gat gcg atg cgt gaa ggg ctt gct gaa ctg aaa gag atc    2727
Arg Glu Gly Asp Ala Met Arg Glu Gly Leu Ala Glu Leu Lys Glu Ile
590                 595                 600                 605 cgt gag cgt ctg aag tcc gcg cgc ctg gat gac cgc tca cct gac ttc    2775
Arg Glu Arg Leu Lys Ser Ala Arg Leu Asp Asp Arg Ser Pro Asp Phe
                610                 615                 620 aat aca cag cgt att gag tgc ctt gag ctg gat aac ctg atg gaa acc    2823
Asn Thr Gln Arg Ile Glu Cys Leu Glu Leu Asp Asn Leu Met Glu Thr
            625                 630                 635 gct tat gcc acc gca gtg gcg gcc aac tac cgc act gag agc cgt ggc    2871
Ala Tyr Ala Thr Ala Val Ala Ala Asn Tyr Arg Thr Glu Ser Arg Gly
            640                 645                 650 gca cac agt cgc ttc gac tat ccg gaa cgt gat gat gcc aac tgg ctg    2919
Ala His Ser Arg Phe Asp Tyr Pro Glu Arg Asp Asp Ala Asn Trp Leu
655                 660                 665 tgc cat agc ctc tat gtt ccg caa acg gaa agc atg acg cgc cgt gag    2967
Cys His Ser Leu Tyr Val Pro Gln Thr Glu Ser Met Thr Arg Arg Glu
670                 675                 680                 685 gtg aac atg caa ccg aaa ctg cgt gcc ttc ccg ccg aaa gcg cgt        3015
Val Asn Met Gln Pro Lys Leu Arg Ala Ala Phe Pro Pro Lys Ala Arg
                690                 695                 700 acc tac taattgcgga gatcatc atg aga ctt gaa ttt tcg atc tat cgt    3065
Thr Tyr                     Met Arg Leu Glu Phe Ser Ile Tyr Arg
                                705                 710 tac aac ccg gac gtc gat gac aaa ccg cgc atg cag gac tat acc ctg    3113
Tyr Asn Pro Asp Val Asp Asp Lys Pro Arg Met Gln Asp Tyr Thr Leu
            715                 720                 725 gaa gcg gaa gac ggc cgt gac atg atg ctg ctg gat gcg ctg atc cgt    3161
Glu Ala Glu Asp Gly Arg Asp Met Met Leu Leu Asp Ala Leu Ile Arg
730                 735                 740 ctg aaa gag aag gat cct acc ctg gcg ttt cgt cgc tca tgc cgt gaa    3209
Leu Lys Glu Lys Asp Pro Thr Leu Ala Phe Arg Arg Ser Cys Arg Glu
745                 750                 755                 760 ggc gtg tgc ggt tca gac ggc ctg aac atg aac ggg aaa aac ggc ctg    3257
Gly Val Cys Gly Ser Asp Gly Leu Asn Met Asn Gly Lys Asn Gly Leu
                765                 770                 775 gcc tgt atc acg ccg gtc tcg gcg tta ggc aac ggc aag cag aaa atc    3305
Ala Cys Ile Thr Pro Val Ser Ala Leu Gly Asn Gly Lys Gln Lys Ile
            780                 785                 790 gtt atc cgt cct cta ccg ggc ctg ccg gtc gtg cgc gac ctg gtg gtg    3353
Val Ile Arg Pro Leu Pro Gly Leu Pro Val Val Arg Asp Leu Val Val
            795                 800                 805 gac atg ggc cag ttt tat gcc cag tat gag aaa att aag cct ttc tta    3401
Asp Met Gly Gln Phe Tyr Ala Gln Tyr Glu Lys Ile Lys Pro Phe Leu
810                 815                 820 ttg aat aac ggt gaa aac ccg cca gcg cgt gag cat ctg cag tcg ccg    3449
Leu Asn Asn Gly Glu Asn Pro Pro Ala Arg Glu His Leu Gln Ser Pro
825                 830                 835                 840 ggc gag cgt gag cat ctg gac gga ttg tat gag tgt att ctc tgc gcc    3497
Gly Glu Arg Glu His Leu Asp Gly Leu Tyr Glu Cys Ile Leu Cys Ala
                845                 850                 855
```

```
tgt tgc tca acc tct tgc ccg tcg ttc tgg tgg aac ccg gac aag ttt     3545
Cys Cys Ser Thr Ser Cys Pro Ser Phe Trp Trp Asn Pro Asp Lys Phe
            860                 865                 870 att ggt cct gca ggc ctg ctg gcc gct tac cgc ttc ctg att gac agc     3593
Ile Gly Pro Ala Gly Leu Leu Ala Ala Tyr Arg Phe Leu Ile Asp Ser
        875                 880                 885 cgt gat acg gaa acg gat gcg cgt ctg gat aat ctg agc gat gca ttc     3641
Arg Asp Thr Glu Thr Asp Ala Arg Leu Asp Asn Leu Ser Asp Ala Phe
    890                 895                 900 agc gtt ttc cgc tgt cac agc atc atg aac tgt gta agt gtt tgt cct     3689
Ser Val Phe Arg Cys His Ser Ile Met Asn Cys Val Ser Val Cys Pro
905                 910                 915                 920 aaa ggg cta aac ccg acg cgc gct atc ggc cac att aag tcg atg ctg     3737
Lys Gly Leu Asn Pro Thr Arg Ala Ile Gly His Ile Lys Ser Met Leu
                925                 930                 935 ctg caa cgc agc gcg tagttatacc accgggaacc tcaggttccc ggtattttac     3792
Leu Gln Arg Ser Ala
            940 ggaagcctct gtaaacgcgg tcccaaccac gtttacaaag gttcccttac gggccgggcg   3852 cgcgctgcgc acagtgctcg tatcgctgaa ctcactacgg caaaccgcga aagcggcaac   3912 aaatgaaacc tcaaaaaagc ataacattgc tt                                 3944

<210> SEQ ID NO 2
<211> LENGTH: 115
<212> TYPE: PRT
<213> ORGANISM: Pantoea ananatis

<400> SEQUENCE: 2

Met Val Ser Asn Ala Ser Ala Leu Gly Arg Asn Gly Ile Gln Asp Trp
1               5                   10                  15

Leu Leu Leu Arg Ala Thr Ala Ile Leu Ile Thr Leu Tyr Ile Ile Tyr
            20                  25                  30

Leu Leu Gly Phe Val Val Met Thr Asp Thr Leu Thr Tyr Asp Ile Trp
        35                  40                  45

Arg Gly Phe Phe Ala Ser Ala Phe Thr Lys Val Phe Thr Leu Leu Thr
    50                  55                  60

Leu Phe Ser Ile Leu Ile His Gly Trp Ile Gly Met Trp Gln Val Leu
65                  70                  75                  80

Thr Asp Tyr Val Lys Pro Leu Ala Thr Arg Leu Leu Leu Gln Leu Val
                85                  90                  95

Ile Val Val Ala Leu Leu Ser Tyr Ala Ile Tyr Gly Phe Val Val Val
            100                 105                 110

Trp Gly Val
        115

<210> SEQ ID NO 3
<211> LENGTH: 588
<212> TYPE: PRT
<213> ORGANISM: Pantoea ananatis

<400> SEQUENCE: 3

Met Ser Leu Pro Val Arg Glu Phe Asp Ala Val Val Ile Gly Ala Gly
1               5                   10                  15

Gly Ala Gly Met Arg Ala Ala Leu Gln Ile Ser Gln Ser Gly Gln Thr
            20                  25                  30

Cys Ala Leu Leu Ser Lys Val Phe Pro Thr Arg Ser His Thr Val Ser
        35                  40                  45

Ala Gln Gly Gly Ile Thr Val Ala Leu Gly Asn Thr His Asp Asp Asn
```

```
              50                  55                  60
Trp Glu Trp His Met Tyr Asp Thr Val Lys Gly Ser Asp Tyr Ile Gly
 65                  70                  75                  80

Asp Gln Asp Ala Ile Glu Tyr Met Cys His Val Gly Pro Glu Ala Ile
                     85                  90                  95

Leu Glu Leu Glu His Met Gly Leu Pro Phe Ser Arg Leu Asp Asp Gly
                    100                 105                 110

Arg Val Tyr Gln Arg Pro Phe Gly Gly Gln Ser Lys Asn Phe Gly Gly
                    115                 120                 125

Glu Gln Ala Ala Arg Thr Ala Ala Ala Asp Arg Thr Gly His Ala
        130                 135                 140

Leu Leu His Thr Leu Tyr Gln Gln Asn Leu Lys Asn Lys Thr Thr Ile
145                 150                 155                 160

Phe Ser Glu Trp Tyr Ala Leu Asp Leu Val Lys Asn Asp Asp Gly Ala
                    165                 170                 175

Ile Val Gly Cys Thr Ala Ile Cys Met Glu Thr Gly Glu Thr Val Tyr
                    180                 185                 190

Phe Lys Ala Lys Ala Thr Ile Leu Ala Thr Gly Gly Ala Gly Arg Ile
                    195                 200                 205

Tyr Gln Ser Thr Thr Asn Ala His Ile Asn Thr Gly Asp Gly Val Gly
        210                 215                 220

Met Ala Leu Arg Ala Gly Val Pro Val Gln Asp Met Glu Met Trp Gln
225                 230                 235                 240

Phe His Pro Thr Gly Ile Ala Gly Ala Gly Val Leu Val Thr Glu Gly
                    245                 250                 255

Cys Arg Gly Glu Gly Gly Tyr Leu Leu Asn Lys His Gly Glu Arg Phe
                    260                 265                 270

Met Glu Arg Tyr Ala Pro Asn Ala Lys Asp Leu Ala Gly Arg Asp Val
                    275                 280                 285

Val Ala Arg Ser Met Met Val Glu Ile Arg Glu Gly Arg Gly Cys Asp
        290                 295                 300

Gly Pro Trp Gly Pro His Ile Lys Leu Lys Leu Asp His Leu Gly Ala
305                 310                 315                 320

Glu Val Leu Glu Ser Arg Leu Pro Gly Ile Leu Glu Leu Ser Arg Thr
                    325                 330                 335

Phe Ala His Val Asp Pro Ile Lys Glu Pro Ile Pro Val Ile Pro Thr
                    340                 345                 350

Cys His Tyr Met Met Gly Gly Val Pro Thr Lys Val Thr Gly Gln Ala
                    355                 360                 365

Leu Arg Val Asn Glu Gln Gly Glu Asp Glu Val Ile Pro Gly Leu Phe
        370                 375                 380

Ala Val Gly Glu Ile Ala Cys Val Ser Val His Gly Ala Asn Arg Leu
385                 390                 395                 400

Gly Gly Asn Ser Leu Leu Asp Leu Val Val Phe Gly Arg Ala Ala Gly
                    405                 410                 415

Val His Leu Leu Glu Cys Leu Glu Glu Gln Gly Glu Leu Arg Glu Ala
                    420                 425                 430

Ser Gln Glu Asn Ile Asp Ala Ala Met Ala Arg Phe Asn Arg Trp Glu
        435                 440                 445

Asn Asn Thr Thr Gly Glu Asp Pro Val Glu Ile Arg Lys Ala Leu Gln
        450                 455                 460

Arg Cys Met Gln Asn Asn Phe Ser Val Phe Arg Glu Gly Asp Ala Met
465                 470                 475                 480
```

```
Arg Glu Gly Leu Ala Glu Leu Lys Glu Ile Arg Glu Arg Leu Lys Ser
                485                 490                 495
Ala Arg Leu Asp Asp Arg Ser Pro Asp Phe Asn Thr Gln Arg Ile Glu
            500                 505                 510
Cys Leu Glu Leu Asp Asn Leu Met Glu Thr Ala Tyr Ala Thr Ala Val
        515                 520                 525
Ala Ala Asn Tyr Arg Thr Glu Ser Arg Gly Ala His Ser Arg Phe Asp
    530                 535                 540
Tyr Pro Glu Arg Asp Asp Ala Asn Trp Leu Cys His Ser Leu Tyr Val
545                 550                 555                 560
Pro Gln Thr Glu Ser Met Thr Arg Arg Glu Val Asn Met Gln Pro Lys
                565                 570                 575
Leu Arg Ala Ala Phe Pro Pro Lys Ala Arg Thr Tyr
            580                 585

<210> SEQ ID NO 4
<211> LENGTH: 238
<212> TYPE: PRT
<213> ORGANISM: Pantoea ananatis

<400> SEQUENCE: 4

Met Arg Leu Glu Phe Ser Ile Tyr Arg Tyr Asn Pro Asp Val Asp Asp
1               5                   10                  15
Lys Pro Arg Met Gln Asp Tyr Thr Leu Glu Ala Glu Asp Gly Arg Asp
            20                  25                  30
Met Met Leu Leu Asp Ala Leu Ile Arg Leu Lys Glu Lys Asp Pro Thr
        35                  40                  45
Leu Ala Phe Arg Arg Ser Cys Arg Glu Gly Val Cys Gly Ser Asp Gly
    50                  55                  60
Leu Asn Met Asn Gly Lys Asn Gly Leu Ala Cys Ile Thr Pro Val Ser
65                  70                  75                  80
Ala Leu Gly Asn Gly Lys Gln Lys Ile Val Ile Arg Pro Leu Pro Gly
                85                  90                  95
Leu Pro Val Val Arg Asp Leu Val Val Asp Met Gly Gln Phe Tyr Ala
            100                 105                 110
Gln Tyr Glu Lys Ile Lys Pro Phe Leu Leu Asn Asn Gly Glu Asn Pro
        115                 120                 125
Pro Ala Arg Glu His Leu Gln Ser Pro Gly Glu Arg Glu His Leu Asp
    130                 135                 140
Gly Leu Tyr Glu Cys Ile Leu Cys Ala Cys Cys Ser Thr Ser Cys Pro
145                 150                 155                 160
Ser Phe Trp Trp Asn Pro Asp Lys Phe Ile Gly Pro Ala Gly Leu Leu
                165                 170                 175
Ala Ala Tyr Arg Phe Leu Ile Asp Ser Arg Asp Thr Glu Thr Asp Ala
            180                 185                 190
Arg Leu Asp Asn Leu Ser Asp Ala Phe Ser Val Phe Arg Cys His Ser
        195                 200                 205
Ile Met Asn Cys Val Ser Val Cys Pro Lys Gly Leu Asn Pro Thr Arg
    210                 215                 220
Ala Ile Gly His Ile Lys Ser Met Leu Leu Gln Arg Ser Ala
225                 230                 235

<210> SEQ ID NO 5
<211> LENGTH: 3944
<212> TYPE: DNA
<213> ORGANISM: Pantoea ananatis
<220> FEATURE:
```

```
<221> NAME/KEY: CDS
<222> LOCATION: (527)..(913)

<400> SEQUENCE: 5
tataagcagt gaagggtaca gagtgagagg cgcgttccac aggaaatgta aagccgtgac      60
atgtgcatat cgcggttgtt aaagatccgg tcaggacata acttctttgt aaccaataac     120
ctgatggttt taaaagctgt tagtggcaat gttacataac ttgagcttag agaaagtgt      180 atccccataa cttttgtgca tcataggatt ttatcgggat agtttgtaac tgaattgttg     240
aactattgtc aaatcagata attaaatttg tatgaattgt gaaaaacgtg agaatgatca     300
ctgttccacc caaaattctc caaagagttt gtaggggaat tgtaatcaga atgtgatcgt     360
cctatacttc cggccaggtc tccggaatac cctgacacca ggagccaccc agcgtttgta     420
acacgtcatt taacactgga tgttgctatt ttggtgacgg ataaagtctg aacacgttta    480
gggttcaggt cttatgtccg gaggaagcaa aataaaaaag agctgt gtg ggc aaa       535
                                                  Val Gly Lys
                                                    1 acc gtg aaa aaa caa aga cct gtc aac ttg gat ctc tcg acg atc cgg       583
Thr Val Lys Lys Gln Arg Pro Val Asn Leu Asp Leu Ser Thr Ile Arg
  5              10                  15 ttt ccc gtt act gca ata tcg tcc att ctt cac cgc gtc tcc ggc gtc       631
Phe Pro Val Thr Ala Ile Ser Ser Ile Leu His Arg Val Ser Gly Val
20              25                  30                  35 atc acc ctg gtt gct ctc ggc atc ctg tta tgg ctt ctc ggt ctt tcc       679
Ile Thr Leu Val Ala Leu Gly Ile Leu Leu Trp Leu Leu Gly Leu Ser
            40                  45                  50 ctc tct tct cct gaa ggt ttc cag cac gct gca tct gtc atg aat ggc       727
Leu Ser Ser Pro Glu Gly Phe Gln His Ala Ala Ser Val Met Asn Gly
        55                  60                  65 ttc ttt gcg aag ttc atc atg tgg ggc att ttg act gcg ctg gcc tat       775
Phe Phe Ala Lys Phe Ile Met Trp Gly Ile Leu Thr Ala Leu Ala Tyr
    70                  75                  80 cat gca gtg ggc ggg ata cgt cat atg tta atg gat ttt ggt tat ctg       823
His Ala Val Gly Gly Ile Arg His Met Leu Met Asp Phe Gly Tyr Leu
85                  90                  95 gcc gaa acg ctc gaa gca ggt aag cgt tct gcg cag gtg acg ttt ggt       871
Ala Glu Thr Leu Glu Ala Gly Lys Arg Ser Ala Gln Val Thr Phe Gly
        100                 105                 110             115 att act gtc gtg ctt tca att tta gca gga gtc ctc gta tgg               913
Ile Thr Val Val Leu Ser Ile Leu Ala Gly Val Leu Val Trp
                120                 125 taagcaatgc atccgcgttg ggtcgcaatg gcattcagga ctggctgctg ctgcgcgcga     973
cggcaatcct catcacgctt tacatcatct atctcctcgg tttcgtggtg atgacagaca   1033
cgctgacgta tgacatctgg cgtggcttct tcgcttctgc atttacaaaa gtgttcacgc   1093
tcctgacgct gttttccatt ctgatccacg gctggatcgg tatgtggcag gtcttaacgg   1153
actacgttaa accgctggca acgcgtctgc tgttgcagtt ggtcatcgta gtggcgctgt   1213
tgtcatatgc aatttatgga tttgttgtgg tgtggggtgt gtaaatgagt ttaccagtaa   1273
gagaatttga tgccgtggtg atcggcgcag gcggcgcggg tatgcgcgcg cgttgcaaa    1333 tctcccagtc gggccagacc tgtgccctgt tgtccaaagt cttcccgacc cgttcccata   1393
cggtctccgc gcagggcgga atcaccgttg cgctgggtaa cacccatgac gataactggg   1453
aatggcatat gtatgacacc gtcaaaggtt ccgactacat cggtgaccag gacgcgatcg   1513
aatacatgtg tcacgtcggt ccggaagcga ttctggaact ggagcacatg ggcttgccct   1573
tctcccgtct tgatgacggc cgcgtttatc agcgtccgtt tggtggtcag tcgaaaaact   1633
```

```
tcggcggtga gcaggcggcg cgtactgccg cagcggccga ccgtaccggc cacgcactgc    1693
tgcatacgct gtatcagcag aacctgaaaa ataaaaccac tatcttctcc gaatggtatg    1753
cactggatct ggtcaaaaat gacgacggtg ccatcgtagg ctgtacggca atctgcatgg    1813
aaaccggcga aacggtttac ttcaaagcca aggccaccat tctggcgacg ggcggtgcag    1873
gacgtattta tcagtccacg acgaacgccc acatcaatac cggcgacggt gttggcatgg    1933
cgctgcgcgc gggcgtgcct gtgcaggata tggaaatgtg gcagttccac ccaaccggta    1993
tcgccggtgc tggtgtactg gtcaccgaag gctgtcgtgg tgaaggcggt tatctgctga    2053
acaaacacgg tgagcgtttc atggagcgct atgcgcctaa cgccaaagac cttgccggtc    2113
gtgacgttgt ggcccgttcg atgatggtgg agatccgtga aggtcgtggt tgcgacggtc    2173 catgggccc gcacatcaag ctgaaactcg atcacctggg tgcggaagtg ctggaatcgc    2233
gcctgccggg catccttgag ctgtcccgta cctttgctca cgttgacccg attaaagagc    2293
cgattccggt tatcccaacc tgtcactaca tgatgggcgg cgtgccaacc aaagtcaccg    2353
gtcaggcgct gcgtgtgaat gagcagggcg aagatgaagt gattcctggc ctgttcgcgg    2413
tgggtgaaat cgcctgcgta tcggtacacg gggcgaaccg tctgggtggc aactcgctgc    2473
tggacctggt ggtcttcggt cgcgcggctg gcgtgcatct gcttgaatgt ctggaagagc    2533
agggtgaact gcgtgaagcc agccaggaaa acattgatgc cgcgatggcg cgtttcaacc    2593
gctgggaaaa taacaccacg ggtgaagatc cggttgaaat ccgcaaggcg ttgcaacgct    2653
gcatgcagaa caacttctcg gtattccgtg aaggcgatgc gatgcgtgaa gggcttgctg    2713
aactgaaaga gatccgtgag cgtctgaagt ccgcgcgcct ggatgaccgc tcacctgact    2773
tcaatacaca gcgtattgag tgccttgagc tggataacct gatggaaacc gcttatgcca    2833
ccgcagtggc ggccaactac cgcactgaga gccgtggcgc acacagtcgc ttcgactatc    2893
cggaacgtga tgatgccaac tggctgtgcc atagcctcta tgttccgcaa acggaaagca    2953
tgacgcgccg tgaggtgaac atgcaaccga aactgcgtgc ggccttcccg ccgaaagcgc    3013
gtacctacta attgcggaga tcatcatgag acttgaattt tcgatctatc gttacaaccc    3073
ggacgtcgat gacaaaccgc gcatgcagga ctatacccctg gaagcggaag acggccgtga    3133
catgatgctg ctggatgcgc tgatccgtct gaaagagaag gatcctaccc tggcgttttcg    3193 tcgctcatgc cgtgaaggcg tgtgcggttc agacggcctg aacatgaacg ggaaaaacgg    3253
cctggcctgt atcacgccgg tctcggcgtt aggcaacggc aagcagaaaa tcgttatccg    3313
tcctctaccg ggcctgccgg tcgtgcgcga cctggtggtg gacatgggcc agttttatgc    3373
ccagtatgag aaaattaagc ctttcttatt gaataacggt gaaaacccgc cagcgcgtga    3433
gcatctgcag tcgccgggcg agcgtgagca tctggacgga ttgtatgagt gtattctctg    3493
cgcctgttgc tcaacctctt gcccgtcgtt ctggtggaac ccggacaagt ttattggtcc    3553
tgcaggcctg ctggccgctt accgcttcct gattgacagc cgtgatacgg aaacggatgc    3613
gcgtctggat aatctgagcg atgcattcag cgttttccgc tgtcacagca tcatgaactg    3673
tgtaagtgtt tgtcctaaag ggctaaaccc gacgcgcgcg atcggccaca ttaagtcgat    3733
gctgctgcaa cgcagcgcgt agttatacca ccgggaacct caggttcccg gtattttacg    3793
gaagcctctg taaacgcggt cccaaccacg tttacaaagg ttcccttacg ggccgggcgc    3853
gcgctgcgca cagtgctcgt atcgctgaac tcactacggc aaaccgcgaa agcggcaaca    3913
aatgaaacct caaaaaagca taacattgct t                                    3944
```

```
<210> SEQ ID NO 6
<211> LENGTH: 129
<212> TYPE: PRT
<213> ORGANISM: Pantoea ananatis

<400> SEQUENCE: 6

Val Gly Lys Thr Val Lys Lys Gln Arg Pro Val Asn Leu Asp Leu Ser
1               5                   10                  15

Thr Ile Arg Phe Pro Val Thr Ala Ile Ser Ser Ile Leu His Arg Val
            20                  25                  30

Ser Gly Val Ile Thr Leu Val Ala Leu Gly Ile Leu Leu Trp Leu Leu
        35                  40                  45

Gly Leu Ser Leu Ser Ser Pro Glu Gly Phe Gln His Ala Ala Ser Val
    50                  55                  60

Met Asn Gly Phe Phe Ala Lys Phe Ile Met Trp Gly Ile Leu Thr Ala
65                  70                  75                  80

Leu Ala Tyr His Ala Val Gly Gly Ile Arg His Met Leu Met Asp Phe
                85                  90                  95

Gly Tyr Leu Ala Glu Thr Leu Glu Ala Gly Lys Arg Ser Ala Gln Val
            100                 105                 110

Thr Phe Gly Ile Thr Val Val Leu Ser Ile Leu Ala Gly Val Leu Val
        115                 120                 125

Trp

<210> SEQ ID NO 7
<211> LENGTH: 4556
<212> TYPE: DNA
<213> ORGANISM: Pantoea ananatis
<220> FEATURE:
<221> NAME/KEY: CDS
<222> LOCATION: (2)..(121)
<220> FEATURE:
<221> NAME/KEY: CDS
<222> LOCATION: (322)..(3129)
<220> FEATURE:
<221> NAME/KEY: CDS
<222> LOCATION: (3145)..(4368)
<220> FEATURE:
<221> NAME/KEY: CDS
<222> LOCATION: (4437)..(4556)

<400> SEQUENCE: 7 t gca ttc agc gtt ttc cgc tgt cac agc atc atg aac tgt gta agt gtt    49
  Ala Phe Ser Val Phe Arg Cys His Ser Ile Met Asn Cys Val Ser Val
  1               5                   10                  15 tgt cct aaa ggg cta aac ccg acg cgc gct atc ggc cac att aag tcg      97
Cys Pro Lys Gly Leu Asn Pro Thr Arg Ala Ile Gly His Ile Lys Ser
            20                  25                  30 atg ctg ctg caa cgc agc gcg tag ttataccacc gggaacctca ggttcccggt    151
Met Leu Leu Gln Arg Ser Ala
        35 attttacgga agcctctgta aacgcggtcc caaccacgtt tacaaaggtt cccttacggg    211 ccgggcgcgc gctgcgcaca gtgctcgtat cgctgaactc actacggcaa accgcgaaag    271 cggcaacaaa tgaaacctca aaaaagcata acattgctta agggatcaca atg cag       327
                                                      Met Gln
                                                          40 aac agc gcg atg aag ccc tgg ctg gac tcc tcc tgg ctg gcc ggc gcg      375
Asn Ser Ala Met Lys Pro Trp Leu Asp Ser Ser Trp Leu Ala Gly Ala
                    45                  50                  55 aat cag tct tac ata gag caa ctc tat gag gat ttc ctg acc gat cct      423
Asn Gln Ser Tyr Ile Glu Gln Leu Tyr Glu Asp Phe Leu Thr Asp Pro
60                  65                  70
```

| | | |
|---|---|---|
| gac tct gtg gat gca gtg tgg cgc tcg atg ttc caa cag tta cca ggc | | 471 |
| Asp Ser Val Asp Ala Val Trp Arg Ser Met Phe Gln Gln Leu Pro Gly | | |
| 75 80 85 | | |
| acg gga gtg aaa cct gag cag ttc cac tcc gca act cgc gaa tat ttc | | 519 |
| Thr Gly Val Lys Pro Glu Gln Phe His Ser Ala Thr Arg Glu Tyr Phe | | |
| 90 95 100 105 | | |
| cgt cgc ctg gcg aaa gac gca tct cgt tac acc tcc tca gtt acc gat | | 567 |
| Arg Arg Leu Ala Lys Asp Ala Ser Arg Tyr Thr Ser Ser Val Thr Asp | | |
| 110 115 120 | | |
| ccg gca acc aac tcc aaa caa gtg aaa gtg ctg cag ctg att aac gcg | | 615 |
| Pro Ala Thr Asn Ser Lys Gln Val Lys Val Leu Gln Leu Ile Asn Ala | | |
| 125 130 135 | | |
| ttt cgt ttc cgc gga cat cag gaa gca aat ctc gat ccg ctt ggc ctg | | 663 |
| Phe Arg Phe Arg Gly His Gln Glu Ala Asn Leu Asp Pro Leu Gly Leu | | |
| 140 145 150 | | |
| tgg aaa cag gac cgc gtt gcc gat ctc gat cct gcc ttt cac gat ctg | | 711 |
| Trp Lys Gln Asp Arg Val Ala Asp Leu Asp Pro Ala Phe His Asp Leu | | |
| 155 160 165 | | |
| acc gac gcc gat ttt cag gaa agc ttt aac gta ggt tct ttt gcc att | | 759 |
| Thr Asp Ala Asp Phe Gln Glu Ser Phe Asn Val Gly Ser Phe Ala Ile | | |
| 170 175 180 185 | | |
| ggc aaa gaa acc atg aag ctg gcc gat ctg ttc gac gcg ctg aag cag | | 807 |
| Gly Lys Glu Thr Met Lys Leu Ala Asp Leu Phe Asp Ala Leu Lys Gln | | |
| 190 195 200 | | |
| acc tac tgt ggc tcg att ggt gca gag tat atg cac atc aat aac acc | | 855 |
| Thr Tyr Cys Gly Ser Ile Gly Ala Glu Tyr Met His Ile Asn Asn Thr | | |
| 205 210 215 | | |
| gaa gag aaa cgc tgg atc cag cag cgt atc gaa tcc ggt gcg agc cag | | 903 |
| Glu Glu Lys Arg Trp Ile Gln Gln Arg Ile Glu Ser Gly Ala Ser Gln | | |
| 220 225 230 | | |
| acg tca ttc agt ggc gaa gag aaa aaa ggt ttc ctg aaa gag ctg acc | | 951 |
| Thr Ser Phe Ser Gly Glu Glu Lys Lys Gly Phe Leu Lys Glu Leu Thr | | |
| 235 240 245 | | |
| gcg gca gaa ggg ctg gaa aaa tat ctg ggc gcg aaa ttc ccg ggt gca | | 999 |
| Ala Ala Glu Gly Leu Glu Lys Tyr Leu Gly Ala Lys Phe Pro Gly Ala | | |
| 250 255 260 265 | | |
| aaa cgt ttc tcg ctg gaa ggc ggt gat gcg ctg gtg ccg atg ctg cgc | | 1047 |
| Lys Arg Phe Ser Leu Glu Gly Gly Asp Ala Leu Val Pro Met Leu Arg | | |
| 270 275 280 | | |
| gag atg att cgt cat gcg ggc aaa agc ggc aca cgt gaa gtg gta ctg | | 1095 |
| Glu Met Ile Arg His Ala Gly Lys Ser Gly Thr Arg Glu Val Val Leu | | |
| 285 290 295 | | |
| ggg atg gcg cac cgt ggc cgt ctt aac gta ctg att aac gta ctg ggt | | 1143 |
| Gly Met Ala His Arg Gly Arg Leu Asn Val Leu Ile Asn Val Leu Gly | | |
| 300 305 310 | | |
| aaa aag cca cag gat ctg ttc gac gaa ttc tcc ggt aaa cac aaa gag | | 1191 |
| Lys Lys Pro Gln Asp Leu Phe Asp Glu Phe Ser Gly Lys His Lys Glu | | |
| 315 320 325 | | |
| cat ctg ggc acc ggt gat gtg aag tat cac atg ggc ttc tct tcg gat | | 1239 |
| His Leu Gly Thr Gly Asp Val Lys Tyr His Met Gly Phe Ser Ser Asp | | |
| 330 335 340 345 | | |
| att gaa acc gaa ggt ggt ctg gtg cat ctg gcg ctg gcg ttt aac ccg | | 1287 |
| Ile Glu Thr Glu Gly Gly Leu Val His Leu Ala Leu Ala Phe Asn Pro | | |
| 350 355 360 | | |
| tct cac ctg gaa att gtc agc ccg gtg gtc atg gga tcg gta cgt gca | | 1335 |
| Ser His Leu Glu Ile Val Ser Pro Val Val Met Gly Ser Val Arg Ala | | |
| 365 370 375 | | |
| cgt ctc gat cgt ctg gcc gaa ccg gtc agc aat aaa gtg ttg cct atc | | 1383 |
| Arg Leu Asp Arg Leu Ala Glu Pro Val Ser Asn Lys Val Leu Pro Ile | | |
| 380 385 390 | | |

```
acc att cac ggt gat gcg gcg gtg att ggt cag ggc gtg gtt cag gaa      1431
Thr Ile His Gly Asp Ala Ala Val Ile Gly Gln Gly Val Val Gln Glu
    395                 400                 405 acc ctg aac atg tct cag gcg cgc ggc tac gaa gtg ggc ggc acg gta      1479
Thr Leu Asn Met Ser Gln Ala Arg Gly Tyr Glu Val Gly Gly Thr Val
410                 415                 420                 425 cgt atc gtc att aac aac cag gtt ggt ttt acc acc tcc aac ccg aaa      1527
Arg Ile Val Ile Asn Asn Gln Val Gly Phe Thr Thr Ser Asn Pro Lys
                430                 435                 440 gat gcg cgt tca acc ccg tac tgt act gac atc ggc aag atg gtg ctg      1575
Asp Ala Arg Ser Thr Pro Tyr Cys Thr Asp Ile Gly Lys Met Val Leu
445                 450                 455 gca ccg att ttc cac gtc aat gct gac gat ccg gaa gcg gtg gcc ttt      1623
Ala Pro Ile Phe His Val Asn Ala Asp Asp Pro Glu Ala Val Ala Phe
        460                 465                 470 gtt acc cgc ctg gcg ctg gac tat cgc aac acc ttc aaa cgc gat gtg      1671
Val Thr Arg Leu Ala Leu Asp Tyr Arg Asn Thr Phe Lys Arg Asp Val
475                 480                 485 ttt atc gat ctg gtg tgc tat cgc cgt cat ggt cac aac gag gcg gat      1719
Phe Ile Asp Leu Val Cys Tyr Arg Arg His Gly His Asn Glu Ala Asp
490                 495                 500                 505 gag cca agt gct acc cag ccg ttg atg tac cag aaa atc aaa aag cat      1767
Glu Pro Ser Ala Thr Gln Pro Leu Met Tyr Gln Lys Ile Lys Lys His
            510                 515                 520 ccg acg ccg cgt aaa att tac gcc gat cgt ctg gaa ggc gaa ggt gtc      1815
Pro Thr Pro Arg Lys Ile Tyr Ala Asp Arg Leu Glu Gly Glu Gly Val
                525                 530                 535 gcg tcg cag gaa gat gcc acc gag atg gtg aac ctg tac cgc gat gcg      1863
Ala Ser Gln Glu Asp Ala Thr Glu Met Val Asn Leu Tyr Arg Asp Ala
540                 545                 550 ctc gat gcg ggc gaa tgc gtg gtg ccg gaa tgg cgt ccg atg agc ctg      1911
Leu Asp Ala Gly Glu Cys Val Val Pro Glu Trp Arg Pro Met Ser Leu
        555                 560                 565 cac tcc ttc acg tgg tcg cct tat ctg aac cac gaa tgg gat gag cct      1959
His Ser Phe Thr Trp Ser Pro Tyr Leu Asn His Glu Trp Asp Glu Pro
570                 575                 580                 585 tat ccg gca cag gtt gac atg aaa cgc ctg aag gaa ctg gca ttg cgt      2007
Tyr Pro Ala Gln Val Asp Met Lys Arg Leu Lys Glu Leu Ala Leu Arg
                590                 595                 600 atc agc cag gtc cct gag cag att gaa gtg cag tcg cgc gtg gcc aag      2055
Ile Ser Gln Val Pro Glu Gln Ile Glu Val Gln Ser Arg Val Ala Lys
            605                 610                 615 atc tat aac gat cgc aag ctg atg gcc gaa ggc gag aaa gcg ttc gac      2103
Ile Tyr Asn Asp Arg Lys Leu Met Ala Glu Gly Glu Lys Ala Phe Asp
                620                 625                 630 tgg ggc ggt gcc gag aat ctg gcg tac gcc acg ctg gtg gat gaa ggt      2151
Trp Gly Gly Ala Glu Asn Leu Ala Tyr Ala Thr Leu Val Asp Glu Gly
635                 640                 645 att ccg gtt cgc ctc tcg ggt gaa gac tcc ggt cgt gga acc ttc ttc      2199
Ile Pro Val Arg Leu Ser Gly Glu Asp Ser Gly Arg Gly Thr Phe Phe
650                 655                 660                 665 cat cgc cac gcg gtc gtg cac aac cag gct aac ggt tca acc tat acg      2247
His Arg His Ala Val Val His Asn Gln Ala Asn Gly Ser Thr Tyr Thr
                670                 675                 680 ccg ctg cac cat att cat aac agc cag ggc gag ttc aaa gtc tgg gat      2295
Pro Leu His His Ile His Asn Ser Gln Gly Glu Phe Lys Val Trp Asp
            685                 690                 695 tcg gtg ctg tct gaa gaa gcg gtg ctg gcg ttt gaa tac ggt tac gcc      2343
Ser Val Leu Ser Glu Glu Ala Val Leu Ala Phe Glu Tyr Gly Tyr Ala
700                 705                 710
```

| | |
|---|---|
| acg gct gag ccg cgc gtg ctg acc atc tgg gaa gcg cag ttt ggt gac<br>Thr Ala Glu Pro Arg Val Leu Thr Ile Trp Glu Ala Gln Phe Gly Asp<br>715                    720                  725 | 2391 |
| ttt gcc aac ggt gct cag gtg gtg att gac cag ttc atc agc tct ggc<br>Phe Ala Asn Gly Ala Gln Val Val Ile Asp Gln Phe Ile Ser Ser Gly<br>730                    735                  740                  745 | 2439 |
| gaa cag aag tgg ggc cgt atg tgt ggc ctg gtg atg ttg ctg ccg cat<br>Glu Gln Lys Trp Gly Arg Met Cys Gly Leu Val Met Leu Leu Pro His<br>                  750                  755                  760 | 2487 |
| ggc tac gaa ggt cag gga ccg gaa cac tcc tct gcc cgt ctg gaa cgc<br>Gly Tyr Glu Gly Gln Gly Pro Glu His Ser Ser Ala Arg Leu Glu Arg<br>765                    770                  775 | 2535 |
| tat ctg caa ctt tgc gcc gag cag aac atg cag gtt tgc gtc ccg tcg<br>Tyr Leu Gln Leu Cys Ala Glu Gln Asn Met Gln Val Cys Val Pro Ser<br>780                    785                  790 | 2583 |
| acg ccg gct cag gtg tat cac atg ctg cgc cgt cag gcg ctg cgc ggg<br>Thr Pro Ala Gln Val Tyr His Met Leu Arg Arg Gln Ala Leu Arg Gly<br>795                    800                  805 | 2631 |
| atg cgc cgt ccg ctg gtg gtg atg tcg ccg aag tcg ctg tta cgc cat<br>Met Arg Arg Pro Leu Val Val Met Ser Pro Lys Ser Leu Leu Arg His<br>810                    815                  820                  825 | 2679 |
| cca ctg gcg atc tcg tcg ctg gat gaa ctg gca aac ggc agt ttc cag<br>Pro Leu Ala Ile Ser Ser Leu Asp Glu Leu Ala Asn Gly Ser Phe Gln<br>                  830                  835                  840 | 2727 |
| ccg gcc att ggt gag atc gac gat ctg gat ccg cag ggc gtg aaa cgc<br>Pro Ala Ile Gly Glu Ile Asp Asp Leu Asp Pro Gln Gly Val Lys Arg<br>                  845                  850                  855 | 2775 |
| gtc gtg ctg tgc tcc ggt aag gtt tac tac gat ctg ctg gaa cag cgt<br>Val Val Leu Cys Ser Gly Lys Val Tyr Tyr Asp Leu Leu Glu Gln Arg<br>860                    865                  870 | 2823 |
| cgt aaa gac gag aaa acc gat gtt gcc atc gtg cgc atc gaa cag ctt<br>Arg Lys Asp Glu Lys Thr Asp Val Ala Ile Val Arg Ile Glu Gln Leu<br>875                    880                  885 | 2871 |
| tac ccg ttc ccg cat cag gcg gta cag gaa gca ttg aaa gcc tat tct<br>Tyr Pro Phe Pro His Gln Ala Val Gln Glu Ala Leu Lys Ala Tyr Ser<br>890                    895                  900                  905 | 2919 |
| cac gta cag gac ttt gtc tgg tgc cag gaa gag cct ctg aac cag ggc<br>His Val Gln Asp Phe Val Trp Cys Gln Glu Glu Pro Leu Asn Gln Gly<br>                  910                  915                  920 | 2967 |
| gcc tgg tac tgt agc cag cat cat ttc cgt gat gtc gtg ccg ttt ggt<br>Ala Trp Tyr Cys Ser Gln His His Phe Arg Asp Val Val Pro Phe Gly<br>                  925                  930                  935 | 3015 |
| gcc acc ctg cgt tat gca ggt cgc ccg gca tcg gct tct ccg gcc gtg<br>Ala Thr Leu Arg Tyr Ala Gly Arg Pro Ala Ser Ala Ser Pro Ala Val<br>                  940                  945                  950 | 3063 |
| ggt tat atg tcc gta cac caa caa cag cag caa gac ctg gtt aat gac<br>Gly Tyr Met Ser Val His Gln Gln Gln Gln Gln Asp Leu Val Asn Asp<br>955                    960                  965 | 3111 |
| gca ctg aac gtc aat taa ttaaaaggaa agata atg agt agc gta gat att<br>Ala Leu Asn Val Asn                                Met Ser Ser Val Asp Ile<br>970                                                        975                  980 | 3162 |
| ctc gtt ccc gac ctg cct gaa tcg gtt gca gat gcc aca gta gca acc<br>Leu Val Pro Asp Leu Pro Glu Ser Val Ala Asp Ala Thr Val Ala Thr<br>                  985                  990                  995 | 3210 |
| tgg cac aag aaa cca ggc gat gca gtc agc cgc gat gaa gtc atc<br>Trp His Lys Lys Pro Gly Asp Ala Val Ser Arg Asp Glu Val Ile<br>                1000                 1005                1010 | 3255 |
| gtc gaa att gaa act gac aaa gtc gtg ctg gaa gtg ccg gca tct<br>Val Glu Ile Glu Thr Asp Lys Val Val Leu Glu Val Pro Ala Ser<br>                1015                 1020                1025 | 3300 |

| | | | | | | | | | | | | |
|---|---|---|---|---|---|---|---|---|---|---|---|---|
| gcc | gat | ggc | gtg | ctg | gaa | gcc | gtg | ctg | gaa | gac | gaa | ggg | gca | acc | 3345 |
| Ala | Asp | Gly | Val | Leu | Glu | Ala | Val | Leu | Glu | Asp | Glu | Gly | Ala | Thr | |
| | | 1030 | | | | 1035 | | | | 1040 | | | | | |

| gtt | acg | tcc | cgc | cag | atc | ctg | ggt | cgc | ctg | aaa | gaa | ggc | aac | agt | 3390 |
| Val | Thr | Ser | Arg | Gln | Ile | Leu | Gly | Arg | Leu | Lys | Glu | Gly | Asn | Ser |
| | | 1045 | | | | 1050 | | | | 1055 | | | | |

| gcg | ggt | aaa | gaa | agc | agt | gcc | aaa | gcg | gaa | agc | aat | gac | acc | acg | 3435 |
| Ala | Gly | Lys | Glu | Ser | Ser | Ala | Lys | Ala | Glu | Ser | Asn | Asp | Thr | Thr |
| | 1060 | | | | 1065 | | | | | 1070 | | | | |

| cca | gcc | cag | cgt | cag | aca | gcg | tcg | ctt | gaa | gaa | gag | agc | agc | gat | 3480 |
| Pro | Ala | Gln | Arg | Gln | Thr | Ala | Ser | Leu | Glu | Glu | Glu | Ser | Ser | Asp |
| | | 1075 | | | | 1080 | | | | 1085 | | | | |

| gcg | ctc | agc | ccg | gcg | atc | cgt | cgc | ctg | att | gcg | gag | cat | aat | ctt | 3525 |
| Ala | Leu | Ser | Pro | Ala | Ile | Arg | Arg | Leu | Ile | Ala | Glu | His | Asn | Leu |
| | | 1090 | | | | 1095 | | | | 1100 | | | | |

| gac | gct | gcg | cag | atc | aaa | ggc | acc | ggc | gta | ggc | gga | cgt | tta | acg | 3570 |
| Asp | Ala | Ala | Gln | Ile | Lys | Gly | Thr | Gly | Val | Gly | Gly | Arg | Leu | Thr |
| | | 1105 | | | | 1110 | | | | 1115 | | | | |

| cgt | gaa | gac | gtt | gaa | aaa | cat | ctg | gcg | aac | aaa | ccg | cag | gct | gag | 3615 |
| Arg | Glu | Asp | Val | Glu | Lys | His | Leu | Ala | Asn | Lys | Pro | Gln | Ala | Glu |
| | | 1120 | | | | 1125 | | | | 1130 | | | | |

| aaa | gcc | gcc | gcg | cca | gcg | gcg | ggt | gca | gca | acg | gct | cag | cag | cct | 3660 |
| Lys | Ala | Ala | Ala | Pro | Ala | Ala | Gly | Ala | Ala | Thr | Ala | Gln | Gln | Pro |
| | 1135 | | | | 1140 | | | | | 1145 | | | | |

| gtt | gcc | aac | cgc | agc | gaa | aaa | cgt | gtt | ccg | atg | acg | cgt | tta | cgt | 3705 |
| Val | Ala | Asn | Arg | Ser | Glu | Lys | Arg | Val | Pro | Met | Thr | Arg | Leu | Arg |
| | | 1150 | | | | 1155 | | | | 1160 | | | | |

| aag | cgc | gtc | gcg | gag | cgt | ctg | ctg | gaa | gcc | aag | aac | agc | acc | gcc | 3750 |
| Lys | Arg | Val | Ala | Glu | Arg | Leu | Leu | Glu | Ala | Lys | Asn | Ser | Thr | Ala |
| | | 1165 | | | | 1170 | | | | 1175 | | | | |

| atg | ttg | acg | acc | ttc | aac | gaa | atc | aac | atg | aag | ccg | att | atg | gat | 3795 |
| Met | Leu | Thr | Thr | Phe | Asn | Glu | Ile | Asn | Met | Lys | Pro | Ile | Met | Asp |
| | | 1180 | | | | 1185 | | | | 1190 | | | | |

| ctg | cgt | aag | cag | tac | ggc | gat | gcg | ttc | gag | aag | cgt | cac | ggt | gtg | 3840 |
| Leu | Arg | Lys | Gln | Tyr | Gly | Asp | Ala | Phe | Glu | Lys | Arg | His | Gly | Val |
| | | 1195 | | | | 1200 | | | | 1205 | | | | |

| cgt | ctg | ggc | ttt | atg | tct | ttc | tac | atc | aag | gcc | gtg | gtc | gaa | gcg | 3885 |
| Arg | Leu | Gly | Phe | Met | Ser | Phe | Tyr | Ile | Lys | Ala | Val | Val | Glu | Ala |
| | | 1210 | | | | 1215 | | | | 1220 | | | | |

| ctg | aag | cgt | tat | cca | gaa | gtc | aac | gcc | tct | atc | gat | ggc | gaa | gac | 3930 |
| Leu | Lys | Arg | Tyr | Pro | Glu | Val | Asn | Ala | Ser | Ile | Asp | Gly | Glu | Asp |
| | | 1225 | | | | 1230 | | | | 1235 | | | | |

| gtg | gtg | tac | cac | aac | tat | ttc | gat | gtg | agt | att | gcc | gtc | tct | acg | 3975 |
| Val | Val | Tyr | His | Asn | Tyr | Phe | Asp | Val | Ser | Ile | Ala | Val | Ser | Thr |
| | | 1240 | | | | 1245 | | | | 1250 | | | | |

| cca | cgc | gga | ctg | gtg | acg | cct | gtc | ctg | cgt | gac | gtt | gat | gcg | ctg | 4020 |
| Pro | Arg | Gly | Leu | Val | Thr | Pro | Val | Leu | Arg | Asp | Val | Asp | Ala | Leu |
| | | 1255 | | | | 1260 | | | | 1265 | | | | |

| agc | atg | gct | gac | atc | gag | aag | aaa | att | aaa | gaa | ctg | gca | gtg | aaa | 4065 |
| Ser | Met | Ala | Asp | Ile | Glu | Lys | Lys | Ile | Lys | Glu | Leu | Ala | Val | Lys |
| | | 1270 | | | | 1275 | | | | 1280 | | | | |

| ggc | cgt | gac | ggc | aag | ctg | acg | gtt | gac | gat | ctg | acg | ggc | ggt | aac | 4110 |
| Gly | Arg | Asp | Gly | Lys | Leu | Thr | Val | Asp | Asp | Leu | Thr | Gly | Gly | Asn |
| | | 1285 | | | | 1290 | | | | 1295 | | | | |

| ttt | acc | atc | acc | aac | ggt | ggt | gtg | ttc | ggt | tcg | ctg | atg | tct | acg | 4155 |
| Phe | Thr | Ile | Thr | Asn | Gly | Gly | Val | Phe | Gly | Ser | Leu | Met | Ser | Thr |
| | | 1300 | | | | 1305 | | | | 1310 | | | | |

| cca | atc | atc | aac | ccg | cca | cag | agc | gcg | att | ctg | ggc | atg | cac | gcc | 4200 |
| Pro | Ile | Ile | Asn | Pro | Pro | Gln | Ser | Ala | Ile | Leu | Gly | Met | His | Ala |
| | | 1315 | | | | 1320 | | | | 1325 | | | | |

```
att aaa gat cgt cct atg gcg gtc aat ggt cag gtt gtg atc ctg      4245
Ile Lys Asp Arg Pro Met Ala Val Asn Gly Gln Val Val Ile Leu
        1330                1335                1340 cca atg atg tac ctg gct ctc tcc tac gat cac cgt tta atc gat      4290
Pro Met Met Tyr Leu Ala Leu Ser Tyr Asp His Arg Leu Ile Asp
        1345                1350                1355 ggt cgt gaa tct gtc ggc tat ctg gtc gcg gtc aaa gag atg ctg      4335
Gly Arg Glu Ser Val Gly Tyr Leu Val Ala Val Lys Glu Met Leu
        1360                1365                1370 gaa gat ccg gcg cgt ctg ctg ctg gat gtc tga ttcatcactg           4378
Glu Asp Pro Ala Arg Leu Leu Leu Asp Val
        1375                1380 ggcacgcgtt gcgtgcccaa tctcaatact cttttcagat ctgaatggat agaacatc  4436 atg aac tta cac gaa tac cag gct aaa cag ctg ttt gca cgg tat      4481
Met Asn Leu His Glu Tyr Gln Ala Lys Gln Leu Phe Ala Arg Tyr
        1385                1390                1395 ggc atg cca gca ccg acc ggc tac gcc tgt act aca cca cgt gaa      4526
Gly Met Pro Ala Pro Thr Gly Tyr Ala Cys Thr Thr Pro Arg Glu
        1400                1405                1410 gca gaa gaa gcg gca tcg aaa atc ggt gca                          4556
Ala Glu Glu Ala Ala Ser Lys Ile Gly Ala
        1415                1420
```

<210> SEQ ID NO 8
<211> LENGTH: 39
<212> TYPE: PRT
<213> ORGANISM: Pantoea ananatis

<400> SEQUENCE: 8

Ala Phe Ser Val Phe Arg Cys His Ser Ile Met Asn Cys Val Ser Val
1               5                   10                  15

Cys Pro Lys Gly Leu Asn Pro Thr Arg Ala Ile Gly His Ile Lys Ser
            20                  25                  30

Met Leu Leu Gln Arg Ser Ala
        35

<210> SEQ ID NO 9
<211> LENGTH: 935
<212> TYPE: PRT
<213> ORGANISM: Pantoea ananatis

<400> SEQUENCE: 9

Met Gln Asn Ser Ala Met Lys Pro Trp Leu Asp Ser Ser Trp Leu Ala
1               5                   10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Glu Gln Phe His Ser Ala Thr Arg Glu
    50                  55                  60

Tyr Phe Arg Arg Leu Ala Lys Asp Ala Ser Arg Tyr Thr Ser Ser Val
65                  70                  75                  80

Thr Asp Pro Ala Thr Asn Ser Lys Gln Val Lys Val Leu Gln Leu Ile
                85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

```
Asp Leu Thr Asp Ala Asp Phe Gln Glu Ser Phe Asn Val Gly Ser Phe
130                 135                 140

Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
            165                 170                 175

Asn Thr Glu Glu Lys Arg Trp Ile Gln Gln Arg Ile Glu Ser Gly Ala
        180                 185                 190

Ser Gln Thr Ser Phe Ser Gly Glu Lys Lys Gly Phe Leu Lys Glu
    195                 200                 205

Leu Thr Ala Ala Glu Gly Leu Glu Lys Tyr Leu Gly Ala Lys Phe Pro
210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
            245                 250                 255

Val Leu Gly Met Ala His Arg Gly Arg Leu Asn Val Leu Ile Asn Val
            260                 265                 270

Leu Gly Lys Lys Pro Gln Asp Leu Phe Asp Glu Phe Ser Gly Lys His
        275                 280                 285

Lys Glu His Leu Gly Thr Gly Asp Val Lys Tyr His Met Gly Phe Ser
290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Val Met Gly Ser Val
            325                 330                 335

Arg Ala Arg Leu Asp Arg Leu Ala Glu Pro Val Ser Asn Lys Val Leu
            340                 345                 350

Pro Ile Thr Ile His Gly Asp Ala Ala Val Ile Gly Gln Gly Val Val
        355                 360                 365

Gln Glu Thr Leu Asn Met Ser Gln Ala Arg Gly Tyr Glu Val Gly Gly
    370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
            405                 410                 415

Val Leu Ala Pro Ile Phe His Val Asn Ala Asp Asp Pro Glu Ala Val
            420                 425                 430

Ala Phe Val Thr Arg Leu Ala Leu Asp Tyr Arg Asn Thr Phe Lys Arg
            435                 440                 445

Asp Val Phe Ile Asp Leu Val Cys Tyr Arg Arg His Gly His Asn Glu
        450                 455                 460

Ala Asp Glu Pro Ser Ala Thr Gln Pro Leu Met Tyr Gln Lys Ile Lys
465                 470                 475                 480

Lys His Pro Thr Pro Arg Lys Ile Tyr Ala Asp Arg Leu Glu Gly Glu
            485                 490                 495

Gly Val Ala Ser Gln Glu Asp Ala Thr Glu Met Val Asn Leu Tyr Arg
            500                 505                 510

Asp Ala Leu Asp Ala Gly Glu Cys Val Val Pro Glu Trp Arg Pro Met
        515                 520                 525

Ser Leu His Ser Phe Thr Trp Ser Pro Tyr Leu Asn His Glu Trp Asp
    530                 535                 540

Glu Pro Tyr Pro Ala Gln Val Asp Met Lys Arg Leu Lys Glu Leu Ala
545                 550                 555                 560
```

Leu Arg Ile Ser Gln Val Pro Glu Gln Ile Glu Val Gln Ser Arg Val
             565                 570                 575

Ala Lys Ile Tyr Asn Asp Arg Lys Leu Met Ala Glu Gly Glu Lys Ala
         580                 585                 590

Phe Asp Trp Gly Gly Ala Glu Asn Leu Ala Tyr Ala Thr Leu Val Asp
         595                 600                 605

Glu Gly Ile Pro Val Arg Leu Ser Gly Glu Asp Ser Gly Arg Gly Thr
         610                 615                 620

Phe Phe His Arg His Ala Val Val His Asn Gln Ala Asn Gly Ser Thr
625                 630                 635                 640

Tyr Thr Pro Leu His His Ile His Asn Ser Gln Gly Glu Phe Lys Val
             645                 650                 655

Trp Asp Ser Val Leu Ser Glu Glu Ala Val Leu Ala Phe Glu Tyr Gly
             660                 665                 670

Tyr Ala Thr Ala Glu Pro Arg Val Leu Thr Ile Trp Glu Ala Gln Phe
         675                 680                 685

Gly Asp Phe Ala Asn Gly Ala Gln Val Val Ile Asp Gln Phe Ile Ser
         690                 695                 700

Ser Gly Glu Gln Lys Trp Gly Arg Met Cys Gly Leu Val Met Leu Leu
705                 710                 715                 720

Pro His Gly Tyr Glu Gly Gln Gly Pro Glu His Ser Ser Ala Arg Leu
             725                 730                 735

Glu Arg Tyr Leu Gln Leu Cys Ala Glu Gln Asn Met Gln Val Cys Val
         740                 745                 750

Pro Ser Thr Pro Ala Gln Val Tyr His Met Leu Arg Arg Gln Ala Leu
         755                 760                 765

Arg Gly Met Arg Arg Pro Leu Val Val Met Ser Pro Lys Ser Leu Leu
         770                 775                 780

Arg His Pro Leu Ala Ile Ser Ser Leu Asp Glu Leu Ala Asn Gly Ser
785                 790                 795                 800

Phe Gln Pro Ala Ile Gly Glu Ile Asp Asp Leu Asp Pro Gln Gly Val
         805                 810                 815

Lys Arg Val Val Leu Cys Ser Gly Lys Val Tyr Tyr Asp Leu Leu Glu
         820                 825                 830

Gln Arg Arg Lys Asp Glu Lys Thr Asp Val Ala Ile Val Arg Ile Glu
         835                 840                 845

Gln Leu Tyr Pro Phe Pro His Gln Ala Val Gln Glu Ala Leu Lys Ala
         850                 855                 860

Tyr Ser His Val Gln Asp Phe Val Trp Cys Gln Glu Glu Pro Leu Asn
865                 870                 875                 880

Gln Gly Ala Trp Tyr Cys Ser Gln His His Phe Arg Asp Val Val Pro
             885                 890                 895

Phe Gly Ala Thr Leu Arg Tyr Ala Gly Arg Pro Ala Ser Ala Ser Pro
         900                 905                 910

Ala Val Gly Tyr Met Ser Val His Gln Gln Gln Gln Gln Asp Leu Val
         915                 920                 925

Asn Asp Ala Leu Asn Val Asn
        930                 935

<210> SEQ ID NO 10
<211> LENGTH: 407
<212> TYPE: PRT
<213> ORGANISM: Pantoea ananatis

<400> SEQUENCE: 10

```
Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Ser
            20                  25                  30

Arg Asp Glu Val Ile Val Glu Ile Glu Thr Asp Lys Val Val Leu Glu
            35                  40                  45

Val Pro Ala Ser Ala Asp Gly Val Leu Glu Ala Val Leu Glu Asp Glu
        50                  55                  60

Gly Ala Thr Val Thr Ser Arg Gln Ile Leu Gly Arg Leu Lys Glu Gly
65                  70                  75                  80

Asn Ser Ala Gly Lys Glu Ser Ser Ala Lys Ala Glu Ser Asn Asp Thr
                85                  90                  95

Thr Pro Ala Gln Arg Gln Thr Ala Ser Leu Glu Glu Ser Ser Asp
            100                 105                 110

Ala Leu Ser Pro Ala Ile Arg Arg Leu Ile Ala Glu His Asn Leu Asp
        115                 120                 125

Ala Ala Gln Ile Lys Gly Thr Gly Gly Arg Leu Thr Arg Glu
130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
            245                 250                 255

Ser Ile Asp Gly Glu Asp Val Val Tyr His Asn Tyr Phe Asp Val Ser
        260                 265                 270

Ile Ala Val Ser Thr Pro Arg Gly Leu Val Thr Pro Val Leu Arg Asp
    275                 280                 285

Val Asp Ala Leu Ser Met Ala Asp Ile Glu Lys Lys Ile Lys Glu Leu
    290                 295                 300

Ala Val Lys Gly Arg Asp Gly Lys Leu Thr Val Asp Asp Leu Thr Gly
305                 310                 315                 320

Gly Asn Phe Thr Ile Thr Asn Gly Gly Val Phe Gly Ser Leu Met Ser
                325                 330                 335

Thr Pro Ile Ile Asn Pro Pro Gln Ser Ala Ile Leu Gly Met His Ala
            340                 345                 350

Ile Lys Asp Arg Pro Met Ala Val Asn Gly Gln Val Val Ile Leu Pro
        355                 360                 365

Met Met Tyr Leu Ala Leu Ser Tyr Asp His Arg Leu Ile Asp Gly Arg
    370                 375                 380

Glu Ser Val Gly Tyr Leu Val Ala Val Lys Glu Met Leu Glu Asp Pro
385                 390                 395                 400

Ala Arg Leu Leu Leu Asp Val
                405
```

-continued

```
<210> SEQ ID NO 11
<211> LENGTH: 40
<212> TYPE: PRT
<213> ORGANISM: Pantoea ananatis

<400> SEQUENCE: 11

Met Asn Leu His Glu Tyr Gln Ala Lys Gln Leu Phe Ala Arg Tyr Gly
1               5                   10                  15

Met Pro Ala Pro Thr Gly Tyr Ala Cys Thr Thr Pro Arg Glu Ala Glu
            20                  25                  30

Glu Ala Ala Ser Lys Ile Gly Ala
        35                  40

<210> SEQ ID NO 12
<211> LENGTH: 4394
<212> TYPE: DNA
<213> ORGANISM: Corynebacterium glutamicum
<220> FEATURE:
<221> NAME/KEY: CDS
<222> LOCATION: (443)..(4213)

<400> SEQUENCE: 12
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccaccctcg accccgccac cgaagccgtt atcctcaacg cctccgatcg     240
agtcactaag gacgcaccag cattatcgt cgcgcaccgc ttggcaaccg ctaaaagggc     300
cgaccgtatt cttgttgttg aacaaggacg tatcattgag gacggatctc acgacgcgtt     360
gttgtctgct aacggcacct acgcccgcat gtggcattta atggcctgac acgttatttt     420
taggagaact gtcaacaaat ta atg cta caa ctg ggg ctt agg cat aat cag      472
                           Met Leu Gln Leu Gly Leu Arg His Asn Gln
                            1               5                   10 cca acg acc aac gtt aca gtg gat aaa ata aag ctc aat aaa ccc tca      520
Pro Thr Thr Asn Val Thr Val Asp Lys Ile Lys Leu Asn Lys Pro Ser
            15                  20                  25 aga agc aag gaa aag agg cga gta cct gcc gtg agc agc gct agt act      568
Arg Ser Lys Glu Lys Arg Arg Val Pro Ala Val Ser Ser Ala Ser Thr
        30                  35                  40 ttc ggc cag aat gcg tgg ctg gta gac gag atg ttc cag cag ttc cag      616
Phe Gly Gln Asn Ala Trp Leu Val Asp Glu Met Phe Gln Gln Phe Gln
    45                  50                  55 aag gac ccc aag tcc gtg gac aag gaa tgg aga gaa ctc ttt gag gcg      664
Lys Asp Pro Lys Ser Val Asp Lys Glu Trp Arg Glu Leu Phe Glu Ala
60                  65                  70 cag ggg gga cca aat gct acc ccc gct aca aca gaa gca cag cct tca      712
Gln Gly Gly Pro Asn Ala Thr Pro Ala Thr Thr Glu Ala Gln Pro Ser
75                  80                  85                  90 gcg ccc aag gag tct gcg aaa cca gca cca aag gct gcc cct gca gcc      760
Ala Pro Lys Glu Ser Ala Lys Pro Ala Pro Lys Ala Ala Pro Ala Ala
                95                  100                 105 aag gca gca ccg cgc gta gaa acc aag ccg gcc gcc aag acc gcc cct      808
Lys Ala Ala Pro Arg Val Glu Thr Lys Pro Ala Ala Lys Thr Ala Pro
            110                 115                 120 aag gcc aag gag tcc tca gtg cca cag caa cct aag ctt ccg gag cca      856
Lys Ala Lys Glu Ser Ser Val Pro Gln Gln Pro Lys Leu Pro Glu Pro
        125                 130                 135 gga caa acc cca atc agg ggt att ttc aag tcc atc gcg aag aac atg      904
Gly Gln Thr Pro Ile Arg Gly Ile Phe Lys Ser Ile Ala Lys Asn Met
    140                 145                 150
```

|  |  |
|---|---|
| gat atc tcc ctg gaa atc cca acc gca acc tcg gtt cgc gat atg cca<br>Asp Ile Ser Leu Glu Ile Pro Thr Ala Thr Ser Val Arg Asp Met Pro<br>155                160                        165                        170 | 952 |
| gct cgc ctc atg ttc gaa aac cgc gcg atg gtc aac gat cag ctc aag<br>Ala Arg Leu Met Phe Glu Asn Arg Ala Met Val Asn Asp Gln Leu Lys<br>                    175                        180                        185 | 1000 |
| cgc acc cgc ggt ggc aag atc tcc ttc acc cac atc att ggc tac gcc<br>Arg Thr Arg Gly Gly Lys Ile Ser Phe Thr His Ile Ile Gly Tyr Ala<br>                190                        195                        200 | 1048 |
| atg gtg aag gca gtc atg gct cac ccg gac atg aac aac tcc tac gac<br>Met Val Lys Ala Val Met Ala His Pro Asp Met Asn Asn Ser Tyr Asp<br>        205                        210                        215 | 1096 |
| gtc atc gac ggc aag cca acc ctg atc gtg cct gag cac atc aac ctg<br>Val Ile Asp Gly Lys Pro Thr Leu Ile Val Pro Glu His Ile Asn Leu<br>220                225                        230 | 1144 |
| ggc ctt gcc atc gac ctt cct cag aag gac ggc tcc cgc gca ctt gtc<br>Gly Leu Ala Ile Asp Leu Pro Gln Lys Asp Gly Ser Arg Ala Leu Val<br>235                240                        245                        250 | 1192 |
| gta gca gcc atc aag gaa acc gag aag atg aac ttc tcc gag ttc ctc<br>Val Ala Ala Ile Lys Glu Thr Glu Lys Met Asn Phe Ser Glu Phe Leu<br>                    255                        260                        265 | 1240 |
| gca gca tac gaa gac atc gtg aca cgc tcc cgc aag ggc aag ctc acc<br>Ala Ala Tyr Glu Asp Ile Val Thr Arg Ser Arg Lys Gly Lys Leu Thr<br>                270                        275                        280 | 1288 |
| atg gat gac tac cag ggc gtt acc gtt tcc ttg acc aac cca ggt ggc<br>Met Asp Asp Tyr Gln Gly Val Thr Val Ser Leu Thr Asn Pro Gly Gly<br>        285                        290                        295 | 1336 |
| atc ggt acc cgc cac tct gtc cca cgt ctg acc aag ggc cag ggc acc<br>Ile Gly Thr Arg His Ser Val Pro Arg Leu Thr Lys Gly Gln Gly Thr<br>300                305                        310 | 1384 |
| atc atc ggt gtc ggt tcc atg gat tac cca gca gag ttc cag ggc gct<br>Ile Ile Gly Val Gly Ser Met Asp Tyr Pro Ala Glu Phe Gln Gly Ala<br>315                320                        325                        330 | 1432 |
| tcc gaa gac cgc ctt gca gag ctc ggc gtt gga aag ctt gtc acc atc<br>Ser Glu Asp Arg Leu Ala Glu Leu Gly Val Gly Lys Leu Val Thr Ile<br>                    335                        340                        345 | 1480 |
| acc tcc acc tac gat cac cgc gtg atc cag ggt gct gtg tcc ggt gaa<br>Thr Ser Thr Tyr Asp His Arg Val Ile Gln Gly Ala Val Ser Gly Glu<br>                350                        355                        360 | 1528 |
| ttc ctg cgt acc atg tct cgc ctg ctc acc gat gat tcc ttc tgg gat<br>Phe Leu Arg Thr Met Ser Arg Leu Leu Thr Asp Asp Ser Phe Trp Asp<br>        365                        370                        375 | 1576 |
| gag atc ttc gac gca atg aac gtt cct tac acc cca atg cgt tgg gca<br>Glu Ile Phe Asp Ala Met Asn Val Pro Tyr Thr Pro Met Arg Trp Ala<br>380                385                        390 | 1624 |
| cag gac gtt cca aac acc ggt gtt gat aag aac acc cgc gtc atg cag<br>Gln Asp Val Pro Asn Thr Gly Val Asp Lys Asn Thr Arg Val Met Gln<br>395                400                        405                        410 | 1672 |
| ctc att gag gca tac cgc tcc cgt gga cac ctc atc gct gac acc aac<br>Leu Ile Glu Ala Tyr Arg Ser Arg Gly His Leu Ile Ala Asp Thr Asn<br>                415                        420                        425 | 1720 |
| cca ctt tca tgg gtt cag cct ggc atg cca gtt cca gac cac cgc gac<br>Pro Leu Ser Trp Val Gln Pro Gly Met Pro Val Pro Asp His Arg Asp<br>        430                        435                        440 | 1768 |
| ctc gac atc gag acc cac agc ctg acc atc tgg gat ctg gac cgt acc<br>Leu Asp Ile Glu Thr His Ser Leu Thr Ile Trp Asp Leu Asp Arg Thr<br>445                450                        455 | 1816 |
| ttc agc gtc ggt ggc ttc ggc ggc aag gag acc atg acc ctg cgc gag<br>Phe Ser Val Gly Gly Phe Gly Gly Lys Glu Thr Met Thr Leu Arg Glu<br>460                465                        470 | 1864 |

-continued

| | | |
|---|---|---|
| gta ctg tcc cgc ctg cgc gct gcc tac acc ttg aag gtc ggc tcc gaa<br>Val Leu Ser Arg Leu Arg Ala Ala Tyr Thr Leu Lys Val Gly Ser Glu<br>475                             480                      485                        490 | | 1912 |
| tac acc cac atc ctg gac cgc gac gag cgc acc tgg ctg cag gac cgc<br>Tyr Thr His Ile Leu Asp Arg Asp Glu Arg Thr Trp Leu Gln Asp Arg<br>                    495                      500                      505 | | 1960 |
| ctc gaa gcc gga atg cca aag cca acc cag gca gag cag aag tac atc<br>Leu Glu Ala Gly Met Pro Lys Pro Thr Gln Ala Glu Gln Lys Tyr Ile<br>                510                      515                      520 | | 2008 |
| ctg cag aag ctg aac gcc gca gag gct ttc gag aac ttc ctg cag acc<br>Leu Gln Lys Leu Asn Ala Ala Glu Ala Phe Glu Asn Phe Leu Gln Thr<br>525                             530                      535 | | 2056 |
| aag tac gtc ggc cag aag cgc ttc tcc ctc gaa ggt gca gaa gct ctc<br>Lys Tyr Val Gly Gln Lys Arg Phe Ser Leu Glu Gly Ala Glu Ala Leu<br>540                           545                      550 | | 2104 |
| atc cca ctg atg gac tcc gcc atc gac acc gcc gca ggc cag ggc ctc<br>Ile Pro Leu Met Asp Ser Ala Ile Asp Thr Ala Ala Gly Gln Gly Leu<br>555                           560                      565                      570 | | 2152 |
| gac gaa gtt gtc atc ggt atg cca cac cgt ggt cgc ctc aac gtg ctg<br>Asp Glu Val Val Ile Gly Met Pro His Arg Gly Arg Leu Asn Val Leu<br>                    575                      580                      585 | | 2200 |
| ttc aac atc gtg ggc aag cca ctg gca tcc atc ttc aac gag ttt gaa<br>Phe Asn Ile Val Gly Lys Pro Leu Ala Ser Ile Phe Asn Glu Phe Glu<br>                    590                      595                      600 | | 2248 |
| ggc caa atg gag cag ggc cag atc ggt ggc tcc ggt gac gtg aag tac<br>Gly Gln Met Glu Gln Gly Gln Ile Gly Gly Ser Gly Asp Val Lys Tyr<br>605                             610                      615 | | 2296 |
| cac ctc ggt tcc gaa ggc cag cac ctg cag atg ttc ggc gac ggc gag<br>His Leu Gly Ser Glu Gly Gln His Leu Gln Met Phe Gly Asp Gly Glu<br>620                           625                      630 | | 2344 |
| atc aag gtc tcc ctg act gct aac ccg tcc cac ctg gaa gct gtt aac<br>Ile Lys Val Ser Leu Thr Ala Asn Pro Ser His Leu Glu Ala Val Asn<br>635                           640                      645                      650 | | 2392 |
| cca gtg atg gaa ggt atc gtc cgc gca aag cag gac tac ctg gac aag<br>Pro Val Met Glu Gly Ile Val Arg Ala Lys Gln Asp Tyr Leu Asp Lys<br>                    655                      660                      665 | | 2440 |
| ggc gta gac ggc aag act gtt gtg cca ctg ctg ctc cac ggt gac gct<br>Gly Val Asp Gly Lys Thr Val Val Pro Leu Leu Leu His Gly Asp Ala<br>                    670                      675                      680 | | 2488 |
| gca ttc gca ggc ctg ggc atc gtg cca gaa acc atc aac ctg gct aag<br>Ala Phe Ala Gly Leu Gly Ile Val Pro Glu Thr Ile Asn Leu Ala Lys<br>                    685                      690                      695 | | 2536 |
| ctg cgt ggc tac gac gtc gga ggc acc atc cac atc gtg gtg aac aac<br>Leu Arg Gly Tyr Asp Val Gly Gly Thr Ile His Ile Val Val Asn Asn<br>700                             705                      710 | | 2584 |
| cag atc ggc ttc acc acc acc cca gac tcc agc cgc tcc atg cac tac<br>Gln Ile Gly Phe Thr Thr Thr Pro Asp Ser Ser Arg Ser Met His Tyr<br>715                           720                      725                      730 | | 2632 |
| gca acc gac tac gcc aag gca ttc ggc tgc cca gtc ttc cac gtc aat<br>Ala Thr Asp Tyr Ala Lys Ala Phe Gly Cys Pro Val Phe His Val Asn<br>                    735                      740                      745 | | 2680 |
| ggt gat gac cca gag gca gtt gtc tgg gtt ggc cag ctg gca acc gag<br>Gly Asp Asp Pro Glu Ala Val Val Trp Val Gly Gln Leu Ala Thr Glu<br>750                             755                      760 | | 2728 |
| tac cgt cgt cgc ttc ggc aag gac gtc ttc atc gac ctc gtt tgc tac<br>Tyr Arg Arg Arg Phe Gly Lys Asp Val Phe Ile Asp Leu Val Cys Tyr<br>                    765                      770                      775 | | 2776 |
| cgc ctc cgc ggc cac aac gaa gct gat gat cct tcc atg acc cag cca<br>Arg Leu Arg Gly His Asn Glu Ala Asp Asp Pro Ser Met Thr Gln Pro<br>780                             785                      790 | | 2824 |

-continued

| | | |
|---|---|---|
| aag atg tat gag ctc atc acc ggc cgc gag acc gtt cgt gct cag tac<br>Lys Met Tyr Glu Leu Ile Thr Gly Arg Glu Thr Val Arg Ala Gln Tyr<br>795                 800                 805                 810 | 2872 | |
| acc gaa gac ctg ctc gga cgt gga gac ctc tcc aac gaa gat gca gaa<br>Thr Glu Asp Leu Leu Gly Arg Gly Asp Leu Ser Asn Glu Asp Ala Glu<br>                815                 820                 825 | 2920 | |
| gca gtc gtc cgc gac ttc cac gac cag atg gaa tct gtg ttc aac gaa<br>Ala Val Val Arg Asp Phe His Asp Gln Met Glu Ser Val Phe Asn Glu<br>            830                 835                 840 | 2968 | |
| gtc aag gaa ggc ggc aag aag cag gct gag gca cag acc ggc atc acc<br>Val Lys Glu Gly Gly Lys Lys Gln Ala Glu Ala Gln Thr Gly Ile Thr<br>845                 850                 855 | 3016 | |
| ggc tcc cag aag ctt cca cac ggc ctt gag acc aac atc tcc cgt gaa<br>Gly Ser Gln Lys Leu Pro His Gly Leu Glu Thr Asn Ile Ser Arg Glu<br>    860                 865                 870 | 3064 | |
| gag ctc ctg gaa ctg gga cag gct ttc gcc aac acc cca gaa ggc ttc<br>Glu Leu Leu Glu Leu Gly Gln Ala Phe Ala Asn Thr Pro Glu Gly Phe<br>875                 880                 885                 890 | 3112 | |
| aac tac cac cca cgt gtg gct cca gtt gct aag aag cgc gtc tcc tct<br>Asn Tyr His Pro Arg Val Ala Pro Val Ala Lys Lys Arg Val Ser Ser<br>                895                 900                 905 | 3160 | |
| gtc acc gaa ggt ggc atc gac tgg gca tgg ggc gag ctc ctc gcc ttc<br>Val Thr Glu Gly Gly Ile Asp Trp Ala Trp Gly Glu Leu Leu Ala Phe<br>            910                 915                 920 | 3208 | |
| ggt tcc ctg gct aac tcc ggc cgc ttg gtt cgc ctt gca ggt gaa gat<br>Gly Ser Leu Ala Asn Ser Gly Arg Leu Val Arg Leu Ala Gly Glu Asp<br>        925                 930                 935 | 3256 | |
| tcc cgc cgc ggt acc ttc acc cag cgc cac gca gtt gcc atc gac cca<br>Ser Arg Arg Gly Thr Phe Thr Gln Arg His Ala Val Ala Ile Asp Pro<br>940                 945                 950 | 3304 | |
| gcg acc gct gaa gag ttc aac cca ctc cac gag ctt gca cag tcc aag<br>Ala Thr Ala Glu Glu Phe Asn Pro Leu His Glu Leu Ala Gln Ser Lys<br>955                 960                 965                 970 | 3352 | |
| ggc aac aac ggt aag ttc ctg gtc tac aac tcc gca ctg acc gag tac<br>Gly Asn Asn Gly Lys Phe Leu Val Tyr Asn Ser Ala Leu Thr Glu Tyr<br>                975                 980                 985 | 3400 | |
| gca ggc atg ggc ttc gag tac ggc tac tcc gta gga aac gaa gac tcc<br>Ala Gly Met Gly Phe Glu Tyr Gly Tyr Ser Val Gly Asn Glu Asp Ser<br>            990                 995                 1000 | 3448 | |
| gtc gtt gca tgg gaa gca cag ttc ggc gac ttc gcc aac ggc gct<br>Val Val Ala Trp Glu Ala Gln Phe Gly Asp Phe Ala Asn Gly Ala<br>        1005                 1010                 1015 | 3493 | |
| cag acc atc atc gat gag tac gtc tcc tca ggc gaa gct aag tgg<br>Gln Thr Ile Ile Asp Glu Tyr Val Ser Ser Gly Glu Ala Lys Trp<br>1020                 1025                 1030 | 3538 | |
| ggc cag acc tcc aag ctg atc ctt ctg ctg cct cac ggc tac gaa<br>Gly Gln Thr Ser Lys Leu Ile Leu Leu Leu Pro His Gly Tyr Glu<br>    1035                 1040                 1045 | 3583 | |
| ggc cag ggc cca gac cac tct tcc gca cgt atc gag cgc ttc ctg<br>Gly Gln Gly Pro Asp His Ser Ser Ala Arg Ile Glu Arg Phe Leu<br>1050                 1055                 1060 | 3628 | |
| cag ctg tgc gct gag ggt tcc atg act gtt gct cag cca tcc acc<br>Gln Leu Cys Ala Glu Gly Ser Met Thr Val Ala Gln Pro Ser Thr<br>        1065                 1070                 1075 | 3673 | |
| cca gca aac cac ttc cac ctg ctg cgt cgt cac gct ctg tcc gac<br>Pro Ala Asn His Phe His Leu Leu Arg Arg His Ala Leu Ser Asp<br>    1080                 1085                 1090 | 3718 | |
| ctg aag cgt cca ctg gtt atc ttc acc ccg aag tcc atg ctg cgt<br>Leu Lys Arg Pro Leu Val Ile Phe Thr Pro Lys Ser Met Leu Arg<br>1095                 1100                 1105 | 3763 | |

```
aac aag gct gct gcc tcc gca cca gaa gac ttc act gag gtc acc      3808
Asn Lys Ala Ala Ala Ser Ala Pro Glu Asp Phe Thr Glu Val Thr
        1110            1115                1120 aag ttc caa tcc gtg atc gac gat cca aac gtt gca gat gca gcc      3853
Lys Phe Gln Ser Val Ile Asp Asp Pro Asn Val Ala Asp Ala Ala
    1125            1130                1135 aag gtg aag aag gtc atg ctg gtc tcc ggc aag ctg tac tac gaa      3898
Lys Val Lys Lys Val Met Leu Val Ser Gly Lys Leu Tyr Tyr Glu
1140            1145                1150 ttg gca aag cgc aag gag aag gac gga cgc gac gac atc gcg atc      3943
Leu Ala Lys Arg Lys Glu Lys Asp Gly Arg Asp Asp Ile Ala Ile
        1155            1160                1165 gtt cgt atc gaa atg ctc cac cca att ccg ttc aac cgc atc tcc      3988
Val Arg Ile Glu Met Leu His Pro Ile Pro Phe Asn Arg Ile Ser
    1170            1175                1180 gag gct ctt gcc ggc tac cct aac gct gag gaa gtc ctc ttc gtt      4033
Glu Ala Leu Ala Gly Tyr Pro Asn Ala Glu Glu Val Leu Phe Val
1185            1190                1195 cag gat gag cca gca aac cag ggc cca tgg ccg ttc tac cag gag      4078
Gln Asp Glu Pro Ala Asn Gln Gly Pro Trp Pro Phe Tyr Gln Glu
        1200            1205                1210 cac ctc cca gag ctg atc ccg aac atg cca aag atg cgc cgc gtt      4123
His Leu Pro Glu Leu Ile Pro Asn Met Pro Lys Met Arg Arg Val
    1215            1220                1225 tcc cgc cgc gct cag tcc tcc acc gca act ggt gtt gct aag gtg      4168
Ser Arg Arg Ala Gln Ser Ser Thr Ala Thr Gly Val Ala Lys Val
1230            1235                1240 cac cag ctg gag gag aag cag ctt atc gac gag gct ttc gag gct      4213
His Gln Leu Glu Glu Lys Gln Leu Ile Asp Glu Ala Phe Glu Ala
        1245            1250                1255 taagtcttta tagtcctgca ctagcctaga gggccttatg cagtgtgaat cacacagcat    4273
aaggcccttt ttgctgccgt ggttgcctaa ggtggaaggc atgaaacgaa tctgtgcggt    4333
cacgatctct tcagtacttt tgctaagtgg ctgctcctcc acttccacca cgcagctcga    4393
g                                                                    4394

<210> SEQ ID NO 13
<211> LENGTH: 1257
<212> TYPE: PRT
<213> ORGANISM: Corynebacterium glutamicum

<400> SEQUENCE: 13

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125
```

```
Val Pro Gln Gln Pro Lys Leu Pro Glu Pro Gly Gln Thr Pro Ile Arg
    130                 135                 140
Gly Ile Phe Lys Ser Ile Ala Lys Asn Met Asp Ile Ser Leu Glu Ile
145                 150                 155                 160
Pro Thr Ala Thr Ser Val Arg Asp Met Pro Ala Arg Leu Met Phe Glu
                165                 170                 175
Asn Arg Ala Met Val Asn Asp Gln Leu Lys Arg Thr Arg Gly Gly Lys
                180                 185                 190
Ile Ser Phe Thr His Ile Ile Gly Tyr Ala Met Val Lys Ala Val Met
                195                 200                 205
Ala His Pro Asp Met Asn Asn Ser Tyr Asp Val Ile Asp Gly Lys Pro
    210                 215                 220
Thr Leu Ile Val Pro Glu His Ile Asn Leu Gly Leu Ala Ile Asp Leu
225                 230                 235                 240
Pro Gln Lys Asp Gly Ser Arg Ala Leu Val Val Ala Ala Ile Lys Glu
                245                 250                 255
Thr Glu Lys Met Asn Phe Ser Glu Phe Leu Ala Ala Tyr Glu Asp Ile
                260                 265                 270
Val Thr Arg Ser Arg Lys Gly Lys Leu Thr Met Asp Asp Tyr Gln Gly
                275                 280                 285
Val Thr Val Ser Leu Thr Asn Pro Gly Gly Ile Gly Thr Arg His Ser
    290                 295                 300
Val Pro Arg Leu Thr Lys Gly Gln Gly Thr Ile Ile Gly Val Gly Ser
305                 310                 315                 320
Met Asp Tyr Pro Ala Glu Phe Gln Gly Ala Ser Glu Asp Arg Leu Ala
                325                 330                 335
Glu Leu Gly Val Gly Lys Leu Val Thr Ile Thr Ser Thr Tyr Asp His
                340                 345                 350
Arg Val Ile Gln Gly Ala Val Ser Gly Glu Phe Leu Arg Thr Met Ser
                355                 360                 365
Arg Leu Leu Thr Asp Asp Ser Phe Trp Asp Glu Ile Phe Asp Ala Met
    370                 375                 380
Asn Val Pro Tyr Thr Pro Met Arg Trp Ala Gln Asp Val Pro Asn Thr
385                 390                 395                 400
Gly Val Asp Lys Asn Thr Arg Val Met Gln Leu Ile Glu Ala Tyr Arg
                405                 410                 415
Ser Arg Gly His Leu Ile Ala Asp Thr Asn Pro Leu Ser Trp Val Gln
                420                 425                 430
Pro Gly Met Pro Val Pro Asp His Arg Asp Leu Asp Ile Glu Thr His
                435                 440                 445
Ser Leu Thr Ile Trp Asp Leu Asp Arg Thr Phe Ser Val Gly Gly Phe
    450                 455                 460
Gly Gly Lys Glu Thr Met Thr Leu Arg Glu Val Leu Ser Arg Leu Arg
465                 470                 475                 480
Ala Ala Tyr Thr Leu Lys Val Gly Ser Glu Tyr Thr His Ile Leu Asp
                485                 490                 495
Arg Asp Glu Arg Thr Trp Leu Gln Asp Arg Leu Glu Ala Gly Met Pro
                500                 505                 510
Lys Pro Thr Gln Ala Glu Gln Lys Tyr Ile Leu Gln Lys Leu Asn Ala
                515                 520                 525
Ala Glu Ala Phe Glu Asn Phe Leu Gln Thr Lys Tyr Val Gly Gln Lys
    530                 535                 540
Arg Phe Ser Leu Glu Gly Ala Glu Ala Leu Ile Pro Leu Met Asp Ser
```

```
                545                 550                 555                 560
        Ala Ile Asp Thr Ala Ala Gly Gln Gly Leu Asp Glu Val Val Ile Gly
                        565                 570                 575

Met Pro His Arg Gly Arg Leu Asn Val Leu Phe Asn Ile Val Gly Lys
                        580                 585                 590

Pro Leu Ala Ser Ile Phe Asn Glu Phe Glu Gly Gln Met Glu Gln Gly
                        595                 600                 605

Gln Ile Gly Gly Ser Gly Asp Val Lys Tyr His Leu Gly Ser Glu Gly
                        610                 615                 620

Gln His Leu Gln Met Phe Gly Asp Gly Glu Ile Lys Val Ser Leu Thr
        625                 630                 635                 640

Ala Asn Pro Ser His Leu Glu Ala Val Asn Pro Val Met Glu Gly Ile
                        645                 650                 655

Val Arg Ala Lys Gln Asp Tyr Leu Asp Lys Gly Val Asp Gly Lys Thr
                        660                 665                 670

Val Val Pro Leu Leu His Gly Asp Ala Ala Phe Ala Gly Leu Gly
                        675                 680                 685

Ile Val Pro Glu Thr Ile Asn Leu Ala Lys Leu Arg Gly Tyr Asp Val
                        690                 695                 700

Gly Gly Thr Ile His Ile Val Val Asn Asn Gln Ile Gly Phe Thr Thr
        705                 710                 715                 720

Thr Pro Asp Ser Ser Arg Ser Met His Tyr Ala Thr Asp Tyr Ala Lys
                        725                 730                 735

Ala Phe Gly Cys Pro Val Phe His Val Asn Gly Asp Asp Pro Glu Ala
                        740                 745                 750

Val Val Trp Val Gly Gln Leu Ala Thr Glu Tyr Arg Arg Arg Phe Gly
                        755                 760                 765

Lys Asp Val Phe Ile Asp Leu Val Cys Tyr Arg Leu Arg Gly His Asn
                        770                 775                 780

Glu Ala Asp Asp Pro Ser Met Thr Gln Pro Lys Met Tyr Glu Leu Ile
        785                 790                 795                 800

Thr Gly Arg Glu Thr Val Arg Ala Gln Tyr Thr Glu Asp Leu Leu Gly
                        805                 810                 815

Arg Gly Asp Leu Ser Asn Glu Asp Ala Glu Ala Val Val Arg Asp Phe
                        820                 825                 830

His Asp Gln Met Glu Ser Val Phe Asn Glu Val Lys Glu Gly Gly Lys
                        835                 840                 845

Lys Gln Ala Glu Ala Gln Thr Gly Ile Thr Gly Ser Gln Lys Leu Pro
                        850                 855                 860

His Gly Leu Glu Thr Asn Ile Ser Arg Glu Glu Leu Glu Leu Gly
        865                 870                 875                 880

Gln Ala Phe Ala Asn Thr Pro Glu Gly Phe Asn Tyr His Pro Arg Val
                        885                 890                 895

Ala Pro Val Ala Lys Lys Arg Val Ser Ser Val Thr Glu Gly Gly Ile
                        900                 905                 910

Asp Trp Ala Trp Gly Glu Leu Leu Ala Phe Gly Ser Leu Ala Asn Ser
                        915                 920                 925

Gly Arg Leu Val Arg Leu Ala Gly Glu Asp Ser Arg Arg Gly Thr Phe
                        930                 935                 940

Thr Gln Arg His Ala Val Ala Ile Asp Pro Ala Thr Ala Glu Glu Phe
        945                 950                 955                 960

Asn Pro Leu His Glu Leu Ala Gln Ser Lys Gly Asn Asn Gly Lys Phe
                        965                 970                 975
```

```
Leu Val Tyr Asn Ser Ala Leu Thr Glu Tyr Ala Gly Met Gly Phe Glu
            980                 985                 990

Tyr Gly Tyr Ser Val Gly Asn Glu Asp Ser Val Val Ala Trp Glu Ala
        995                1000                1005

Gln Phe Gly Asp Phe Ala Asn Gly Ala Gln Thr Ile Ile Asp Glu
    1010                1015                1020

Tyr Val Ser Ser Gly Glu Ala Lys Trp Gly Gln Thr Ser Lys Leu
    1025                1030                1035

Ile Leu Leu Leu Pro His Gly Tyr Gly Gln Gly Pro Asp His
    1040                1045                1050

Ser Ser Ala Arg Ile Glu Arg Phe Leu Gln Leu Cys Ala Glu Gly
    1055                1060                1065

Ser Met Thr Val Ala Gln Pro Ser Thr Pro Ala Asn His Phe His
    1070                1075                1080

Leu Leu Arg Arg His Ala Leu Ser Asp Leu Lys Arg Pro Leu Val
    1085                1090                1095

Ile Phe Thr Pro Lys Ser Met Leu Arg Asn Lys Ala Ala Ser
    1100                1105                1110

Ala Pro Glu Asp Phe Thr Glu Val Thr Lys Phe Gln Ser Val Ile
    1115                1120                1125

Asp Asp Pro Asn Val Ala Asp Ala Ala Lys Val Lys Lys Val Met
    1130                1135                1140

Leu Val Ser Gly Lys Leu Tyr Tyr Glu Leu Ala Lys Arg Lys Glu
    1145                1150                1155

Lys Asp Gly Arg Asp Asp Ile Ala Ile Val Arg Ile Glu Met Leu
    1160                1165                1170

His Pro Ile Pro Phe Asn Arg Ile Ser Glu Ala Leu Ala Gly Tyr
    1175                1180                1185

Pro Asn Ala Glu Glu Val Leu Phe Val Gln Asp Glu Pro Ala Asn
    1190                1195                1200

Gln Gly Pro Trp Pro Phe Tyr Gln Glu His Leu Pro Glu Leu Ile
    1205                1210                1215

Pro Asn Met Pro Lys Met Arg Arg Val Ser Arg Arg Ala Gln Ser
    1220                1225                1230

Ser Thr Ala Thr Gly Val Ala Lys Val His Gln Leu Glu Glu Lys
    1235                1240                1245

Gln Leu Ile Asp Glu Ala Phe Glu Ala
    1250                1255

<210> SEQ ID NO 14
<211> LENGTH: 2028
<212> TYPE: DNA
<213> ORGANISM: Corynebacterium glutamicum
<220> FEATURE:
<221> NAME/KEY: CDS
<222> LOCATION: (1)..(2028)

<400> SEQUENCE: 14 atg gcg ttc tcc gta gag atg ccc gag ctg ggc gaa tca gta acc gaa     48
Met Ala Phe Ser Val Glu Met Pro Glu Leu Gly Glu Ser Val Thr Glu
1               5                  10                  15 ggc acg atc acc cag tgg ttg aag tct gtt ggt gac act gtt gag gta     96
Gly Thr Ile Thr Gln Trp Leu Lys Ser Val Gly Asp Thr Val Glu Val
                20                  25                  30 gat gag ccg ttg ctc gag gtc tca act gac aag gtc gac acc gag att    144
Asp Glu Pro Leu Leu Glu Val Ser Thr Asp Lys Val Asp Thr Glu Ile
            35                  40                  45
```

```
ccc tct cct gtc gcc ggt gtc atc cta gag att aag gct gaa gag gat      192
Pro Ser Pro Val Ala Gly Val Ile Leu Glu Ile Lys Ala Glu Glu Asp
    50              55                  60 gac acc gtc gac gtc ggc ggt gtc att gca ata atc ggc gat gct gat      240
Asp Thr Val Asp Val Gly Gly Val Ile Ala Ile Ile Gly Asp Ala Asp
65              70                  75                  80 gag act cct gcc aac gaa gct cct gcc gac gag gca cca gct cct gcc      288
Glu Thr Pro Ala Asn Glu Ala Pro Ala Asp Glu Ala Pro Ala Pro Ala
                85                  90                  95 gaa gag gaa gaa cca gtt aag gaa gag cca aag aag gag gca gct cct      336
Glu Glu Glu Glu Pro Val Lys Glu Glu Pro Lys Lys Glu Ala Ala Pro
                    100                 105                 110 gaa gct cca gca gca act ggc gcc gca acc gat gtg gaa atg cca gaa      384
Glu Ala Pro Ala Ala Thr Gly Ala Ala Thr Asp Val Glu Met Pro Glu
            115                 120                 125 ctc ggc gaa tcc gtc acc gaa ggc acc att acc cag tgg ctc aag gct      432
Leu Gly Glu Ser Val Thr Glu Gly Thr Ile Thr Gln Trp Leu Lys Ala
        130                 135                 140 gtc ggc gac acc gtc gaa gta gac gaa cca ctt ctt gag gtc tcc acc      480
Val Gly Asp Thr Val Glu Val Asp Glu Pro Leu Leu Glu Val Ser Thr
145                 150                 155                 160 gac aag gtc gac acc gaa atc cca tcc cca gta gca ggc acc atc gtg      528
Asp Lys Val Asp Thr Glu Ile Pro Ser Pro Val Ala Gly Thr Ile Val
                165                 170                 175 gag atc ctt gca gac gaa gac gac acc gtc gac gtc ggc gca gtc atc      576
Glu Ile Leu Ala Asp Glu Asp Asp Thr Val Asp Val Gly Ala Val Ile
            180                 185                 190 gcc cgc atc ggt gac gca aac gca gct gca cct gcc gaa gag gaa           624
Ala Arg Ile Gly Asp Ala Asn Ala Ala Ala Pro Ala Glu Glu Glu
        195                 200                 205 gca gct cct gcc gaa gag gaa gaa cca gtt aag gaa gag cca aag aag      672
Ala Ala Pro Ala Glu Glu Glu Glu Pro Val Lys Glu Glu Pro Lys Lys
210                 215                 220 gag gca gct cct gaa gct cca gca gca act ggc gcc gca acc gat gtg      720
Glu Ala Ala Pro Glu Ala Pro Ala Ala Thr Gly Ala Ala Thr Asp Val
225                 230                 235                 240 gaa atg cca gaa ctc ggc gaa tcc gtc acc gaa ggc acc att acc cag      768
Glu Met Pro Glu Leu Gly Glu Ser Val Thr Glu Gly Thr Ile Thr Gln
                245                 250                 255 tgg ctc aag gct gtc ggc gac acc gtc gaa gta gac gaa cca ctt ctt      816
Trp Leu Lys Ala Val Gly Asp Thr Val Glu Val Asp Glu Pro Leu Leu
            260                 265                 270 gag gtc tcc acc gac aag gtc gac acc gaa atc cca tcc cca gta gca      864
Glu Val Ser Thr Asp Lys Val Asp Thr Glu Ile Pro Ser Pro Val Ala
        275                 280                 285 ggc acc atc gtg gag atc ctt gca gac gaa gac gac acc gtc gac gtc      912
Gly Thr Ile Val Glu Ile Leu Ala Asp Glu Asp Asp Thr Val Asp Val
290                 295                 300 ggc gca gtc atc gcc cgc atc ggt gac gca aac gca gct gca gca cct      960
Gly Ala Val Ile Ala Arg Ile Gly Asp Ala Asn Ala Ala Ala Ala Pro
305                 310                 315                 320 gcc gaa gag gaa gca gct cct gcc gaa gag gag gaa cca gtt aag gaa     1008
Ala Glu Glu Glu Ala Ala Pro Ala Glu Glu Glu Glu Pro Val Lys Glu
                325                 330                 335 gag cca aag aag gaa gag ccc aag aag gaa gag ccc aag aag gaa gca     1056
Glu Pro Lys Lys Glu Glu Pro Lys Lys Glu Glu Pro Lys Lys Glu Ala
            340                 345                 350 gct act aca cct gct gcg gca tcc gca act gtg tcc gct tct ggc gac     1104
Ala Thr Thr Pro Ala Ala Ala Ser Ala Thr Val Ser Ala Ser Gly Asp
        355                 360                 365
```

```
                                                              -continued aac gtt cca tac gtc acc cca ctg gtg cgc aag ctt gct gaa aag cac     1152
Asn Val Pro Tyr Val Thr Pro Leu Val Arg Lys Leu Ala Glu Lys His
370             375                 380 ggc gtt gac ttg aac acc gtg acc ggt acc ggt atc ggt ggc cgt atc     1200
Gly Val Asp Leu Asn Thr Val Thr Gly Thr Gly Ile Gly Gly Arg Ile
385             390                 395                 400 cgc aag cag gat gtt ttg gct gct gcg aac ggc gag gct gca cct gct     1248
Arg Lys Gln Asp Val Leu Ala Ala Ala Asn Gly Glu Ala Ala Pro Ala
                405                 410                 415 gag gct gct gct cct gtt tcc gct tgg tcc act aag tct gtt gac cct     1296
Glu Ala Ala Ala Pro Val Ser Ala Trp Ser Thr Lys Ser Val Asp Pro
    420                 425                 430 gag aag gct aag ctc cgt ggt acc act cag aag gtc aac cgc atc cgt     1344
Glu Lys Ala Lys Leu Arg Gly Thr Thr Gln Lys Val Asn Arg Ile Arg
            435                 440                 445 gag atc acc gcg atg aag acc gtc gag gct ctg cag att tct gct cag     1392
Glu Ile Thr Ala Met Lys Thr Val Glu Ala Leu Gln Ile Ser Ala Gln
450                 455                 460 ctc acc cag ctg cac gag gtc gat atg act cgc gtt gct gag ctg cgt     1440
Leu Thr Gln Leu His Glu Val Asp Met Thr Arg Val Ala Glu Leu Arg
465                 470                 475                 480 aag aag aac aag ccc gcg ttc atc gag aag cac ggt gtg aac ctc act     1488
Lys Lys Asn Lys Pro Ala Phe Ile Glu Lys His Gly Val Asn Leu Thr
                485                 490                 495 tac ctg cca ttc ttc gtg aag gca gtt gtc gag gct ttg gtt tcc cat     1536
Tyr Leu Pro Phe Phe Val Lys Ala Val Val Glu Ala Leu Val Ser His
                500                 505                 510 cca aac gtc aac gcg tct ttc aac gcg aag acc aag gag atg acc tac     1584
Pro Asn Val Asn Ala Ser Phe Asn Ala Lys Thr Lys Glu Met Thr Tyr
            515                 520                 525 cac tcc tcc gtt aac ctc tcc atc gct gtt gat acc cca gct ggt ctg     1632
His Ser Ser Val Asn Leu Ser Ile Ala Val Asp Thr Pro Ala Gly Leu
530                 535                 540 ttg acc cca gtc att cac gat gct cag gat ctc tcc atc cca gag atc     1680
Leu Thr Pro Val Ile His Asp Ala Gln Asp Leu Ser Ile Pro Glu Ile
545                 550                 555                 560 gca aag gca att gtt gac ctg gct gat cgt tca cgc aac aac aag ctg     1728
Ala Lys Ala Ile Val Asp Leu Ala Asp Arg Ser Arg Asn Asn Lys Leu
                565                 570                 575 aag cca aac gat ctg tcc ggt ggc acc ttc acc atc acc aac att ggt     1776
Lys Pro Asn Asp Leu Ser Gly Gly Thr Phe Thr Ile Thr Asn Ile Gly
                580                 585                 590 tct gaa ggc gca ctg tct gat acc cca atc ctg gtt cca cca cag gct     1824
Ser Glu Gly Ala Leu Ser Asp Thr Pro Ile Leu Val Pro Pro Gln Ala
            595                 600                 605 ggc atc ttg ggc acc ggc gcg atc gtg aag cgt cca gtt gtc atc acc     1872
Gly Ile Leu Gly Thr Gly Ala Ile Val Lys Arg Pro Val Val Ile Thr
        610                 615                 620 gag gat gga att gat tcc atc gcg atc cgt cag atg gtc ttc cta cca     1920
Glu Asp Gly Ile Asp Ser Ile Ala Ile Arg Gln Met Val Phe Leu Pro
625                 630                 635                 640 ctg acc tac gac cac cag gtt gta gat ggc gca gat gct ggt cgc ttc     1968
Leu Thr Tyr Asp His Gln Val Val Asp Gly Ala Asp Ala Gly Arg Phe
                645                 650                 655 ctg acc acc atc aag gac cgc ctt gag acc gct aac ttc gaa ggc gat     2016
Leu Thr Thr Ile Lys Asp Arg Leu Glu Thr Ala Asn Phe Glu Gly Asp
                660                 665                 670 ctg cag ctc taa                                                     2028
Leu Gln Leu
        675
```

<210> SEQ ID NO 15
<211> LENGTH: 675
<212> TYPE: PRT
<213> ORGANISM: Corynebacterium glutamicum

<400> SEQUENCE: 15

Met Ala Phe Ser Val Glu Met Pro Glu Leu Gly Glu Ser Val Thr Glu
1               5                   10                  15

Gly Thr Ile Thr Gln Trp Leu Lys Ser Val Gly Asp Thr Val Glu Val
            20                  25                  30

Asp Glu Pro Leu Leu Glu Val Ser Thr Asp Lys Val Asp Thr Glu Ile
        35                  40                  45

Pro Ser Pro Val Ala Gly Val Ile Leu Glu Ile Lys Ala Glu Glu Asp
    50                  55                  60

Asp Thr Val Asp Val Gly Gly Val Ile Ala Ile Gly Asp Ala Asp
65                  70                  75                  80

Glu Thr Pro Ala Asn Glu Ala Pro Ala Asp Glu Ala Pro Ala
                85                  90                  95

Glu Glu Glu Glu Pro Val Lys Glu Pro Lys Lys Glu Ala Ala Pro
            100                 105                 110

Glu Ala Pro Ala Ala Thr Gly Ala Ala Thr Asp Val Glu Met Pro Glu
        115                 120                 125

Leu Gly Glu Ser Val Thr Glu Gly Thr Ile Thr Gln Trp Leu Lys Ala
    130                 135                 140

Val Gly Asp Thr Val Glu Val Asp Glu Pro Leu Leu Glu Val Ser Thr
145                 150                 155                 160

Asp Lys Val Asp Thr Glu Ile Pro Ser Pro Val Ala Gly Thr Ile Val
                165                 170                 175

Glu Ile Leu Ala Asp Glu Asp Thr Val Asp Val Gly Ala Val Ile
            180                 185                 190

Ala Arg Ile Gly Asp Ala Asn Ala Ala Ala Pro Ala Glu Glu Glu
        195                 200                 205

Ala Ala Pro Ala Glu Glu Glu Pro Val Lys Glu Glu Pro Lys Lys
    210                 215                 220

Glu Ala Ala Pro Glu Ala Pro Ala Ala Thr Gly Ala Ala Thr Asp Val
225                 230                 235                 240

Glu Met Pro Glu Leu Gly Glu Ser Val Thr Glu Gly Thr Ile Thr Gln
                245                 250                 255

Trp Leu Lys Ala Val Gly Asp Thr Val Glu Val Asp Glu Pro Leu Leu
            260                 265                 270

Glu Val Ser Thr Asp Lys Val Asp Thr Glu Ile Pro Ser Pro Val Ala
        275                 280                 285

Gly Thr Ile Val Glu Ile Leu Ala Asp Glu Asp Thr Val Asp Val
    290                 295                 300

Gly Ala Val Ile Ala Arg Ile Gly Asp Ala Asn Ala Ala Ala Ala Pro
305                 310                 315                 320

Ala Glu Glu Glu Ala Ala Pro Ala Glu Glu Glu Pro Val Lys Glu
                325                 330                 335

Glu Pro Lys Lys Glu Glu Pro Lys Lys Glu Glu Pro Lys Lys Glu Ala
            340                 345                 350

Ala Thr Thr Pro Ala Ala Ala Ser Ala Thr Val Ser Ala Ser Gly Asp
        355                 360                 365

Asn Val Pro Tyr Val Thr Pro Leu Val Arg Lys Leu Ala Glu Lys His
    370                 375                 380

```
Gly Val Asp Leu Asn Thr Val Thr Gly Thr Gly Ile Gly Gly Arg Ile
385                 390                 395                 400

Arg Lys Gln Asp Val Leu Ala Ala Ala Asn Gly Glu Ala Ala Pro Ala
            405                 410                 415

Glu Ala Ala Ala Pro Val Ser Ala Trp Ser Thr Lys Ser Val Asp Pro
        420                 425                 430

Glu Lys Ala Lys Leu Arg Gly Thr Thr Gln Lys Val Asn Arg Ile Arg
    435                 440                 445

Glu Ile Thr Ala Met Lys Thr Val Glu Ala Leu Gln Ile Ser Ala Gln
450                 455                 460

Leu Thr Gln Leu His Glu Val Asp Met Thr Arg Val Ala Glu Leu Arg
465                 470                 475                 480

Lys Lys Asn Lys Pro Ala Phe Ile Glu Lys His Gly Val Asn Leu Thr
                485                 490                 495

Tyr Leu Pro Phe Phe Val Lys Ala Val Val Glu Ala Leu Val Ser His
            500                 505                 510

Pro Asn Val Asn Ala Ser Phe Asn Ala Lys Thr Lys Glu Met Thr Tyr
        515                 520                 525

His Ser Ser Val Asn Leu Ser Ile Ala Val Asp Thr Pro Ala Gly Leu
    530                 535                 540

Leu Thr Pro Val Ile His Asp Ala Gln Asp Leu Ser Ile Pro Glu Ile
545                 550                 555                 560

Ala Lys Ala Ile Val Asp Leu Ala Asp Arg Ser Arg Asn Asn Lys Leu
                565                 570                 575

Lys Pro Asn Asp Leu Ser Gly Gly Thr Phe Thr Ile Thr Asn Ile Gly
            580                 585                 590

Ser Glu Gly Ala Leu Ser Asp Thr Pro Ile Leu Val Pro Pro Gln Ala
        595                 600                 605

Gly Ile Leu Gly Thr Gly Ala Ile Val Lys Arg Pro Val Val Ile Thr
    610                 615                 620

Glu Asp Gly Ile Asp Ser Ile Ala Ile Arg Gln Met Val Phe Leu Pro
625                 630                 635                 640

Leu Thr Tyr Asp His Gln Val Val Asp Gly Ala Asp Ala Gly Arg Phe
                645                 650                 655

Leu Thr Thr Ile Lys Asp Arg Leu Glu Thr Ala Asn Phe Glu Gly Asp
            660                 665                 670

Leu Gln Leu
        675

<210> SEQ ID NO 16
<211> LENGTH: 1308
<212> TYPE: DNA
<213> ORGANISM: Pantoea ananatis

<400> SEQUENCE: 16
atgagcagaa tcatgacgcc cgtgaactgg gaagcctgca gcagcgaggc gcagcaggcg      60
ctgttggcac gccctgcgct cgcctcgtct gacagcatca gccagatcgt gcgcgatgtg     120
ttggtcagag tgaaagagga aggcgatgcg gctttacgag aattcagcgc gcgctttgac     180
aaggttgaaa cagacgacct gcgcgttacg ccacagcaga tgcaggcggc cagcgatcgc     240
cttggtgacg agctgaaaca ggcgatggcc gtggccattg caatattga aacctttcac      300 cgtgcgcaga tcctgccgcc ggtggatgtg gaaacgcagc ccggcgtgcg ctgtcagcaa     360
attacgcgcc cgatgaaatc ggtgggcttg tatattccgg cggttctgc cccgctgttt      420 tctaccgttc tgatgctggc taccccggcg cggattgcgg gctgtggtcg cgtggtgctg     480
```

```
tgctcgcccc cgccgattgc tgatgaaatt ctctacgcgg ccaaactttg cggtgtggaa      540
gaagtgttcc aggtgggtgg atcacaggcg attgccgccc tggcttttgg caccgaaagc      600
atccctaagg tagataaaat ttttggtccg ggcaacgcgt gggttaccga agccaaacgt      660
caggtcagcc agcgccttga tggcgcggcg attgatatgc ccgctggccc gtcggaagtg      720
ctggtgattg ccgatgaagg tgccacaccg gccttcgttg cctctgatct gctgtcgcag      780
gcggaacacg gccctgactc gcaggtgatt ttactgacgc cttcgctggc gctggccgag      840
cgcgtcgccg aggcggtgga ggatcagctg gcccagttgc cacgtgcggc gacagcccgc      900
caggcactgg aaagcagccg cctgatcgtc gcccgggata tgcagcaatg cattgcgatc      960
tccaaccgct atggtccgga gcacctgatt ctgcaaaccc gcacgccacg ggatctggtg     1020
gaacagatta ccagcgccgg ttcggttttc ctgggcgact ggtcaccgga atccgcagga     1080
gattatgctt cgggcaccaa ccacgtgctg ccgacctacg gctataccgc gacatgctcc     1140
agcctgggcc tggccgactt tcagaaacgc atgacgtac aggagctgac gccgcagggc      1200
ttcctgaacc tggcggcgac catcgaaacc ctggcggccg ctgaacagct gcacgcccac     1260
aaaaatgccg tcacgttgcg cgttgccgca ctcaaggagc aagcatga                 1308
```

<210> SEQ ID NO 17
<211> LENGTH: 68
<212> TYPE: DNA
<213> ORGANISM: Artificial
<220> FEATURE:
<223> OTHER INFORMATION: primer

<400> SEQUENCE: 17

```
ccatagcggt tggagatcgc aatgcattgc tgcatatccc tgaagcctgc tttttatac      60 taagttgg                                                              68
```

<210> SEQ ID NO 18
<211> LENGTH: 68
<212> TYPE: DNA
<213> ORGANISM: Artificial
<220> FEATURE:
<223> OTHER INFORMATION: primer

<400> SEQUENCE: 18

```
gcccgccagg cactggaaag cagccgcctg atcgtcgccc cgctcaagtt agtataaaaa      60
agctgaac                                                              68
```

<210> SEQ ID NO 19
<211> LENGTH: 33
<212> TYPE: DNA
<213> ORGANISM: Artificial
<220> FEATURE:
<223> OTHER INFORMATION: primer

<400> SEQUENCE: 19

```
tagcgagatc tctgatgtcc ggcggtgctt ttg                                   33
```

<210> SEQ ID NO 20
<211> LENGTH: 32
<212> TYPE: DNA
<213> ORGANISM: Artificial
<220> FEATURE:
<223> OTHER INFORMATION: primer

<400> SEQUENCE: 20

```
aaaaagagct cttacgcccc gccctgccac tc                                    32
```

<210> SEQ ID NO 21
<211> LENGTH: 34
<212> TYPE: DNA
<213> ORGANISM: Artificial
<220> FEATURE:
<223> OTHER INFORMATION: primer

<400> SEQUENCE: 21
caggatctag aaggagacat gaacgatgaa catc                                    34

<210> SEQ ID NO 22
<211> LENGTH: 36
<212> TYPE: DNA
<213> ORGANISM: Artificial
<220> FEATURE:
<223> OTHER INFORMATION: primer

<400> SEQUENCE: 22
gataaggatc cgaaataaaa gaaaatgcca atagga                                  36

<210> SEQ ID NO 23
<211> LENGTH: 31
<212> TYPE: DNA
<213> ORGANISM: Artificial
<220> FEATURE:
<223> OTHER INFORMATION: primer

<400> SEQUENCE: 23
cctttgagct cgcgggcagt gagcgcaacg c                                       31

<210> SEQ ID NO 24
<211> LENGTH: 48
<212> TYPE: DNA
<213> ORGANISM: Artificial
<220> FEATURE:
<223> OTHER INFORMATION: primer

<400> SEQUENCE: 24
ctagagcggc cgccgatcgg gatcctcctg tgtgaaattg ttatccgc                     48

<210> SEQ ID NO 25
<211> LENGTH: 42
<212> TYPE: DNA
<213> ORGANISM: Artificial
<220> FEATURE:
<223> OTHER INFORMATION: primer

<400> SEQUENCE: 25
ctctacgatc gaggaggtta taaaaaatgg atattaatac tg                           42

<210> SEQ ID NO 26
<211> LENGTH: 36
<212> TYPE: DNA
<213> ORGANISM: Artificial
<220> FEATURE:
<223> OTHER INFORMATION: primer

<400> SEQUENCE: 26
tcaaagcggc cgcttcttcg tctgtttcta ctggta                                  36

<210> SEQ ID NO 27
<211> LENGTH: 31
<212> TYPE: DNA
<213> ORGANISM: Artificial
<220> FEATURE:
<223> OTHER INFORMATION: primer

```
<400> SEQUENCE: 27
cctttggtac cgcgggcagt gagcgcaacg c                                        31

<210> SEQ ID NO 28
<211> LENGTH: 34
<212> TYPE: DNA
<213> ORGANISM: Artificial
<220> FEATURE:
<223> OTHER INFORMATION: primer

<400> SEQUENCE: 28
aacaggaatt ctttgcctgg cggcagtagc gcgg                                     34

<210> SEQ ID NO 29
<211> LENGTH: 40
<212> TYPE: DNA
<213> ORGANISM: Artificial
<220> FEATURE:
<223> OTHER INFORMATION: primer P1

<400> SEQUENCE: 29
ctagtaagat cttgaagcct gcttttttat actaagttgg                               40

<210> SEQ ID NO 30
<211> LENGTH: 41
<212> TYPE: DNA
<213> ORGANISM: Artificial
<220> FEATURE:
<223> OTHER INFORMATION: primer P2

<400> SEQUENCE: 30
atgatcgaat tcgaaatcaa ataatgattt tattttgact g                             41

<210> SEQ ID NO 31
<211> LENGTH: 120
<212> TYPE: DNA
<213> ORGANISM: Artificial
<220> FEATURE:
<223> OTHER INFORMATION: DNA fragment containing attL

<400> SEQUENCE: 31
agatcttgaa gcctgctttt ttatactaag ttggcattat aaaaaagcat tgcttatcaa         60
tttgttgcaa cgaacaggtc actatcagtc aaaataaaat cattatttga tttcgaattc        120

<210> SEQ ID NO 32
<211> LENGTH: 41
<212> TYPE: DNA
<213> ORGANISM: Artificial
<220> FEATURE:
<223> OTHER INFORMATION: primer P3

<400> SEQUENCE: 32
atgccactgc agtctgttac aggtcactaa taccatctaa g                             41

<210> SEQ ID NO 33
<211> LENGTH: 46
<212> TYPE: DNA
<213> ORGANISM: Artificial
<220> FEATURE:
<223> OTHER INFORMATION: primer P4

<400> SEQUENCE: 33
accgttaagc tttctagacg ctcaagttag tataaaaaag ctgaac                        46
```

```
<210> SEQ ID NO 34
<211> LENGTH: 184
<212> TYPE: DNA
<213> ORGANISM: Artificial
<220> FEATURE:
<223> OTHER INFORMATION: DNA fragment containing attR

<400> SEQUENCE: 34
ctgcagtctg ttacaggtca ctaataccat ctaagtagtt gattcatagt gactgcatat    60
gttgtgtttt acagtattat gtagtctgtt ttttatgcaa aatctaattt aatatattga   120
tatttatatc attttacgtt tctcgttcag cttttttata ctaacttgag cgtctagaaa   180
gctt                                                                 184

<210> SEQ ID NO 35
<211> LENGTH: 38
<212> TYPE: DNA
<213> ORGANISM: Artificial
<220> FEATURE:
<223> OTHER INFORMATION: primer P5

<400> SEQUENCE: 35
ttcttagacg tcaggtggca cttttcgggg aaatgtgc                             38

<210> SEQ ID NO 36
<211> LENGTH: 37
<212> TYPE: DNA
<213> ORGANISM: Artificial
<220> FEATURE:
<223> OTHER INFORMATION: primer P6

<400> SEQUENCE: 36
taacagagat ctcgcgcaga aaaaaggat ctcaaga                               37

<210> SEQ ID NO 37
<211> LENGTH: 46
<212> TYPE: DNA
<213> ORGANISM: Artificial
<220> FEATURE:
<223> OTHER INFORMATION: primer P7

<400> SEQUENCE: 37
aacagagatc taagcttaga tcctttgcct ggcggcagta gcgcgg                    46

<210> SEQ ID NO 38
<211> LENGTH: 35
<212> TYPE: DNA
<213> ORGANISM: Artificial
<220> FEATURE:
<223> OTHER INFORMATION: primer P8

<400> SEQUENCE: 38
ataaactgca gcaaaaagag tttgtagaaa cgcaa                                35

<210> SEQ ID NO 39
<211> LENGTH: 1388
<212> TYPE: DNA
<213> ORGANISM: Artificial
<220> FEATURE:
<223> OTHER INFORMATION: DNA fragment containing Tc gene and ter_thrL

<400> SEQUENCE: 39
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120
cggcaccgtc accctggatg ctgtaggcat aggcttggtt atgccggtac tgccgggcct   180
```

-continued

```
cttgcgggat atcgtccatt ccgacagcat cgccagtcac tatggcgtgc tgctagcgct    240
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcctctacgc cggacgcatc gtggccggca tcaccggcgc    420
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt gcggcggcgg tgctcaacgg    600
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt tcgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
actagaaagc ttaacacaga aaaaagcccg cacctgacag tgcgggcttt ttttttcgac   1380
cactgcag                                                             1388
```

<210> SEQ ID NO 40
<211> LENGTH: 36
<212> TYPE: DNA
<213> ORGANISM: Artificial
<220> FEATURE:
<223> OTHER INFORMATION: primer P9

<400> SEQUENCE: 40
agtaattcta gaaagcttaa cacagaaaaa agcccg                               36

<210> SEQ ID NO 41
<211> LENGTH: 43
<212> TYPE: DNA
<213> ORGANISM: Artificial
<220> FEATURE:
<223> OTHER INFORMATION: primer P10

<400> SEQUENCE: 41
ctagtaggat ccctgcagtg gtcgaaaaaa aaagcccgca ctg                        43

<210> SEQ ID NO 42
<211> LENGTH: 33
<212> TYPE: DNA
<213> ORGANISM: Artificial
<220> FEATURE:
<223> OTHER INFORMATION: primer 1

<400> SEQUENCE: 42
ggaagatcta tttgccttcg cacatcaacc tgg                                   33

```
<210> SEQ ID NO 43
<211> LENGTH: 30
<212> TYPE: DNA
<213> ORGANISM: Artificial
<220> FEATURE:
<223> OTHER INFORMATION: primer 2

<400> SEQUENCE: 43
cggggtacct tgtaaatatt ttaacccgcc                                  30

<210> SEQ ID NO 44
<211> LENGTH: 56
<212> TYPE: DNA
<213> ORGANISM: Artificial
<220> FEATURE:
<223> OTHER INFORMATION: primer 3

<400> SEQUENCE: 44
ggaagatcta aggagacctt aaatgagcga cacaacgatc ctgcaaaaca gtaccc     56

<210> SEQ ID NO 45
<211> LENGTH: 39
<212> TYPE: DNA
<213> ORGANISM: Artificial
<220> FEATURE:
<223> OTHER INFORMATION: primer 4

<400> SEQUENCE: 45
cggggtacct cgtagaggtt tactggcgct tatccagcg                        39

<210> SEQ ID NO 46
<211> LENGTH: 80
<212> TYPE: DNA
<213> ORGANISM: Artificial
<220> FEATURE:
<223> OTHER INFORMATION: primer

<400> SEQUENCE: 46
gcatatgtat gacaccgtca aaggttccga ctacatcggt gaccaggacg tgaagcctgc 60 tttttttatac taagttggca                                            80

<210> SEQ ID NO 47
<211> LENGTH: 80
<212> TYPE: DNA
<213> ORGANISM: Artificial
<220> FEATURE:
<223> OTHER INFORMATION: primer

<400> SEQUENCE: 47
tccagctcaa ggcactcaat acgctgtgta ttgaagtcag gtgagcggtc cgctcaagtt 60
agtataaaaa agctgaacga                                             80

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ccaggcactc gtcctcggtt                                             20

<210> SEQ ID NO 49
<211> LENGTH: 48
<212> TYPE: DNA
<213> ORGANISM: Artificial
```

```
<220> FEATURE:
<223> OTHER INFORMATION: primer

<400> SEQUENCE: 49
aggctagtgc aggactataa agaccagttc tcctaaaaat aacgtgtc                    48

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
tccatcgtgg ccaccgatcc                                                  20

<210> SEQ ID NO 51
<211> LENGTH: 48
<212> TYPE: DNA
<213> ORGANISM: Artificial
<220> FEATURE:
<223> OTHER INFORMATION: primer

<400> SEQUENCE: 51
gacacgttat ttttaggaga actggtcttt atagtcctgc actagcct                   48

<210> SEQ ID NO 52
<211> LENGTH: 25
<212> TYPE: DNA
<213> ORGANISM: Artificial
<220> FEATURE:
<223> OTHER INFORMATION: primer

<400> SEQUENCE: 52
cgggatcccc accggcgtac tcgtg                                            25

<210> SEQ ID NO 53
<211> LENGTH: 28
<212> TYPE: DNA
<213> ORGANISM: Artificial
<220> FEATURE:
<223> OTHER INFORMATION: primer

<400> SEQUENCE: 53
ccacggatcc ttccaatgct attggttg                                         28

<210> SEQ ID NO 54
<211> LENGTH: 28
<212> TYPE: DNA
<213> ORGANISM: Artificial
<220> FEATURE:
<223> OTHER INFORMATION: primer

<400> SEQUENCE: 54
gggagctcga ctttctggct cctttact                                         28

<210> SEQ ID NO 55
<211> LENGTH: 28
<212> TYPE: DNA
<213> ORGANISM: Artificial
<220> FEATURE:
<223> OTHER INFORMATION: primer

<400> SEQUENCE: 55
gggagctcgc cgatgactaa taatgaga                                         28
```

-continued

```
<210> SEQ ID NO 56
<211> LENGTH: 2432
<212> TYPE: DNA
<213> ORGANISM: Corynebacterium glutamicum
<220> FEATURE:
<221> NAME/KEY: CDS
<222> LOCATION: (507)..(2096)

<400> SEQUENCE: 56 agggcggcg  gatcgaccac  ggcttgcaac  cgtggcggga  gtgggctgtt  gagaagctgc      60
cacattcacg  actttctggc  tcctttacta  aataaggatt  ttcacaggac  ccgtccaagc     120
caagccgatt  tcaactcagc  ctaaagacaa  agccctcatt  taaaattgtt  ccgacgcgga     180
tgcgtgtgca  cgcagtgcga  cagatgtctg  ttgcaaagtt  ggctacttgg  gtcataacca     240
acaagaaagc  cctcgttcca  acactgtggt  gagtgttgtc  gagggcgctt  gacgagacga     300
cttggaaggc  cgttacggca  ggcgccgcgc  ggttactact  acaagtcgaa  taatggtcat     360
ggtgtgtcat  gctacacaca  tcgagtttcc  aattccacaa  cgcacgaaaa  ttcccacccc     420
caaaactccc  ccacttcggt  taaggaatca  ggattctcac  aaagttcagg  caggctcccg     480
ctacttttca  gcgctaatct  tggctc atg att tta ggc gta ccc att caa tat         533
                                Met Ile Leu Gly Val Pro Ile Gln Tyr
                                 1               5 ttg ctc tat tca ttg tgg aat tgg att gtc gat acc ggt ttt gat gta             581
Leu Leu Tyr Ser Leu Trp Asn Trp Ile Val Asp Thr Gly Phe Asp Val
 10              15                  20                  25 gca att atc ctg gtc ttg gcg ttt ttg att cca cgt atc ggc cga ctg             629
Ala Ile Ile Leu Val Leu Ala Phe Leu Ile Pro Arg Ile Gly Arg Leu
             30                  35                  40 gcc atg cgt att atc aag cgg cga gtg gag tct gca gcc gat gcg gac             677
Ala Met Arg Ile Ile Lys Arg Arg Val Glu Ser Ala Ala Asp Ala Asp
         45                  50                  55 acc act aag aac cag ctc gcg ttc gct ggc gtt ggc gtt tat atc gcg             725
Thr Thr Lys Asn Gln Leu Ala Phe Ala Gly Val Gly Val Tyr Ile Ala
     60                  65                  70 caa att gtg gcg ttt ttc atg ctt gcc gtc tcc gcg atg cag gct ttt             773
Gln Ile Val Ala Phe Phe Met Leu Ala Val Ser Ala Met Gln Ala Phe
 75                  80                  85 ggt ttc tct ctc gcg ggc gct gcg att ccg gca acc att gcg tca gct             821
Gly Phe Ser Leu Ala Gly Ala Ala Ile Pro Ala Thr Ile Ala Ser Ala
 90                  95                 100                 105 gcc att ggc ctt ggt gcg cag tcg att gtt gcg gac ttc ttg gcc gga             869
Ala Ile Gly Leu Gly Ala Gln Ser Ile Val Ala Asp Phe Leu Ala Gly
                110                 115                 120 ttt ttc atc ctg acg gaa aag caa ttc ggc gtg ggt gac tgg gtg cgt             917
Phe Phe Ile Leu Thr Glu Lys Gln Phe Gly Val Gly Asp Trp Val Arg
            125                 130                 135 ttt gag ggc aac ggc atc gtt gtc gaa ggc acc gtc att gag atc acc             965
Phe Glu Gly Asn Gly Ile Val Val Glu Gly Thr Val Ile Glu Ile Thr
        140                 145                 150 atg cgc gcg acc aaa att cgc acg att gca caa gag acc gtg atc atc            1013
Met Arg Ala Thr Lys Ile Arg Thr Ile Ala Gln Glu Thr Val Ile Ile
    155                 160                 165 ccc aac tcc acg gcg aaa gtg tgc atc aac aat tct aat aac tgg tcg            1061
Pro Asn Ser Thr Ala Lys Val Cys Ile Asn Asn Ser Asn Asn Trp Ser
170                 175                 180                 185 cgt gcg gtt gtc gtt att ccg atc ccc atg ttg ggt tct gaa aac atc            1109
Arg Ala Val Val Val Ile Pro Ile Pro Met Leu Gly Ser Glu Asn Ile
                190                 195                 200 aca gat gtc atc gcg cgc tct gaa gct gcg act cgt cgc gca ctt ggc            1157
Thr Asp Val Ile Ala Arg Ser Glu Ala Ala Thr Arg Arg Ala Leu Gly
```

```
                      205                 210                 215
cag gag aaa atc gca ccg gaa atc ctc ggt gaa ctc gat gtg cac cca      1205
Gln Glu Lys Ile Ala Pro Glu Ile Leu Gly Glu Leu Asp Val His Pro
            220                 225                 230 gcc acg gaa gtc aca ccg cca acg gtg gtc ggc atg ccg tgg atg gtc      1253
Ala Thr Glu Val Thr Pro Pro Thr Val Val Gly Met Pro Trp Met Val
        235                 240                 245 acc atg cgt ttc ctc gtg caa gtc acc gcc ggc aat caa tgg ctg gtc      1301
Thr Met Arg Phe Leu Val Gln Val Thr Ala Gly Asn Gln Trp Leu Val
250                 255                 260                 265 gaa cgc gcc atc cgc aca gaa atc atc aac gaa ttc tgg gaa gaa tac      1349
Glu Arg Ala Ile Arg Thr Glu Ile Ile Asn Glu Phe Trp Glu Glu Tyr
                270                 275                 280 ggc agc gca acc act aca tcg gga acc ctc att gat tcc tta cac gtt      1397
Gly Ser Ala Thr Thr Thr Ser Gly Thr Leu Ile Asp Ser Leu His Val
            285                 290                 295 gag cat gaa gag cca aag acc tcg ctt atc gac gcc tcc ccc cag gct      1445
Glu His Glu Glu Pro Lys Thr Ser Leu Ile Asp Ala Ser Pro Gln Ala
        300                 305                 310 ctt aag gaa ccg aag ccg gag gct gcg gcg acg gtt gca tcg cta gct      1493
Leu Lys Glu Pro Lys Pro Glu Ala Ala Ala Thr Val Ala Ser Leu Ala
315                 320                 325 gca tcg tct aac gac gat gca gac aat gca gac gcc tcg gcg atc aat      1541
Ala Ser Ser Asn Asp Asp Ala Asp Asn Ala Asp Ala Ser Ala Ile Asn
330                 335                 340                 345 gca ggc aat cca gag aag gaa ctt gat tcc gat gtg ctg gaa caa gaa      1589
Ala Gly Asn Pro Glu Lys Glu Leu Asp Ser Asp Val Leu Glu Gln Glu
                350                 355                 360 ctc tcc agc gaa gaa ccg gaa gaa aca gca aaa cca gat cac tct ctc      1637
Leu Ser Ser Glu Glu Pro Glu Glu Thr Ala Lys Pro Asp His Ser Leu
            365                 370                 375 cga ggc ttc ttc cgc act gat tac tac cca aat cgg tgg cag aag atc      1685
Arg Gly Phe Phe Arg Thr Asp Tyr Tyr Pro Asn Arg Trp Gln Lys Ile
        380                 385                 390 ctg tcg ttt ggc gga cgt gtc cgc atg agc act tcc ctg ttg ttg ggt      1733
Leu Ser Phe Gly Gly Arg Val Arg Met Ser Thr Ser Leu Leu Leu Gly
395                 400                 405 gcg ctg ctc ttg ctg tca cta ttt aag gtc atg act gtg gaa cca agt      1781
Ala Leu Leu Leu Leu Ser Leu Phe Lys Val Met Thr Val Glu Pro Ser
410                 415                 420                 425 gag aat tgg caa aac tcc agt gga tgg ctg tca cca agc act gcc acc      1829
Glu Asn Trp Gln Asn Ser Ser Gly Trp Leu Ser Pro Ser Thr Ala Thr
                430                 435                 440 tca act gcg gtg acc acc tcc gaa act tcc gcg cca gta agc act tct      1877
Ser Thr Ala Val Thr Thr Ser Glu Thr Ser Ala Pro Val Ser Thr Ser
            445                 450                 455 tcg atg aca gtg ccc act acg gtg gag gag acc cca acg atg gaa tct      1925
Ser Met Thr Val Pro Thr Thr Val Glu Glu Thr Pro Thr Met Glu Ser
        460                 465                 470 agc gtc gaa acg cag cag gaa acc tca acc cct gca acc gca acg ccc      1973
Ser Val Glu Thr Gln Gln Glu Thr Ser Thr Pro Ala Thr Ala Thr Pro
475                 480                 485 cag cga gcc gac acc atc gaa ccg acc gag gaa gcc acg tcg cag gag      2021
Gln Arg Ala Asp Thr Ile Glu Pro Thr Glu Glu Ala Thr Ser Gln Glu
490                 495                 500                 505 gaa acg act gcg tcg cag acg cag tct cca gca acc gcg gtt caa gag      2069
Glu Thr Thr Ala Ser Gln Thr Gln Ser Pro Ala Thr Ala Val Gln Glu
                510                 515                 520 aca gtt gcg ccg acg tcc acc cct tag gacgctgatt acagacgtgt            2116
Thr Val Ala Pro Thr Ser Thr Pro
```

-continued

```
                                                                    525
cccatttctt tactactatt ggaaattatg agttcagacg cagaaaaggc atccgtggag   2176
ctttccgaaa aatttcaccc agaacgcacc catattttgg gcgccgttgt ttttggcctg   2236
atctcattat tagtcatcgg cgcagcccct cagtacctgt tttggctgct cgcgctccct   2296
gtcatcttcg gttactgggt tctaaaatca tccacgatcg ttgatgaaca gggcatcacc   2356
gcaaactacg ccttcaaggg caaaaaggtt gtggcctggg aagacctcgc aggaatcgga   2416
ttcaagggtg cccgca                                                   2432

<210> SEQ ID NO 57
<211> LENGTH: 529
<212> TYPE: PRT
<213> ORGANISM: Corynebacterium glutamicum

<400> SEQUENCE: 57

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
```

```
                305                 310                 315                 320
Ala Ala Ala Thr Val Ala Ser Leu Ala Ala Ser Ser Asn Asp Asp Ala
                    325                 330                 335

Asp Asn Ala Asp Ala Ser Ala Ile Asn Ala Gly Asn Pro Glu Lys Glu
                340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
        370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                    405                 410                 415

Phe Lys Val Met Thr Val Glu Pro Ser Glu Asn Trp Gln Asn Ser Ser
                420                 425                 430

Gly Trp Leu Ser Pro Ser Thr Ala Thr Ser Thr Ala Val Thr Thr Ser
            435                 440                 445

Glu Thr Ser Ala Pro Val Ser Thr Ser Ser Met Thr Val Pro Thr Thr
        450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                    485                 490                 495

Pro Thr Glu Glu Ala Thr Ser Gln Glu Glu Thr Thr Ala Ser Gln Thr
                500                 505                 510

Gln Ser Pro Ala Thr Ala Val Gln Glu Thr Val Ala Pro Thr Ser Thr
            515                 520                 525

Pro

<210> SEQ ID NO 58
<211> LENGTH: 2432
<212> TYPE: DNA
<213> ORGANISM: Corynebacterium glutamicum
<220> FEATURE:
<221> NAME/KEY: CDS
<222> LOCATION: (507)..(2096)

<400> SEQUENCE: 58 agggggcggcg gatcgaccac ggcttgcaac cgtggcggga gtgggctgtt gagaagctgc     60
cacattcacg actttctggc tcctttacta aataaggatt ttcacaggac ccgtccaagc    120
caagccgatt tcaactcagc ctaaagacaa agccctcatt taaaattgtt ccgacgcgga    180
tgcgtgtgca cgcagtgcga cagatgtctg ttgcaaagtt ggctacttgg gtcataacca    240
acaagaaagc cctcgttcca cactgtggt gagtgttgtc gagggcgctt gacgagacga     300
cttggaaggc cgttacggca ggcgccgcgc ggttactact acaagtcgaa taatggtcat    360
ggtgtgtcat gctacacaca tcgagtttcc aattccacaa cgcacgaaaa ttcccacccc    420
caaaactccc ccactccggt taaggaatca ggattctcac aaagttcagg caggctcccg    480
``` ctactttca gcgctaatct tggctc atg att tta ggc gta ccc att caa tat       533
                              Met Ile Leu Gly Val Pro Ile Gln Tyr
                               1               5 ttg ctc tat tca ttg tgg aat tgg att gtc gat acc ggt ttt gat gta       581
Leu Leu Tyr Ser Leu Trp Asn Trp Ile Val Asp Thr Gly Phe Asp Val
 10              15                  20                  25 gca att atc ctg gtc ttg gcg ttt ttg att cca cgt atc ggc cga ctg       629
Ala Ile Ile Leu Val Leu Ala Phe Leu Ile Pro Arg Ile Gly Arg Leu

```
                     30                  35                  40
gcc atg cgt att atc aag cgg cga gtg gag tct gca gcc gat gcg gac        677
Ala Met Arg Ile Ile Lys Arg Arg Val Glu Ser Ala Ala Asp Ala Asp
         45                  50                  55 acc act aag aac cag ctc gcg ttc gct ggc gtt ggc gtt tat atc gcg        725
Thr Thr Lys Asn Gln Leu Ala Phe Ala Gly Val Gly Val Tyr Ile Ala
     60                  65                  70 caa att gtg gcg ttt ttc atg ctt gcc gtc tcc gcg atg cag gct ttt        773
Gln Ile Val Ala Phe Phe Met Leu Ala Val Ser Ala Met Gln Ala Phe
 75                  80                  85 ggt ttc tct ctc gcg ggc gct gcg att ccg gca acc att gcg tca gct        821
Gly Phe Ser Leu Ala Gly Ala Ala Ile Pro Ala Thr Ile Ala Ser Ala
 90                  95                 100                 105 gcc att ggc ctt ggt gcg cag tcg att gtt gcg gac ttc ttg gcc gga        869
Ala Ile Gly Leu Gly Ala Gln Ser Ile Val Ala Asp Phe Leu Ala Gly
                    110                 115                 120 ttt ttc atc ctg acg gaa aag caa ttc ggc gtg ggt gac tgg gtg cgt        917
Phe Phe Ile Leu Thr Glu Lys Gln Phe Gly Val Gly Asp Trp Val Arg
                125                 130                 135 ttt gag ggc aac ggc atc gtt gtc gaa ggc acc gtc att gag atc acc        965
Phe Glu Gly Asn Gly Ile Val Val Glu Gly Thr Val Ile Glu Ile Thr
            140                 145                 150 atg cgc gcg acc aaa att cgc acg att gca caa gag acc gtg atc atc       1013
Met Arg Ala Thr Lys Ile Arg Thr Ile Ala Gln Glu Thr Val Ile Ile
        155                 160                 165 ccc aac tcc acg gcg aaa gtg tgc atc aac aat tct aat aac tgg tcg       1061
Pro Asn Ser Thr Ala Lys Val Cys Ile Asn Asn Ser Asn Asn Trp Ser
170                 175                 180                 185 cgt gcg gtt gtc gtt att ccg atc ccc atg ttg ggt tct gaa aac atc       1109
Arg Ala Val Val Val Ile Pro Ile Pro Met Leu Gly Ser Glu Asn Ile
                190                 195                 200 aca gat gtc atc gcg cgc tct gaa gct gcg act cgt cgc gca ctt ggc       1157
Thr Asp Val Ile Ala Arg Ser Glu Ala Ala Thr Arg Arg Ala Leu Gly
            205                 210                 215 cag gag aaa atc gca ccg gaa atc ctc ggt gaa ctc gat gtg cac cca       1205
Gln Glu Lys Ile Ala Pro Glu Ile Leu Gly Glu Leu Asp Val His Pro
        220                 225                 230 gcc acg gaa gtc aca ccg cca acg gtg gtc ggc atg ccg tgg atg gtc       1253
Ala Thr Glu Val Thr Pro Pro Thr Val Val Gly Met Pro Trp Met Val
    235                 240                 245 acc atg cgt ttc ctc gtg caa gtc acc gcc ggc aat caa tgg ctg gtc       1301
Thr Met Arg Phe Leu Val Gln Val Thr Ala Gly Asn Gln Trp Leu Val
250                 255                 260                 265 gaa cgc gcc atc cgc aca gaa atc atc aac gaa ttc tgg gaa gaa tac       1349
Glu Arg Ala Ile Arg Thr Glu Ile Ile Asn Glu Phe Trp Glu Glu Tyr
                270                 275                 280 ggc agc gca acc act aca tcg gga acc ctc att gat tcc tta cac gtt       1397
Gly Ser Ala Thr Thr Thr Ser Gly Thr Leu Ile Asp Ser Leu His Val
            285                 290                 295 gag cat gaa gag cca aag acc tcg ctt atc gac gcc tcc ccc cag gct       1445
Glu His Glu Glu Pro Lys Thr Ser Leu Ile Asp Ala Ser Pro Gln Ala
        300                 305                 310 ctt aag gaa ccg aag ccg gag gct gcg gcg acg gtt gca tcg cta gct       1493
Leu Lys Glu Pro Lys Pro Glu Ala Ala Ala Thr Val Ala Ser Leu Ala
    315                 320                 325 gca tcg tct aac gac gat gca gac aat gca gac gcc tcg gcg atc aat       1541
Ala Ser Ser Asn Asp Asp Ala Asp Asn Ala Asp Ala Ser Ala Ile Asn
330                 335                 340                 345 gca ggc aat cca gag aag gaa ctt gat tcc gat gtg ctg gaa caa gaa       1589
Ala Gly Asn Pro Glu Lys Glu Leu Asp Ser Asp Val Leu Glu Gln Glu
```

```
                    350                 355                 360
ctc tcc agc gaa gaa ccg gaa gaa aca gca aaa cca gat cac tct ctc       1637
Leu Ser Ser Glu Glu Pro Glu Glu Thr Ala Lys Pro Asp His Ser Leu
        365                 370                 375 cga ggc ttc ttc cgc act gat tac tac cca aat cgg tgg cag aag atc       1685
Arg Gly Phe Phe Arg Thr Asp Tyr Tyr Pro Asn Arg Trp Gln Lys Ile
                380                 385                 390 ctg tcg ttt ggc gga cgt gtc cgc atg agc act tcc ctg ttg ttg ggt       1733
Leu Ser Phe Gly Gly Arg Val Arg Met Ser Thr Ser Leu Leu Leu Gly
395                 400                 405 gcg ctc ctc ttg ctg tca cta ttt aag gtc atg act gtg gaa cca agt       1781
Ala Leu Leu Leu Leu Ser Leu Phe Lys Val Met Thr Val Glu Pro Ser
410                 415                 420                 425 gag aat tgg caa aac tcc agt gga tgg ctg tca cca agc act gcc acc       1829
Glu Asn Trp Gln Asn Ser Ser Gly Trp Leu Ser Pro Ser Thr Ala Thr
                430                 435                 440 tca act gcg gtg acc acc tcc gaa act tcc gcg cca gta agc act tct       1877
Ser Thr Ala Val Thr Thr Ser Glu Thr Ser Ala Pro Val Ser Thr Ser
                445                 450                 455 tcg atg aca gtg ccc act acg gtg gag gag acc cca acg atg gaa tct       1925
Ser Met Thr Val Pro Thr Thr Val Glu Glu Thr Pro Thr Met Glu Ser
460                 465                 470 agc gtc gaa acg cag cag gaa acc tca acc cct gca acc gca acg ccc       1973
Ser Val Glu Thr Gln Gln Glu Thr Ser Thr Pro Ala Thr Ala Thr Pro
475                 480                 485 cag cga gcc gac acc atc gaa ccg acc gag gaa gcc acg tcg cag gag       2021
Gln Arg Ala Asp Thr Ile Glu Pro Thr Glu Glu Ala Thr Ser Gln Glu
490                 495                 500                 505 gaa acg act gcg tcg cag acg cag tct cca gca acc gcg gtt caa gag       2069
Glu Thr Thr Ala Ser Gln Thr Gln Ser Pro Ala Thr Ala Val Gln Glu
                510                 515                 520 aca gtt gcg ccg acg tcc acc cct tag gacgctgatt acagacgtgt             2116
Thr Val Ala Pro Thr Ser Thr Pro
                525 cccatttctt tactactatt ggaaattatg agttcagacg cagaaaaggc atccgtggag     2176 ctttccgaaa aatttcaccc agaacgcacc catattttgg gcgccgttgt ttttggcctg     2236 atctcattat tagtcatcgg cgcagcccct cagtacctgt tttggctgct cgcgctccct     2296 gtcatcttcg gttactgggt tctaaaatca tccacgatcg ttgatgaaca gggcatcacc     2356 gcaaactacg ccttcagggg caaaaaggtt gtggcctggg aagacctcgc aggaatcgga     2416 ttcaagggtg cccgca                                                    2432

<210> SEQ ID NO 59
<211> LENGTH: 529
<212> TYPE: PRT
<213> ORGANISM: Corynebacterium glutamicum

<400> SEQUENCE: 59

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80
```

```
Leu Ala Val Ser Ala Met Gln Ala Phe Gly Phe Ser Leu Ala Gly Ala
                 85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
            115                 120                 125

Gln Phe Gly Val Gly Asp Trp Val Arg Phe Glu Gly Asn Gly Ile Val
            130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
            165                 170                 175

Cys Ile Asn Asn Ser Asn Asn Trp Ser Arg Ala Val Val Val Ile Pro
            180                 185                 190

Ile Pro Met Leu Gly Ser Glu Asn Ile Thr Asp Val Ile Ala Arg Ser
            195                 200                 205

Glu Ala Ala Thr Arg Arg Ala Leu Gly Gln Glu Lys Ile Ala Pro Glu
            210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
            245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
            325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
            370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
            405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
            435                 440                 445

Glu Thr Ser Ala Pro Val Ser Thr Ser Ser Met Thr Val Pro Thr Thr
            450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
            485                 490                 495

Pro Thr Glu Glu Ala Thr Ser Gln Glu Glu Thr Thr Ala Ser Gln Thr
```

-continued

```
              500              505              510
Gln Ser Pro Ala Thr Ala Val Gln Glu Thr Val Ala Pro Thr Ser Thr
        515              520              525
Pro

<210> SEQ ID NO 60
<211> LENGTH: 22
<212> TYPE: DNA
<213> ORGANISM: Artificial
<220> FEATURE:
<223> OTHER INFORMATION: primer

<400> SEQUENCE: 60
cagttgtggc tgatcgccaa gg                                            22

<210> SEQ ID NO 61
<211> LENGTH: 52
<212> TYPE: DNA
<213> ORGANISM: Artificial
<220> FEATURE:
<223> OTHER INFORMATION: primer

<400> SEQUENCE: 61
tcaattatag cagtgtcgca cagatatggc cacaaagaat taaaattgtt tg           52

<210> SEQ ID NO 62
<211> LENGTH: 23
<212> TYPE: DNA
<213> ORGANISM: Artificial
<220> FEATURE:
<223> OTHER INFORMATION: primer

<400> SEQUENCE: 62
ccatgcgacg gtagtggcca aac                                           23

<210> SEQ ID NO 63
<211> LENGTH: 52
<212> TYPE: DNA
<213> ORGANISM: Artificial
<220> FEATURE:
<223> OTHER INFORMATION: primer

<400> SEQUENCE: 63
ttgtggccat atctgtgcga cactgctata attgaacgtg agcatttacc ag           52

<210> SEQ ID NO 64
<211> LENGTH: 31
<212> TYPE: DNA
<213> ORGANISM: Artificial
<220> FEATURE:
<223> OTHER INFORMATION: primer

<400> SEQUENCE: 64
cgccccgggt gaccgcgtct gcgatcaaaa c                                  31

<210> SEQ ID NO 65
<211> LENGTH: 28
<212> TYPE: DNA
<213> ORGANISM: Artificial
<220> FEATURE:
<223> OTHER INFORMATION: primer

<400> SEQUENCE: 65
cgatcccggg gccaccaact ccgatgtc                                      28
```

```
<210> SEQ ID NO 66
<211> LENGTH: 440
<212> TYPE: DNA
<213> ORGANISM: Artificial
<220> FEATURE:
<223> OTHER INFORMATION: mutant promoter of gdh

<400> SEQUENCE: 66
cgaaaaggtc ggaaagtgcc cgaatgtgcg ttgttctagc tagcctcggg agctccagga      60
gattgtgaaa aacggctcaa atttctccga tgtagcgcct ataaaagtcg caccaattcc     120
atttgagggc gctcaagtgt ggccaggtta tataaccagt cagtcaactg gtctcattcg     180
ctggtcggat gaatttaatt aaagaagaga cttcatgcag ttaccgcgcg ttttggcgat     240
acaaaattga taaacctaaa gaattttca aacaattta attctttgtg gccatatctg      300
tgcgacactg ctataattga acgtgagcat ttaccagcct aaatgtccgc agtgagttaa     360
gtctcaaagc aagaagttgc tctttagggc atccgtagtt taaaactatt aaccgttagg    420
tatgacaagc cggttgatgt                                                440

<210> SEQ ID NO 67
<211> LENGTH: 20
<212> TYPE: DNA
<213> ORGANISM: Artificial
<220> FEATURE:
<223> OTHER INFORMATION: primer

<400> SEQUENCE: 67
tcctcccaca cggctcagtc                                                 20

<210> SEQ ID NO 68
<211> LENGTH: 42
<212> TYPE: DNA
<213> ORGANISM: Artificial
<220> FEATURE:
<223> OTHER INFORMATION: primer

<400> SEQUENCE: 68
tacttgtagt tccttgtctg aaattcttcc taacctttac gc                        42

<210> SEQ ID NO 69
<211> LENGTH: 20
<212> TYPE: DNA
<213> ORGANISM: Artificial
<220> FEATURE:
<223> OTHER INFORMATION: primer

<400> SEQUENCE: 69
ggcagcgaca catgcaccac                                                 20

<210> SEQ ID NO 70
<211> LENGTH: 42
<212> TYPE: DNA
<213> ORGANISM: Artificial
<220> FEATURE:
<223> OTHER INFORMATION: primer

<400> SEQUENCE: 70
gcgtaaaggt taggaagaat ttcagacaag gaactacaag ta                        42

<210> SEQ ID NO 71
<211> LENGTH: 25
<212> TYPE: DNA
<213> ORGANISM: Artificial
<220> FEATURE:
<223> OTHER INFORMATION: primer
```

<400> SEQUENCE: 71
ctggatccta cgtattatcc tgctg                                                         25

<210> SEQ ID NO 72
<211> LENGTH: 24
<212> TYPE: DNA
<213> ORGANISM: Artificial
<220> FEATURE:
<223> OTHER INFORMATION: primer

<400> SEQUENCE: 72
gcggatccag gctgcgtggt caag                                                          24

<210> SEQ ID NO 73
<211> LENGTH: 4200
<212> TYPE: DNA
<213> ORGANISM: Corynebacterium glutamicum
<220> FEATURE:
<221> NAME/KEY: CDS
<222> LOCATION: (449)..(1219)
<220> FEATURE:
<221> NAME/KEY: CDS
<222> LOCATION: (1239)..(3257)
<220> FEATURE:
<221> NAME/KEY: CDS
<222> LOCATION: (3260)..(4006)

<400> SEQUENCE: 73
aggtgttgca aacttgttga ttttcgcttt tcgacgcagc ccgccgccac caggtgcccg      60
gcgtggtcgg gccacatccg ccccgggaac tttttaggca cctacggtgc aactgttggg     120
ataattgtgt cacctgcgca aagttgctcc ctggatcgga aggttgggct gtctaaactt     180
tttggttgat accaaacggg gttagaaact gttcggatcg gtatcctgtg aggaagctca     240
ccttggtttt agaatgttga aaaggcctca cgtttccgca ggtagagcac actcaattaa     300
atgagcgtca aacgacaata aagtaaggct atcctaataa gtggggtttt atgtctctaa     360
acagccagtt gggggtcatg ggggagcgcc ccgtgactgg ttaatgcccc gatctgggac     420
gtacagtaac aacgacactg gaggtgcc atg act gtt aga aat ccc gac cgt          472
                                Met Thr Val Arg Asn Pro Asp Arg
                                 1               5 gag gca atc cgt cac gga aaa att acg acg gag gcg ctg cgt gag cgt         520
Glu Ala Ile Arg His Gly Lys Ile Thr Thr Glu Ala Leu Arg Glu Arg
        10                  15                  20 ccc gca tac ccg acc tgg gca atg aag ctg acc atg gcc atc act ggc         568
Pro Ala Tyr Pro Thr Trp Ala Met Lys Leu Thr Met Ala Ile Thr Gly
 25                  30                  35                  40 cta atg ttt ggt ggc ttc gtt ctt gtt cac atg atc gga aac ctg aaa         616
Leu Met Phe Gly Gly Phe Val Leu Val His Met Ile Gly Asn Leu Lys
                 45                  50                  55 atc ttc atg ccg gac tac gca gcc gat tct gcg cat ccg ggt gaa gca         664
Ile Phe Met Pro Asp Tyr Ala Ala Asp Ser Ala His Pro Gly Glu Ala
             60                  65                  70 caa gta gat gtc tac ggc gag ttc ctg cgt gag atc gga tcc ccg atc         712
Gln Val Asp Val Tyr Gly Glu Phe Leu Arg Glu Ile Gly Ser Pro Ile
         75                  80                  85 ctc cca cac ggc tca gtc ctc tgg atc cta cgt att atc ctg ctg gtc         760
Leu Pro His Gly Ser Val Leu Trp Ile Leu Arg Ile Ile Leu Leu Val
     90                  95                 100 gca ttg gtt ctg cac atc tac tgt gca ttc gca ttg acc ggc cgt tct         808
Ala Leu Val Leu His Ile Tyr Cys Ala Phe Ala Leu Thr Gly Arg Ser
105                 110                 115                 120

```
cac cag tcc cgc gga aag ttc cgc cgt acc aac ctc gtt ggc ggc ttc      856
His Gln Ser Arg Gly Lys Phe Arg Arg Thr Asn Leu Val Gly Gly Phe
            125                 130                 135 aac tcc ttc gcg acc cgc tcc atg ctg gtg acc gga atc gtt ctc ctt      904
Asn Ser Phe Ala Thr Arg Ser Met Leu Val Thr Gly Ile Val Leu Leu
        140                 145                 150 gcg ttc att atc ttc cac atc ctc gac ctg acc atg ggt gtt gct cca      952
Ala Phe Ile Ile Phe His Ile Leu Asp Leu Thr Met Gly Val Ala Pro
    155                 160                 165 gca gcc cca acc tca ttc gag cac ggc gaa gta tac gca aac atg gtg     1000
Ala Ala Pro Thr Ser Phe Glu His Gly Glu Val Tyr Ala Asn Met Val
170                 175                 180 gct tcc ttt agc cgc tgg cct gta gca att tgg tac atc att gcc aac     1048
Ala Ser Phe Ser Arg Trp Pro Val Ala Ile Trp Tyr Ile Ile Ala Asn
185                 190                 195                 200 ctg gtc ctg ttc gtc cac ctg tca cac ggc atc tgg ctt gca gtc tct     1096
Leu Val Leu Phe Val His Leu Ser His Gly Ile Trp Leu Ala Val Ser
                205                 210                 215 gac ctg gga atc acc gga cgc cgc tgg agg gca atc ctc ctc gca gtt     1144
Asp Leu Gly Ile Thr Gly Arg Arg Trp Arg Ala Ile Leu Leu Ala Val
            220                 225                 230 gcg tac atc gtt cct gca ctg gtc ctg atc ggc aac atc acc att ccg     1192
Ala Tyr Ile Val Pro Ala Leu Val Leu Ile Gly Asn Ile Thr Ile Pro
        235                 240                 245 ttc gcc atc gct gtt ggc tgg att gcg taaaggttag gaagaattt atg agc    1244
Phe Ala Ile Ala Val Gly Trp Ile Ala                         Met Ser
    250                 255 act cac tct gaa acc acc cgc cca gag ttc atc cac cca gtc tca gtc     1292
Thr His Ser Glu Thr Thr Arg Pro Glu Phe Ile His Pro Val Ser Val
260                 265                 270                 275 ctc cca gag gtc tca gct ggt acg gtc ctt gac gct gca gag cca gca     1340
Leu Pro Glu Val Ser Ala Gly Thr Val Leu Asp Ala Ala Glu Pro Ala
                280                 285                 290 ggc gtt ccc acc aaa gat atg tgg gaa tac caa aaa gac cac atg aac     1388
Gly Val Pro Thr Lys Asp Met Trp Glu Tyr Gln Lys Asp His Met Asn
            295                 300                 305 ctg gtc tcc cca ctg aac cga cgc aag ttc cgt gtc ctc gtc gtt ggc     1436
Leu Val Ser Pro Leu Asn Arg Arg Lys Phe Arg Val Leu Val Val Gly
        310                 315                 320 acc ggc ctg tcc ggt ggt gct gca gca gcc ctc ggc gaa ctc gga         1484
Thr Gly Leu Ser Gly Gly Ala Ala Ala Ala Leu Gly Glu Leu Gly
    325                 330                 335 tac gac gtc aag gcg ttc acc tac cac gac gca cct cgc cgt gcg cac     1532
Tyr Asp Val Lys Ala Phe Thr Tyr His Asp Ala Pro Arg Arg Ala His
340                 345                 350                 355 tcc att gct gca cag ggt ggc gtt aac tcc gcc cgc ggc aag aag gta     1580
Ser Ile Ala Ala Gln Gly Gly Val Asn Ser Ala Arg Gly Lys Lys Val
                360                 365                 370 gac aac gac ggc gca tac cgc cac gtc aag gac acc gtc aag ggc ggc     1628
Asp Asn Asp Gly Ala Tyr Arg His Val Lys Asp Thr Val Lys Gly Gly
            375                 380                 385 gac tac cgt ggt cgc gag tcc gac tgc tgg cgt ctc gcc gtc gag tcc     1676
Asp Tyr Arg Gly Arg Glu Ser Asp Cys Trp Arg Leu Ala Val Glu Ser
        390                 395                 400 gtc cgc gtc atc gac cac atg aac gcc atc ggt gca cca ttc gcc cgc     1724
Val Arg Val Ile Asp His Met Asn Ala Ile Gly Ala Pro Phe Ala Arg
    405                 410                 415 gaa tac ggt ggc gcc ttg gca acc cgt tcc ttc ggt ggt gtg cag gtc     1772
Glu Tyr Gly Gly Ala Leu Ala Thr Arg Ser Phe Gly Gly Val Gln Val
420                 425                 430                 435
```

```
                                                             -continued
tcc cgt acc tac tac acc cgt gga caa acc gga cag cag ctg cag ctc   1820
Ser Arg Thr Tyr Tyr Thr Arg Gly Gln Thr Gly Gln Gln Leu Gln Leu
            440                 445                 450 tcc acc gca tcc gca cta cag cgc cag atc cac ctc ggc tcc gta gaa   1868
Ser Thr Ala Ser Ala Leu Gln Arg Gln Ile His Leu Gly Ser Val Glu
        455                 460                 465 atc ttc acc cat aac gaa atg gtt gac gtc att gtc acc gaa cgt aac   1916
Ile Phe Thr His Asn Glu Met Val Asp Val Ile Val Thr Glu Arg Asn
    470                 475                 480 ggt gaa aag cgc tgc gaa ggc ctg atc atg cgc aac ctg atc acc ggc   1964
Gly Glu Lys Arg Cys Glu Gly Leu Ile Met Arg Asn Leu Ile Thr Gly
485                 490                 495 gag ctc acc gca cac acc ggc cat gcc gtt atc ctg gca acc ggt ggc   2012
Glu Leu Thr Ala His Thr Gly His Ala Val Ile Leu Ala Thr Gly Gly
500                 505                 510                 515 tac ggc aac gtg tac cac atg tcc acc ctg gcc aag aac tcc aac gcc   2060
Tyr Gly Asn Val Tyr His Met Ser Thr Leu Ala Lys Asn Ser Asn Ala
            520                 525                 530 tcg gcc atc atg cgt gca tac gaa gcc ggc gca tac ttc gcg tcc cca   2108
Ser Ala Ile Met Arg Ala Tyr Glu Ala Gly Ala Tyr Phe Ala Ser Pro
        535                 540                 545 tcg ttc atc cag ttc cac cca acc ggc ctg cct gtg aac tcc acc tgg   2156
Ser Phe Ile Gln Phe His Pro Thr Gly Leu Pro Val Asn Ser Thr Trp
    550                 555                 560 cag tcc aag acc att ctg atg tcc gag tcg ctg cgt aac gac ggc cgc   2204
Gln Ser Lys Thr Ile Leu Met Ser Glu Ser Leu Arg Asn Asp Gly Arg
565                 570                 575 atc tgg tcc cct aag gaa ccg aac gat aac cgc gat cca aac acc atc   2252
Ile Trp Ser Pro Lys Glu Pro Asn Asp Asn Arg Asp Pro Asn Thr Ile
580                 585                 590                 595 cct gag gat gag cgc gac tac ttc ctg gag cgc cgc tac cca gca ttc   2300
Pro Glu Asp Glu Arg Asp Tyr Phe Leu Glu Arg Arg Tyr Pro Ala Phe
            600                 605                 610 ggt aac ctc gtc cca cgt gac gtt gct tcc cgt gcg atc tcc cag cag   2348
Gly Asn Leu Val Pro Arg Asp Val Ala Ser Arg Ala Ile Ser Gln Gln
        615                 620                 625 atc aat gct ggt ctc ggt gtt gga cct ctg aac aac gct gca tac ctg   2396
Ile Asn Ala Gly Leu Gly Val Gly Pro Leu Asn Asn Ala Ala Tyr Leu
    630                 635                 640 gac ttc cgc gac gcc acc gag cgc ctc gga cag gac acc atc cgc gag   2444
Asp Phe Arg Asp Ala Thr Glu Arg Leu Gly Gln Asp Thr Ile Arg Glu
645                 650                 655 cgt tac tcc aac ctc ttc acc atg tac gaa gag gca att ggc gag gac   2492
Arg Tyr Ser Asn Leu Phe Thr Met Tyr Glu Glu Ala Ile Gly Glu Asp
660                 665                 670                 675 cca tac tcc agc cca atg cgt att gca ccg acc tgc cac ttc acc atg   2540
Pro Tyr Ser Ser Pro Met Arg Ile Ala Pro Thr Cys His Phe Thr Met
            680                 685                 690 ggt ggc ctc tgg act gac ttc aac gaa atg acg tca ctc cca ggt ctg   2588
Gly Gly Leu Trp Thr Asp Phe Asn Glu Met Thr Ser Leu Pro Gly Leu
        695                 700                 705 ttc tgc gca ggc gaa gca tcc tgg acc tac cac ggt gca aac cgt ctg   2636
Phe Cys Ala Gly Glu Ala Ser Trp Thr Tyr His Gly Ala Asn Arg Leu
    710                 715                 720 ggc gca aac tcc ctg ctc tcc gct tcc gtc gat ggc tgg ttc acc ctg   2684
Gly Ala Asn Ser Leu Leu Ser Ala Ser Val Asp Gly Trp Phe Thr Leu
725                 730                 735 cca ttc acc atc cct aac tac ctc ggc cca ttg ctt ggc tcc gag cgt   2732
Pro Phe Thr Ile Pro Asn Tyr Leu Gly Pro Leu Leu Gly Ser Glu Arg
            740                 745                 750                 755
```

-continued

| | |
|---|---|
| ctg tca gag gat gca cca gaa gca cag gca gcg att gcg cgt gca cag<br>Leu Ser Glu Asp Ala Pro Glu Ala Gln Ala Ala Ile Ala Arg Ala Gln<br>                   760                              765                           770 | 2780 |
| gct cgc att gac cgc ctc atg ggc aac cgc cca gag tgg gtc ggt gac<br>Ala Arg Ile Asp Arg Leu Met Gly Asn Arg Pro Glu Trp Val Gly Asp<br>                775                             780                           785 | 2828 |
| aac gtt cac gga cct gag tac tac cac cgc cag ctt ggc gat atc ctg<br>Asn Val His Gly Pro Glu Tyr Tyr His Arg Gln Leu Gly Asp Ile Leu<br>              790                             795                           800 | 2876 |
| tac ttc tcc tgt ggc gtt tcc cga aac gta gaa gac ctc cag gat ggc<br>Tyr Phe Ser Cys Gly Val Ser Arg Asn Val Glu Asp Leu Gln Asp Gly<br>     805                       810                         815 | 2924 |
| atc aac aag atc cgt gcc ctc cgc gat gac ttc tgg aag aac atg cgc<br>Ile Asn Lys Ile Arg Ala Leu Arg Asp Asp Phe Trp Lys Asn Met Arg<br>820                     825                         830                        835 | 2972 |
| atc acc ggc agc acc gat gag atg aac cag gtt ctc gaa tac gca gca<br>Ile Thr Gly Ser Thr Asp Glu Met Asn Gln Val Leu Glu Tyr Ala Ala<br>                            840                         845                          850 | 3020 |
| cgc gta gcc gac tac atc gac ctc ggc gaa ctc atg tgt gtc gac gcc<br>Arg Val Ala Asp Tyr Ile Asp Leu Gly Glu Leu Met Cys Val Asp Ala<br>                  855                         860                        865 | 3068 |
| ctc gac cgc gac gag tcc tgt ggc gct cac ttc cgc gac gac cac ctc<br>Leu Asp Arg Asp Glu Ser Cys Gly Ala His Phe Arg Asp Asp His Leu<br>              870                             875                           880 | 3116 |
| tcc gaa gat ggc gaa gca gaa cgt gac gac gaa aac tgg tgc ttc gtc<br>Ser Glu Asp Gly Glu Ala Glu Arg Asp Asp Glu Asn Trp Cys Phe Val<br>     885                       890                         895 | 3164 |
| tcc gca tgg gaa cca ggc gag aac gga acc ttc gtc cgc cac gca gaa<br>Ser Ala Trp Glu Pro Gly Glu Asn Gly Thr Phe Val Arg His Ala Glu<br>900                     905                         910                        915 | 3212 |
| cca ctg ttc ttc gaa tcc gtc cca ctg cag aca agg aac tac aag ta<br>Pro Leu Phe Phe Glu Ser Val Pro Leu Gln Thr Arg Asn Tyr Lys<br>                    920                         925                      930 | 3259 |
| atg aaa ctt aca ctt gag atc tgg cgt caa gca ggc cca act gcg gaa<br>Met Lys Leu Thr Leu Glu Ile Trp Arg Gln Ala Gly Pro Thr Ala Glu<br>                            935                         940                        945 | 3307 |
| ggc aag ttc gaa acc gtc cag gtt gac gac gcc gtc gcg cag atg tcc<br>Gly Lys Phe Glu Thr Val Gln Val Asp Asp Ala Val Ala Gln Met Ser<br>                  950                         955                        960 | 3355 |
| atc ctg gag ctg ctt gac cac gta aac aac aag ttc atc gaa gaa ggc<br>Ile Leu Glu Leu Leu Asp His Val Asn Asn Lys Phe Ile Glu Glu Gly<br>     965                       970                         975 | 3403 |
| aaa gaa cca ttc gcg ttc gcc tct gac tgc cgc gaa ggc att tgt ggt<br>Lys Glu Pro Phe Ala Phe Ala Ser Asp Cys Arg Glu Gly Ile Cys Gly<br>                       980                         985                        990 | 3451 |
| acc tgt ggt ctc ctc gtg   aac ggt cgc cct cac   ggc gcc gac cag<br>Thr Cys Gly Leu Leu Val   Asn Gly Arg Pro His   Gly Ala Asp Gln<br>995                               1000                          1005 | 3496 |
| aac   aag cct gcc tgt gcg   cag cgc ctg gtc agc   tac aag gaa ggc<br>Asn   Lys Pro Ala Cys Ala   Gln Arg Leu Val Ser   Tyr Lys Glu Gly<br>1010                         1015                      1020 | 3541 |
| gac   acc ctc aag atc gaa   cca ctg cgt tcc gcc   gca tac cca gtg<br>Asp   Thr Leu Lys Ile Glu   Pro Leu Arg Ser Ala   Ala Tyr Pro Val<br>1025                         1030                      1035 | 3586 |
| atc   aag gac atg gtc gtc   gac cgc tcc gca ctg   gac cgt gtc atg<br>Ile   Lys Asp Met Val Val   Asp Arg Ser Ala Leu   Asp Arg Val Met<br>1040                         1045                      1050 | 3631 |
| gaa   cag ggt ggc tac gtg   acc atc aac gca ggt   acc gca cct gac<br>Glu   Gln Gly Gly Tyr Val   Thr Ile Asn Ala Gly   Thr Ala Pro Asp<br>1055                         1060                      1065 | 3676 |

```
gct gat acc ctc cac gtc aac cac gaa acc gca gaa ctc gca ctt     3721
Ala Asp Thr Leu His Val Asn His Glu Thr Ala Glu Leu Ala Leu
1070                1075                1080 gac cac gca gcc tgc atc ggc tgt ggc gca tgt gtt gct gcc tgc     3766
Asp His Ala Ala Cys Ile Gly Cys Gly Ala Cys Val Ala Ala Cys
    1085                1090                1095 cct aac ggc gca gca cac ctg ttc acc ggc gca aag ctt gtt cac     3811
Pro Asn Gly Ala Ala His Leu Phe Thr Gly Ala Lys Leu Val His
1100                1105                1110 ctc tcc ctc ctc cca ctg ggt aag gaa gag cgc gga ctg cgt gca     3856
Leu Ser Leu Leu Pro Leu Gly Lys Glu Glu Arg Gly Leu Arg Ala
1115                1120                1125 cgt aag atg gtt gat gaa atg gaa acc aac ttc gga cac tgc tcc     3901
Arg Lys Met Val Asp Glu Met Glu Thr Asn Phe Gly His Cys Ser
1130                1135                1140 ctc tac ggc gag tgc gca gat gtc tgc ccc gca ggc atc cca ctg     3946
Leu Tyr Gly Glu Cys Ala Asp Val Cys Pro Ala Gly Ile Pro Leu
1145                1150                1155 acc gct gtg gca gct gtc acc aag gaa cgt gcg cgt gca gct ttc     3991
Thr Ala Val Ala Ala Val Thr Lys Glu Arg Ala Arg Ala Ala Phe
1160                1165                1170 cga ggc aaa gac gac tagtctttaa tccaagtaag taccggttca gacagttaaa  4046
Arg Gly Lys Asp Asp
1175 ccagaaagac gagtgaacac catgtcctcc gcgaaaaaga aacccgcacc ggagcgtatg  4106 cactacatca agggctatgt acctgtggcg tatagctctc cacactcatc cctcgagcgc  4166 agcgcaacct ggttgggcat gggattcctc ctca                             4200

<210> SEQ ID NO 74
<211> LENGTH: 257
<212> TYPE: PRT
<213> ORGANISM: Corynebacterium glutamicum

<400> SEQUENCE: 74

Met Thr Val Arg Asn Pro Asp Arg Glu Ala Ile Arg His Gly Lys Ile
1               5                   10                  15

Thr Thr Glu Ala Leu Arg Glu Arg Pro Ala Tyr Pro Thr Trp Ala Met
            20                  25                  30

Lys Leu Thr Met Ala Ile Thr Gly Leu Met Phe Gly Gly Phe Val Leu
        35                  40                  45

Val His Met Ile Gly Asn Leu Lys Ile Phe Met Pro Asp Tyr Ala Ala
    50                  55                  60

Asp Ser Ala His Pro Gly Glu Ala Gln Val Asp Val Tyr Gly Glu Phe
65                  70                  75                  80

Leu Arg Glu Ile Gly Ser Pro Ile Leu Pro His Gly Ser Val Leu Trp
                85                  90                  95

Ile Leu Arg Ile Ile Leu Leu Val Ala Leu Val Leu His Ile Tyr Cys
            100                 105                 110

Ala Phe Ala Leu Thr Gly Arg Ser His Gln Ser Arg Gly Lys Phe Arg
        115                 120                 125

Arg Thr Asn Leu Val Gly Gly Phe Asn Ser Phe Ala Thr Arg Ser Met
    130                 135                 140

Leu Val Thr Gly Ile Val Leu Ala Phe Ile Ile Phe His Ile Leu
145                 150                 155                 160

Asp Leu Thr Met Gly Val Ala Pro Ala Pro Thr Ser Phe Glu His
                165                 170                 175

Gly Glu Val Tyr Ala Asn Met Val Ala Ser Phe Ser Arg Trp Pro Val
```

```
                    180                 185                 190
Ala Ile Trp Tyr Ile Ile Ala Asn Leu Val Leu Phe Val His Leu Ser
            195                 200                 205

His Gly Ile Trp Leu Ala Val Ser Asp Leu Gly Ile Thr Gly Arg Arg
        210                 215                 220

Trp Arg Ala Ile Leu Leu Ala Val Ala Tyr Ile Val Pro Ala Leu Val
225                 230                 235                 240

Leu Ile Gly Asn Ile Thr Ile Pro Phe Ala Ile Ala Val Gly Trp Ile
            245                 250                 255

Ala

<210> SEQ ID NO 75
<211> LENGTH: 673
<212> TYPE: PRT
<213> ORGANISM: Corynebacterium glutamicum

<400> SEQUENCE: 75

Met Ser Thr His Ser Glu Thr Thr Arg Pro Glu Phe Ile His Pro Val
1               5                   10                  15

Ser Val Leu Pro Glu Val Ser Ala Gly Thr Val Leu Asp Ala Ala Glu
            20                  25                  30

Pro Ala Gly Val Pro Thr Lys Asp Met Trp Glu Tyr Gln Lys Asp His
        35                  40                  45

Met Asn Leu Val Ser Pro Leu Asn Arg Arg Lys Phe Arg Val Leu Val
50                  55                  60

Val Gly Thr Gly Leu Ser Gly Gly Ala Ala Ala Ala Leu Gly Glu
65                  70                  75                  80

Leu Gly Tyr Asp Val Lys Ala Phe Thr Tyr His Asp Ala Pro Arg Arg
                85                  90                  95

Ala His Ser Ile Ala Ala Gln Gly Gly Val Asn Ser Ala Arg Gly Lys
            100                 105                 110

Lys Val Asp Asn Asp Gly Ala Tyr Arg His Val Lys Asp Thr Val Lys
        115                 120                 125

Gly Gly Asp Tyr Arg Gly Arg Glu Ser Asp Cys Trp Arg Leu Ala Val
130                 135                 140

Glu Ser Val Arg Val Ile Asp His Met Asn Ala Ile Gly Ala Pro Phe
145                 150                 155                 160

Ala Arg Glu Tyr Gly Gly Ala Leu Ala Thr Arg Ser Phe Gly Gly Val
                165                 170                 175

Gln Val Ser Arg Thr Tyr Tyr Thr Arg Gly Gln Thr Gln Gln Leu
            180                 185                 190

Gln Leu Ser Thr Ala Ser Ala Leu Gln Arg Gln Ile His Leu Gly Ser
        195                 200                 205

Val Glu Ile Phe Thr His Asn Glu Met Val Asp Val Ile Val Thr Glu
    210                 215                 220

Arg Asn Gly Glu Lys Arg Cys Glu Gly Leu Ile Met Arg Asn Leu Ile
225                 230                 235                 240

Thr Gly Glu Leu Thr Ala His Thr Gly His Ala Val Ile Leu Ala Thr
                245                 250                 255

Gly Gly Tyr Gly Asn Val Tyr His Met Ser Thr Leu Ala Lys Asn Ser
            260                 265                 270

Asn Ala Ser Ala Ile Met Arg Ala Tyr Glu Ala Gly Ala Tyr Phe Ala
        275                 280                 285

Ser Pro Ser Phe Ile Gln Phe His Pro Thr Gly Leu Pro Val Asn Ser
    290                 295                 300
```

Thr Trp Gln Ser Lys Thr Ile Leu Met Ser Glu Ser Leu Arg Asn Asp
305                 310                 315                 320

Gly Arg Ile Trp Ser Pro Lys Glu Pro Asn Asp Asn Arg Asp Pro Asn
            325                 330                 335

Thr Ile Pro Glu Asp Glu Arg Asp Tyr Phe Leu Glu Arg Arg Tyr Pro
        340                 345                 350

Ala Phe Gly Asn Leu Val Pro Arg Asp Val Ala Ser Arg Ala Ile Ser
    355                 360                 365

Gln Gln Ile Asn Ala Gly Leu Gly Val Gly Pro Leu Asn Asn Ala Ala
370                 375                 380

Tyr Leu Asp Phe Arg Asp Ala Thr Glu Arg Leu Gly Gln Asp Thr Ile
385                 390                 395                 400

Arg Glu Arg Tyr Ser Asn Leu Phe Thr Met Tyr Glu Glu Ala Ile Gly
                405                 410                 415

Glu Asp Pro Tyr Ser Ser Pro Met Arg Ile Ala Pro Thr Cys His Phe
            420                 425                 430

Thr Met Gly Gly Leu Trp Thr Asp Phe Asn Glu Met Thr Ser Leu Pro
        435                 440                 445

Gly Leu Phe Cys Ala Gly Glu Ala Ser Trp Thr Tyr His Gly Ala Asn
    450                 455                 460

Arg Leu Gly Ala Asn Ser Leu Leu Ser Ala Ser Val Asp Gly Trp Phe
465                 470                 475                 480

Thr Leu Pro Phe Thr Ile Pro Asn Tyr Leu Gly Pro Leu Leu Gly Ser
                485                 490                 495

Glu Arg Leu Ser Glu Asp Ala Pro Glu Ala Gln Ala Ala Ile Ala Arg
            500                 505                 510

Ala Gln Ala Arg Ile Asp Arg Leu Met Gly Asn Arg Pro Glu Trp Val
        515                 520                 525

Gly Asp Asn Val His Gly Pro Glu Tyr Tyr His Arg Gln Leu Gly Asp
    530                 535                 540

Ile Leu Tyr Phe Ser Cys Gly Val Ser Arg Asn Val Glu Asp Leu Gln
545                 550                 555                 560

Asp Gly Ile Asn Lys Ile Arg Ala Leu Arg Asp Asp Phe Trp Lys Asn
                565                 570                 575

Met Arg Ile Thr Gly Ser Thr Asp Glu Met Asn Gln Val Leu Glu Tyr
            580                 585                 590

Ala Ala Arg Val Ala Asp Tyr Ile Asp Leu Gly Glu Leu Met Cys Val
        595                 600                 605

Asp Ala Leu Asp Arg Asp Glu Ser Cys Gly Ala His Phe Arg Asp Asp
    610                 615                 620

His Leu Ser Glu Asp Gly Glu Ala Glu Arg Asp Asp Glu Asn Trp Cys
625                 630                 635                 640

Phe Val Ser Ala Trp Glu Pro Gly Glu Asn Gly Thr Phe Val Arg His
                645                 650                 655

Ala Glu Pro Leu Phe Phe Glu Ser Val Pro Leu Gln Thr Arg Asn Tyr
            660                 665                 670

Lys

<210> SEQ ID NO 76
<211> LENGTH: 249
<212> TYPE: PRT
<213> ORGANISM: Corynebacterium glutamicum

<400> SEQUENCE: 76

```
Met Lys Leu Thr Leu Glu Ile Trp Arg Gln Ala Gly Pro Thr Ala Glu
1               5                   10                  15

Gly Lys Phe Glu Thr Val Gln Val Asp Ala Val Ala Gln Met Ser
            20                  25                  30

Ile Leu Glu Leu Leu Asp His Val Asn Asn Lys Phe Ile Glu Glu Gly
            35                  40                  45

Lys Glu Pro Phe Ala Phe Ala Ser Asp Cys Arg Glu Gly Ile Cys Gly
        50                  55                  60

Thr Cys Gly Leu Leu Val Asn Gly Arg Pro His Gly Ala Asp Gln Asn
65                  70                  75                  80

Lys Pro Ala Cys Ala Gln Arg Leu Val Ser Tyr Lys Glu Gly Asp Thr
            85                  90                  95

Leu Lys Ile Glu Pro Leu Arg Ser Ala Ala Tyr Pro Val Ile Lys Asp
            100                 105                 110

Met Val Val Asp Arg Ser Ala Leu Asp Arg Val Met Glu Gln Gly Gly
            115                 120                 125

Tyr Val Thr Ile Asn Ala Gly Thr Ala Pro Asp Ala Asp Thr Leu His
    130                 135                 140

Val Asn His Glu Thr Ala Glu Leu Ala Leu Asp His Ala Ala Cys Ile
145                 150                 155                 160

Gly Cys Gly Ala Cys Val Ala Ala Cys Pro Asn Gly Ala Ala His Leu
                165                 170                 175

Phe Thr Gly Ala Lys Leu Val His Leu Ser Leu Leu Pro Leu Gly Lys
            180                 185                 190

Glu Glu Arg Gly Leu Arg Ala Arg Lys Met Val Asp Glu Met Glu Thr
        195                 200                 205

Asn Phe Gly His Cys Ser Leu Tyr Gly Glu Cys Ala Asp Val Cys Pro
    210                 215                 220

Ala Gly Ile Pro Leu Thr Ala Val Ala Val Thr Lys Glu Arg Ala
225                 230                 235                 240

Arg Ala Ala Phe Arg Gly Lys Asp Asp
                245

<210> SEQ ID NO 77
<211> LENGTH: 4200
<212> TYPE: DNA
<213> ORGANISM: Brevibacterium lactofermentum
<220> FEATURE:
<221> NAME/KEY: CDS
<222> LOCATION: (449)..(1219)
<220> FEATURE:
<221> NAME/KEY: CDS
<222> LOCATION: (1239)..(3257)
<220> FEATURE:
<221> NAME/KEY: CDS
<222> LOCATION: (3260)..(4006)

<400> SEQUENCE: 77
aggtgttgca aagttgttga ttttcgcttt tcgacgcagc ccgccgccat cgggtgcccg      60
gcgtggtcag gccacatgcg ccccgggaac ttttgggca cctacggtgc aacagttgcg    120
aaaattgtgt cacctgcgca aagccttgct tctattcggg aaattcgggt gtctaaactt    180
tttggttgat accaaacggg gttagaaact gttcagatcg gtatcctgtg aggaagctca    240
ccttggtttt agaatgttga aaaagcctca cgtttccgca ggtagagcac actcaattaa    300
atgagcgtca aacgacaata aagtaaggct accctaataa ctgggttttt atgcctctaa    360
acagtcagtt gggggcggta ggggagcgtc ccatgactgg ttaatgcctc gatctgggac    420
gtacagtaac agcgacactg gaggtgcc atg act gtt aga aat ccc gac cgt       472
```

-continued

```
                Met Thr Val Arg Asn Pro Asp Arg
                  1               5 gag gca atc cgt cac gga aaa att acg acg gag gcg ctg cgt gag cgt    520
Glu Ala Ile Arg His Gly Lys Ile Thr Thr Glu Ala Leu Arg Glu Arg
 10              15                  20 ccc gca tac ccg acc tgg gca atg aag ctg acc atg gcc atc act ggc    568
Pro Ala Tyr Pro Thr Trp Ala Met Lys Leu Thr Met Ala Ile Thr Gly
 25              30                  35                  40 cta atc ttc ggt ggc ttc gtt ctt gtt cac atg atc gga aac ctg aaa    616
Leu Ile Phe Gly Gly Phe Val Leu Val His Met Ile Gly Asn Leu Lys
                 45                  50                  55 atc ttc atg ccg gac tac gca gcc gat tct gcg cat ccg ggt gaa gca    664
Ile Phe Met Pro Asp Tyr Ala Ala Asp Ser Ala His Pro Gly Glu Ala
                 60                  65                  70 caa gta gat gtc tac ggc gag ttc ctg cgt gag atc gga tcc ccg atc    712
Gln Val Asp Val Tyr Gly Glu Phe Leu Arg Glu Ile Gly Ser Pro Ile
             75                  80                  85 ctc cca cac ggc tca gtc ctc tgg atc cta cgt att atc ctg ctg gtc    760
Leu Pro His Gly Ser Val Leu Trp Ile Leu Arg Ile Ile Leu Leu Val
 90                  95                 100 gca ttg gtt ctg cac atc tac tgt gca ttc gca ttg acc ggc cgt tct    808
Ala Leu Val Leu His Ile Tyr Cys Ala Phe Ala Leu Thr Gly Arg Ser
105                 110                 115                 120 cac cag tcc cgc gga aag ttc cgc cgt acc aac ctc gtt ggc ggc ttc    856
His Gln Ser Arg Gly Lys Phe Arg Arg Thr Asn Leu Val Gly Gly Phe
                125                 130                 135 aac tcc ttc gcg acc cgc tcc atg ctg gtg acc gga atc gtt ctc ctt    904
Asn Ser Phe Ala Thr Arg Ser Met Leu Val Thr Gly Ile Val Leu Leu
                140                 145                 150 gcg ttc att atc ttc cac atc ctc gac ctg acc atg ggt gtt gct cca    952
Ala Phe Ile Ile Phe His Ile Leu Asp Leu Thr Met Gly Val Ala Pro
                155                 160                 165 gca gcc cca act tca ttc gag cac ggc gaa gta tac gca aat atg gtg   1000
Ala Ala Pro Thr Ser Phe Glu His Gly Glu Val Tyr Ala Asn Met Val
170                 175                 180 gct tcc ttt agc cgc tgg cct gta gca att tgg tac atc att gcc aac   1048
Ala Ser Phe Ser Arg Trp Pro Val Ala Ile Trp Tyr Ile Ile Ala Asn
185                 190                 195                 200 ctg gtc ctg ttc gtc cac ctg tct cac ggc atc tgg ctt gca gtc tct   1096
Leu Val Leu Phe Val His Leu Ser His Gly Ile Trp Leu Ala Val Ser
                205                 210                 215 gac ctg gga atc acc gga cgt cgc tgg agg gca atc ctc ctc gca gtt   1144
Asp Leu Gly Ile Thr Gly Arg Arg Trp Arg Ala Ile Leu Leu Ala Val
                220                 225                 230 gcg tac atc gtt cct gca ctg gtc ctg atc ggc aac atc acc att ccg   1192
Ala Tyr Ile Val Pro Ala Leu Val Leu Ile Gly Asn Ile Thr Ile Pro
                235                 240                 245 ttc gcc atc gct gtt ggc tgg att gcg taaaggttag gaagaattt atg agc   1244
Phe Ala Ile Ala Val Gly Trp Ile Ala                      Met Ser
                250                 255 act cac tct gaa acc acc cgc cca gag ttc atc cac cca gtc tca gtc   1292
Thr His Ser Glu Thr Thr Arg Pro Glu Phe Ile His Pro Val Ser Val
260                 265                 270                 275 ctc cca gag gtc tca gct ggt acg gtc ctt gac gct gct gag cca gca   1340
Leu Pro Glu Val Ser Ala Gly Thr Val Leu Asp Ala Ala Glu Pro Ala
                280                 285                 290 ggc gtt ccc acc aaa gat atg tgg gaa tac caa aaa gac cac atg aac   1388
Gly Val Pro Thr Lys Asp Met Trp Glu Tyr Gln Lys Asp His Met Asn
                295                 300                 305 ctg gtc tcc cca ctg aac cga cgc aag ttc cgc gtc ctc gtc gtt ggc   1436
Leu Val Ser Pro Leu Asn Arg Arg Lys Phe Arg Val Leu Val Val Gly
```

```
                Leu Val Ser Pro Leu Asn Arg Arg Lys Phe Arg Val Leu Val Val Gly
                    310                 315                 320 acc ggc ctg tcc ggt ggc gct gca gca gca gcc ctc ggc gaa ctc gga      1484
Thr Gly Leu Ser Gly Gly Ala Ala Ala Ala Ala Leu Gly Glu Leu Gly
325                 330                 335 tac gac gtc aag gcg ttc acc tac cac gac gca cct cgc cgt gcg cac      1532
Tyr Asp Val Lys Ala Phe Thr Tyr His Asp Ala Pro Arg Arg Ala His
340                 345                 350                 355 tcc att gct gca cag ggt ggc gtt aac tcc gcc cgc ggc aag aag gta      1580
Ser Ile Ala Ala Gln Gly Gly Val Asn Ser Ala Arg Gly Lys Lys Val
        360                 365                 370 gac aac gac ggc gca tac cgc cac gtc aag gac acc gtc aag ggc ggc      1628
Asp Asn Asp Gly Ala Tyr Arg His Val Lys Asp Thr Val Lys Gly Gly
375                 380                 385 gac tac cgt ggc cgc gag tcc gac tgc tgg cgt ctc gcc gtc gag tcc      1676
Asp Tyr Arg Gly Arg Glu Ser Asp Cys Trp Arg Leu Ala Val Glu Ser
            390                 395                 400 gtc cgc gtc atc gac cac atg aac gcc atc ggt gca cca ttc gcc cgc      1724
Val Arg Val Ile Asp His Met Asn Ala Ile Gly Ala Pro Phe Ala Arg
405                 410                 415 gaa tac ggt ggc gcc ttg gca acc cgt tcc ttc ggt ggt gtg cag gtc      1772
Glu Tyr Gly Gly Ala Leu Ala Thr Arg Ser Phe Gly Gly Val Gln Val
420                 425                 430                 435 tcc cgt acc tac tac acc cgt gga caa acc gga cag cag ctg cag ctc      1820
Ser Arg Thr Tyr Tyr Thr Arg Gly Gln Thr Gly Gln Gln Leu Gln Leu
                440                 445                 450 tcc acc gca tcc gca cta cag cgc cag atc cac ctc ggc tcc gta gag      1868
Ser Thr Ala Ser Ala Leu Gln Arg Gln Ile His Leu Gly Ser Val Glu
        455                 460                 465 atc ttc acc cat aac gaa atg gtt gac gta att gtc acc gaa cgt aat      1916
Ile Phe Thr His Asn Glu Met Val Asp Val Ile Val Thr Glu Arg Asn
470                 475                 480 ggt gaa aag cgc tgc gaa ggc ctg atc atg cgc aac ctg atc acc ggc      1964
Gly Glu Lys Arg Cys Glu Gly Leu Ile Met Arg Asn Leu Ile Thr Gly
            485                 490                 495 gag ctc acc gca cac acc ggc cat gcc gtt atc ctg gca acc ggt ggc      2012
Glu Leu Thr Ala His Thr Gly His Ala Val Ile Leu Ala Thr Gly Gly
500                 505                 510                 515 tac ggc aac gtg tac cac atg tcc acc ctg gcg aag aac tcc aac gcc      2060
Tyr Gly Asn Val Tyr His Met Ser Thr Leu Ala Lys Asn Ser Asn Ala
                520                 525                 530 tcg gcc atc atg cgt gca tac gaa gcc ggc gca tac ttc gcg tcc cca      2108
Ser Ala Ile Met Arg Ala Tyr Glu Ala Gly Ala Tyr Phe Ala Ser Pro
        535                 540                 545 tcg ttc atc cag ttc cac cca acc ggc ctg cct gtg aac tcc acc tgg      2156
Ser Phe Ile Gln Phe His Pro Thr Gly Leu Pro Val Asn Ser Thr Trp
550                 555                 560 cag tcc aag acc att ctg atg tcc gag tcg ctg cgt aac gac ggc cgc      2204
Gln Ser Lys Thr Ile Leu Met Ser Glu Ser Leu Arg Asn Asp Gly Arg
            565                 570                 575 atc tgg tcc cct aag gtt aag ggg gat gat cgc gat cca aac acc atc      2252
Ile Trp Ser Pro Lys Val Lys Gly Asp Asp Arg Asp Pro Asn Thr Ile
580                 585                 590                 595 cct gag gat gag cgc gac tac ttc ctg gag cgc cgc tac cca gca ttc      2300
Pro Glu Asp Glu Arg Asp Tyr Phe Leu Glu Arg Arg Tyr Pro Ala Phe
                600                 605                 610 ggt aac ctc gtc cca cgt gac gtt gct tcc cgt gcg atc tcc cag cag      2348
Gly Asn Leu Val Pro Arg Asp Val Ala Ser Arg Ala Ile Ser Gln Gln
        615                 620                 625 atc aac gct ggt ctc ggt gtt gga cct ctg aac aac gct gca tac ctg      2396
Ile Asn Ala Gly Leu Gly Val Gly Pro Leu Asn Asn Ala Ala Tyr Leu
```

```
                Ile Asn Ala Gly Leu Gly Val Gly Pro Leu Asn Asn Ala Ala Tyr Leu
                            630                 635                 640 gac ttc cgc gac gct acc gag cgt ctc gga cag gac acc atc cgc gag         2444
Asp Phe Arg Asp Ala Thr Glu Arg Leu Gly Gln Asp Thr Ile Arg Glu
645                 650                 655 cgt tac tcc aac ctc ttc acc atg tac gaa gag gca att ggt gag gac         2492
Arg Tyr Ser Asn Leu Phe Thr Met Tyr Glu Glu Ala Ile Gly Glu Asp
660                 665                 670                 675 cca tac tcc agc cca atg cgt att gca ccg acc tgc cac ttc acc atg         2540
Pro Tyr Ser Ser Pro Met Arg Ile Ala Pro Thr Cys His Phe Thr Met
                680                 685                 690 ggc ggc ctc tgg act gac ttc aac gaa atg acg tca ctc cca ggt ctg         2588
Gly Gly Leu Trp Thr Asp Phe Asn Glu Met Thr Ser Leu Pro Gly Leu
            695                 700                 705 ttc tgc gca ggc gaa gca tcc tgg acc tac cac ggt gca aac cgt ctg         2636
Phe Cys Ala Gly Glu Ala Ser Trp Thr Tyr His Gly Ala Asn Arg Leu
        710                 715                 720 ggc gca aac tcc ctg ctt tcc gct tcc gtc gat ggc tgg ttc acc ctg         2684
Gly Ala Asn Ser Leu Leu Ser Ala Ser Val Asp Gly Trp Phe Thr Leu
    725                 730                 735 cca ttc acc atc cct aac tac ctc gga cca ttg ctt ggc gcc gag cgt         2732
Pro Phe Thr Ile Pro Asn Tyr Leu Gly Pro Leu Leu Gly Ala Glu Arg
740                 745                 750                 755 ctg gca gag gat gca cca gaa gca gtc cag gca atc gaa cgc gct caa         2780
Leu Ala Glu Asp Ala Pro Glu Ala Val Gln Ala Ile Glu Arg Ala Gln
                760                 765                 770 gca cgc att gac cgc ctc atg ggc aac cgc cca gag tgg gtc ggt gac         2828
Ala Arg Ile Asp Arg Leu Met Gly Asn Arg Pro Glu Trp Val Gly Asp
            775                 780                 785 aac gtt cac gga cct gag tac tac cac cgc cag ctt ggc gat atc ctg         2876
Asn Val His Gly Pro Glu Tyr Tyr His Arg Gln Leu Gly Asp Ile Leu
        790                 795                 800 tac ttc tcc tgt ggc gtt tct cga aac gta aag gat ctc cag gac ggt         2924
Tyr Phe Ser Cys Gly Val Ser Arg Asn Val Lys Asp Leu Gln Asp Gly
    805                 810                 815 atc gac aag atc cgt gcg ctc cgc gag gac ttc tgg aag aac atg cgc         2972
Ile Asp Lys Ile Arg Ala Leu Arg Glu Asp Phe Trp Lys Asn Met Arg
820                 825                 830                 835 atc acc ggc agc acc gat gag atg aac cag gtt ctc gaa tac gca gca         3020
Ile Thr Gly Ser Thr Asp Glu Met Asn Gln Val Leu Glu Tyr Ala Ala
                840                 845                 850 cgc gta gct gat tac atc gac ctc ggc gaa ctc atg tgt gtc gac gca         3068
Arg Val Ala Asp Tyr Ile Asp Leu Gly Glu Leu Met Cys Val Asp Ala
            855                 860                 865 ctc gac cgc gac gag tcc tgt ggc gct cac ttc cgc gac gac cac ctc         3116
Leu Asp Arg Asp Glu Ser Cys Gly Ala His Phe Arg Asp Asp His Leu
        870                 875                 880 tcc gaa gat ggc gaa gca gaa cgt gac gac gaa aac tgg tgc ttc gtc         3164
Ser Glu Asp Gly Glu Ala Glu Arg Asp Asp Glu Asn Trp Cys Phe Val
    885                 890                 895 tcc gca tgg gaa cca ggc gag aac gga acc ttc gtc cgc cac gca gaa         3212
Ser Ala Trp Glu Pro Gly Glu Asn Gly Thr Phe Val Arg His Ala Glu
900                 905                 910                 915 cca ctg ttc ttc gaa tcc gtc cca ctg cag aca agg aac tac aag ta          3259
Pro Leu Phe Phe Glu Ser Val Pro Leu Gln Thr Arg Asn Tyr Lys
                920                 925                 930 atg aaa ctt aca ctt gag atc tgg cgt caa gca ggc cca act gcg gaa         3307
Met Lys Leu Thr Leu Glu Ile Trp Arg Gln Ala Gly Pro Thr Ala Glu
            935                 940                 945 ggc aag ttc gaa acc gtc cag gtt gac gac gcc gtc gcg cag atg tcc         3355
```

```
Gly Lys Phe Glu Thr Val Gln Val Asp Asp Ala Val Ala Gln Met Ser
            950                 955                 960 atc ctg gag ctg ctt gac cac gta aac aac aag ttc atc gaa gaa ggc      3403
Ile Leu Glu Leu Leu Asp His Val Asn Asn Lys Phe Ile Glu Glu Gly
            965                 970                 975 aag gaa cca ttc gca ttc gcg tct gac tgc cgc gaa ggc atc tgt ggt      3451
Lys Glu Pro Phe Ala Phe Ala Ser Asp Cys Arg Glu Gly Ile Cys Gly
        980                 985                 990 acc tgt ggt ctc ctc gtg  aac ggc cgc cct cac  ggc gcc gac cag        3496
Thr Cys Gly Leu Leu Val  Asn Gly Arg Pro His  Gly Ala Asp Gln
995                1000                   1005 aac  aag cct gcc tgt gcg  cag cgc ttg gtc agc  tac aac gaa ggc       3541
Asn  Lys Pro Ala Cys Ala  Gln Arg Leu Val Ser  Tyr Asn Glu Gly
1010                 1015                  1020 gac  acc ctc aag atc gaa  cca ctg cgt tcc gcc  gca tac cca gtg       3586
Asp  Thr Leu Lys Ile Glu  Pro Leu Arg Ser Ala  Ala Tyr Pro Val
1025                 1030                  1035 atc  aag gac atg gtc gtc  gac cgc tcc gca ctg  gac cgc gtc atg       3631
Ile  Lys Asp Met Val Val  Asp Arg Ser Ala Leu  Asp Arg Val Met
1040                 1045                  1050 gaa  cag ggt ggc tac gtg  acc atc aac gca ggt  acc gca cct gac       3676
Glu  Gln Gly Gly Tyr Val  Thr Ile Asn Ala Gly  Thr Ala Pro Asp
1055                 1060                  1065 gct  gat acc ctc cac gtc  aac cac gaa acc gca  gaa ctc gca ctt       3721
Ala  Asp Thr Leu His Val  Asn His Glu Thr Ala  Glu Leu Ala Leu
1070                 1075                  1080 gac  cac gca gcc tgc atc  ggc tgt ggt gca tgt  gtc gct gcc tgc       3766
Asp  His Ala Ala Cys Ile  Gly Cys Gly Ala Cys  Val Ala Ala Cys
1085                 1090                  1095 cct  aac ggc gca gca cac  ctg ttc acc ggc gca  aag ctt gtt cac       3811
Pro  Asn Gly Ala Ala His  Leu Phe Thr Gly Ala  Lys Leu Val His
1100                 1105                  1110 ctc  tcc ctc ctc cca ctg  ggt aag gaa gag cgc  gga ctg cgt gca       3856
Leu  Ser Leu Leu Pro Leu  Gly Lys Glu Glu Arg  Gly Leu Arg Ala
1115                 1120                  1125 cgt  aag atg gtt gat gaa  atg gaa acc aac ttc  gga cac tgc tcc       3901
Arg  Lys Met Val Asp Glu  Met Glu Thr Asn Phe  Gly His Cys Ser
1130                 1135                  1140 ctc  tac ggc gag tgc gca  gac gtc tgc ccc gca  ggc att cca ctg       3946
Leu  Tyr Gly Glu Cys Ala  Asp Val Cys Pro Ala  Gly Ile Pro Leu
1145                 1150                  1155 acc  gct gtg gca gct gtc  acc aag gaa cgt gcg  cgt gca gct ttc       3991
Thr  Ala Val Ala Ala Val  Thr Lys Glu Arg Ala  Arg Ala Ala Phe
1160                 1165                  1170 cga  ggc aaa gac gac tagtctttaa tccaagtaag taacggttca gacagttaaa    4046
Arg  Gly Lys Asp Asp
1175 ccagaaagac gagtgaacac catgtcctcc gagaataaga attccgcacc ggagcgtatg    4106 cactacatca agggctatgt acctgtggcg tacaactctc cacactcatc cctcgagcgc    4166 agcgcaacct ggttgggcat gggattcctc ctca                                4200

<210> SEQ ID NO 78
<211> LENGTH: 257
<212> TYPE: PRT
<213> ORGANISM: Brevibacterium lactofermentum

<400> SEQUENCE: 78

Met Thr Val Arg Asn Pro Asp Arg Glu Ala Ile Arg His Gly Lys Ile
1               5                   10                  15
```

```
Thr Thr Glu Ala Leu Arg Glu Arg Pro Ala Tyr Pro Thr Trp Ala Met
            20                  25                  30

Lys Leu Thr Met Ala Ile Thr Gly Leu Ile Phe Gly Gly Phe Val Leu
        35                  40                  45

Val His Met Ile Gly Asn Leu Lys Ile Phe Met Pro Asp Tyr Ala Ala
 50                  55                  60

Asp Ser Ala His Pro Gly Glu Ala Gln Val Asp Val Tyr Gly Glu Phe
 65                  70                  75                  80

Leu Arg Glu Ile Gly Ser Pro Ile Leu Pro His Gly Ser Val Leu Trp
                85                  90                  95

Ile Leu Arg Ile Ile Leu Leu Val Ala Leu Val Leu His Ile Tyr Cys
            100                 105                 110

Ala Phe Ala Leu Thr Gly Arg Ser His Gln Ser Arg Gly Lys Phe Arg
            115                 120                 125

Arg Thr Asn Leu Val Gly Gly Phe Asn Ser Phe Ala Thr Arg Ser Met
            130                 135                 140

Leu Val Thr Gly Ile Val Leu Leu Ala Phe Ile Ile Phe His Ile Leu
145                 150                 155                 160

Asp Leu Thr Met Gly Val Ala Pro Ala Ala Pro Thr Ser Phe Glu His
                165                 170                 175

Gly Glu Val Tyr Ala Asn Met Val Ala Ser Phe Ser Arg Trp Pro Val
                180                 185                 190

Ala Ile Trp Tyr Ile Ile Ala Asn Leu Val Leu Phe Val His Leu Ser
            195                 200                 205

His Gly Ile Trp Leu Ala Val Ser Asp Leu Gly Ile Thr Gly Arg Arg
            210                 215                 220

Trp Arg Ala Ile Leu Leu Ala Val Ala Tyr Ile Val Pro Ala Leu Val
225                 230                 235                 240

Leu Ile Gly Asn Ile Thr Ile Pro Phe Ala Ile Ala Val Gly Trp Ile
                245                 250                 255

Ala
```

<210> SEQ ID NO 79
<211> LENGTH: 673
<212> TYPE: PRT
<213> ORGANISM: Brevibacterium lactofermentum

<400> SEQUENCE: 79

```
Met Ser Thr His Ser Glu Thr Thr Arg Pro Glu Phe Ile His Pro Val
 1               5                  10                  15

Ser Val Leu Pro Glu Val Ser Ala Gly Thr Val Leu Asp Ala Ala Glu
            20                  25                  30

Pro Ala Gly Val Pro Thr Lys Asp Met Trp Glu Tyr Gln Lys Asp His
        35                  40                  45

Met Asn Leu Val Ser Pro Leu Asn Arg Arg Lys Phe Arg Val Leu Val
 50                  55                  60

Val Gly Thr Gly Leu Ser Gly Ala Ala Ala Ala Leu Gly Glu
 65                  70                  75                  80

Leu Gly Tyr Asp Val Lys Ala Phe Thr Tyr His Asp Ala Pro Arg Arg
                85                  90                  95

Ala His Ser Ile Ala Ala Gln Gly Gly Val Asn Ser Ala Arg Gly Lys
            100                 105                 110

Lys Val Asp Asn Asp Gly Ala Tyr Arg His Val Lys Asp Thr Val Lys
            115                 120                 125

Gly Gly Asp Tyr Arg Gly Arg Glu Ser Asp Cys Trp Arg Leu Ala Val
```

-continued

```
                130                 135                 140
Glu Ser Val Arg Val Ile Asp His Met Asn Ala Ile Gly Ala Pro Phe
145                 150                 155                 160

Ala Arg Glu Tyr Gly Gly Ala Leu Ala Thr Arg Ser Phe Gly Gly Val
                165                 170                 175

Gln Val Ser Arg Thr Tyr Tyr Thr Arg Gly Gln Thr Gly Gln Gln Leu
                180                 185                 190

Gln Leu Ser Thr Ala Ser Ala Leu Gln Arg Gln Ile His Leu Gly Ser
                195                 200                 205

Val Glu Ile Phe Thr His Asn Glu Met Val Asp Val Ile Val Thr Glu
210                 215                 220

Arg Asn Gly Glu Lys Arg Cys Glu Gly Leu Ile Met Arg Asn Leu Ile
225                 230                 235                 240

Thr Gly Glu Leu Thr Ala His Thr Gly His Ala Val Ile Leu Ala Thr
                245                 250                 255

Gly Gly Tyr Gly Asn Val Tyr His Met Ser Thr Leu Ala Lys Asn Ser
                260                 265                 270

Asn Ala Ser Ala Ile Met Arg Ala Tyr Glu Ala Gly Ala Tyr Phe Ala
                275                 280                 285

Ser Pro Ser Phe Ile Gln Phe His Pro Thr Gly Leu Pro Val Asn Ser
290                 295                 300

Thr Trp Gln Ser Lys Thr Ile Leu Met Ser Glu Ser Leu Arg Asn Asp
305                 310                 315                 320

Gly Arg Ile Trp Ser Pro Lys Val Lys Gly Asp Asp Arg Asp Pro Asn
                325                 330                 335

Thr Ile Pro Glu Asp Glu Arg Asp Tyr Phe Leu Glu Arg Arg Tyr Pro
                340                 345                 350

Ala Phe Gly Asn Leu Val Pro Arg Asp Val Ala Ser Arg Ala Ile Ser
                355                 360                 365

Gln Gln Ile Asn Ala Gly Leu Gly Val Gly Pro Leu Asn Asn Ala Ala
                370                 375                 380

Tyr Leu Asp Phe Arg Asp Ala Thr Glu Arg Leu Gly Gln Asp Thr Ile
385                 390                 395                 400

Arg Glu Arg Tyr Ser Asn Leu Phe Thr Met Tyr Glu Glu Ala Ile Gly
                405                 410                 415

Glu Asp Pro Tyr Ser Ser Pro Met Arg Ile Ala Pro Thr Cys His Phe
                420                 425                 430

Thr Met Gly Gly Leu Trp Thr Asp Phe Asn Glu Met Thr Ser Leu Pro
                435                 440                 445

Gly Leu Phe Cys Ala Gly Glu Ala Ser Trp Thr Tyr His Gly Ala Asn
450                 455                 460

Arg Leu Gly Ala Asn Ser Leu Leu Ser Ala Ser Val Asp Gly Trp Phe
465                 470                 475                 480

Thr Leu Pro Phe Thr Ile Pro Asn Tyr Leu Gly Pro Leu Leu Gly Ala
                485                 490                 495

Glu Arg Leu Ala Glu Asp Ala Pro Glu Ala Val Gln Ala Ile Glu Arg
                500                 505                 510

Ala Gln Ala Arg Ile Asp Arg Leu Met Gly Asn Arg Pro Glu Trp Val
                515                 520                 525

Gly Asp Asn Val His Gly Pro Glu Tyr Tyr His Arg Gln Leu Gly Asp
530                 535                 540

Ile Leu Tyr Phe Ser Cys Gly Val Ser Arg Asn Val Lys Asp Leu Gln
545                 550                 555                 560
```

```
Asp Gly Ile Asp Lys Ile Arg Ala Leu Arg Glu Asp Phe Trp Lys Asn
                565                 570                 575

Met Arg Ile Thr Gly Ser Thr Asp Glu Met Asn Gln Val Leu Glu Tyr
                580                 585                 590

Ala Ala Arg Val Ala Asp Tyr Ile Asp Leu Gly Glu Leu Met Cys Val
                595                 600                 605

Asp Ala Leu Asp Arg Asp Glu Ser Cys Gly Ala His Phe Arg Asp Asp
            610                 615                 620

His Leu Ser Glu Asp Gly Glu Ala Glu Arg Asp Asp Glu Asn Trp Cys
625                 630                 635                 640

Phe Val Ser Ala Trp Glu Pro Gly Glu Asn Gly Thr Phe Val Arg His
                645                 650                 655

Ala Glu Pro Leu Phe Phe Glu Ser Val Pro Leu Gln Thr Arg Asn Tyr
                660                 665                 670

Lys

<210> SEQ ID NO 80
<211> LENGTH: 249
<212> TYPE: PRT
<213> ORGANISM: Brevibacterium lactofermentum

<400> SEQUENCE: 80

Met Lys Leu Thr Leu Glu Ile Trp Arg Gln Ala Gly Pro Thr Ala Glu
1               5                   10                  15

Gly Lys Phe Glu Thr Val Gln Val Asp Asp Ala Val Ala Gln Met Ser
                20                  25                  30

Ile Leu Glu Leu Leu Asp His Val Asn Asn Lys Phe Ile Glu Glu Gly
            35                  40                  45

Lys Glu Pro Phe Ala Phe Ala Ser Asp Cys Arg Glu Gly Ile Cys Gly
        50                  55                  60

Thr Cys Gly Leu Leu Val Asn Gly Arg Pro His Gly Ala Asp Gln Asn
65              70                  75                  80

Lys Pro Ala Cys Ala Gln Arg Leu Val Ser Tyr Asn Glu Gly Asp Thr
                85                  90                  95

Leu Lys Ile Glu Pro Leu Arg Ser Ala Ala Tyr Pro Val Ile Lys Asp
                100                 105                 110

Met Val Val Asp Arg Ser Ala Leu Asp Arg Val Met Glu Gln Gly Gly
                115                 120                 125

Tyr Val Thr Ile Asn Ala Gly Thr Ala Pro Asp Ala Asp Thr Leu His
            130                 135                 140

Val Asn His Glu Thr Ala Glu Leu Ala Leu Asp His Ala Ala Cys Ile
145                 150                 155                 160

Gly Cys Gly Ala Cys Val Ala Ala Cys Pro Asn Gly Ala Ala His Leu
                165                 170                 175

Phe Thr Gly Ala Lys Leu Val His Leu Ser Leu Leu Pro Leu Gly Lys
                180                 185                 190

Glu Glu Arg Gly Leu Arg Ala Arg Lys Met Val Asp Glu Met Glu Thr
            195                 200                 205

Asn Phe Gly His Cys Ser Leu Tyr Gly Glu Cys Ala Asp Val Cys Pro
        210                 215                 220

Ala Gly Ile Pro Leu Thr Ala Val Ala Ala Val Thr Lys Glu Arg Ala
225                 230                 235                 240

Arg Ala Ala Phe Arg Gly Lys Asp Asp
                245
```